US008586052B2

(12) United States Patent
Zurawski et al.

(10) Patent No.: US 8,586,052 B2
(45) Date of Patent: Nov. 19, 2013

(54) VACCINES BASED ON TARGETING ANTIGEN TO DCIR EXPRESSED ON ANTIGEN-PRESENTING CELLS

(75) Inventors: Gerard Zurawski, Midlothian, TX (US); Jacques F. Banchereau, Montclair, NJ (US); Eynav Klechevsky, Haifa (IL); Sandra Zurawski, Midlothian, TX (US); Anne-Laure Flamar, Dallas, TX (US)

(73) Assignee: Baylor Research Institute, Dallas, TX (US)

( * ) Notice: Subject to any disclaimer, the term of this patent is extended or adjusted under 35 U.S.C. 154(b) by 0 days.

(21) Appl. No.: 13/454,404

(22) Filed: Apr. 24, 2012

(65) Prior Publication Data

US 2012/0237513 A1  Sep. 20, 2012

Related U.S. Application Data

(60) Division of application No. 13/234,914, filed on Sep. 16, 2011, which is a continuation of application No. 12/024,897, filed on Feb. 1, 2008, now Pat. No. 8,057,798.

(60) Provisional application No. 60/888,032, filed on Feb. 2, 2007.

(51) Int. Cl.
*A61K 39/12* (2006.01)
*A61K 39/145* (2006.01)
*A61K 39/21* (2006.01)
*A61K 39/395* (2006.01)
*C07K 16/46* (2006.01)
*C07K 16/28* (2006.01)

(52) U.S. Cl.
USPC .......... 424/184.1; 424/192.1; 424/206.1; 424/208.1; 424/178.1; 424/143.1; 424/152.1; 530/388.22; 530/388.7

(58) Field of Classification Search
None
See application file for complete search history.

(56) References Cited

U.S. PATENT DOCUMENTS

| | | | |
|---|---|---|---|
| 3,791,932 | A | 2/1974 | Schuurs et al. |
| 3,949,064 | A | 4/1976 | Bornstein et al. |
| 4,174,384 | A | 11/1979 | Ullman et al. |
| 4,554,101 | A | 11/1985 | Hopp |
| 5,738,985 | A | 4/1998 | Miles et al. |
| 6,277,959 | B1 | 8/2001 | Valladeau et al. |
| 6,451,995 | B1 | 9/2002 | Cheung et al. |
| 6,541,011 | B2 | 4/2003 | Punnonen et al. |
| 2005/0037001 | A1 | 2/2005 | Germeraad et al. |
| 2005/0106700 | A1 | 5/2005 | Nomura et al. |

FOREIGN PATENT DOCUMENTS

| | | |
|---|---|---|
| WO | 0063251 A1 | 10/2000 |
| WO | 2008/097817 A2 | 8/2008 |

OTHER PUBLICATIONS

Hawiger et al. Dendritic cells induce peripheral T cell unresponsiveness under steady state conditions in vivo. J Exp Med. Sep. 17, 2001;194(6):769-79.*
Allen et al. Identification of the T-cell and Ia contact residues of a T-cell antigenic epitope. Nature. Jun. 25-Jul. 1, 1987;327(6124):713-5.*
Meyer-Wentrup et al. Targeting DCIR on human plasmacytoid dendritic cells results in antigen presentation and inhibits IFN-alpha production. Blood. Apr. 15, 2008;111(8):4245-53. Epub Feb. 7, 2008.*
Banchereau, J., et al., "Immunobiology of dendritic cells." Annu Rev Immunol (2000), 18: 767-811.
Banchereau, J., et al., "Immune and clinical responses in patients with metastatic melanoma to CD34(+) progenitor-derived dendritic cell vaccine." Cancer Res (2001), 61(17): 6451-8.
Banchereau, J., et al., "Dendritic cells as vectors for therapy." Cell (2001), 106(3): 271-4.
Bates, E. E., et al., "APCs express DCIR, a novel C-type lectin surface receptor containing an immunoreceptor tyrosine-based inhibitory motif." J Immunol (1999), 163(4): 1973-83.
Bendtsen, J. D., et al., "Improved prediction of signal peptides: SignalP 3.0." J Mol Biol (2004), 340(4): 783-95.
Berard, F., et al., "Cross-priming of naive CD8 T cells against melanoma antigens using dendritic cells loaded with killed allogeneic melanoma cells." J Exp Med (2000), 192(11): 1535-44.
Bonifaz, L. C., et al., "In vivo targeting of antigens to maturing dendritic cells via the DEC-205 receptor improves T cell vaccination." J Exp Med (2004), 199(6): 815-24.
Carvalho, A. L., et al., "Cellulosome assembly revealed by the crystal structure of the cohesin-dockerin complex." Proc Natl Acad Sci U S A (2003), 100(24): 13809-14.
Deineste, Y., G. et al., "Involvement of LOX-1 in dendritic cell-mediated antigen cross-presentation." Immunity (2002), 17(3): 353-62.
Figdor, C. G., et al., "C-type lectin receptors on dendritic cells and Langerhans cells." Nat Rev Immunol (2002), 2(2): 77-84.
Geijtenbeek, T. B., et al., "Self- and nonself-recognition by C-type lectins on dendritic cells." Annu Rev Immunol (2004), 22: 33-54.
Mellman, I. et al., "Dendritic cells: specialized and regulated antigen processing machines." Cell (2001), 106(3): 255-8.
Neidhardt-Berard, E. M., et al., "Dendritic cells loaded with killed breast cancer cells induce differentiation of tumor-specific cytotoxic T lymphocytes." Breast Cancer Res (2004), 6(4): R322-8.
Palucka, A. K., et al., "Human dendritic cell subsets in NOD/SCID mice engrafted with CD34+ hematopoietic progenitors." Blood (2003), 102(9): 3302-10.
Ramakrishna, V., et al., "Mannose receptor targeting of tumor antigen pmel17 to human dendritic cells directs anti-melanoma T cell responses via multiple HLA molecules." J Immunol (2004), 172(5): 2845-52.

(Continued)

Primary Examiner — David Romeo

(57) ABSTRACT

The present invention includes compositions and methods for increasing the effectiveness of antigen presentation using a DCIR-specific antibody or fragment thereof to which an antigen is attached that forms an antibody-antigen complex, wherein the antigen is processed and presented by a dendritic cell that has been contacted with the antibody-antigen complex.

10 Claims, 23 Drawing Sheets

(56) References Cited

OTHER PUBLICATIONS

Reddy, M. P., et al., "Elimination of Fc receptor-dependent effector functions of a modified IgG4 monoclonal antibody to human CD4." J Immunol (2000), 164(4): 1925-33.

Shortman, K. et al., "Mouse and human dendritic cell subtypes." Nat Rev Immunol (2002), 2(3): 151-61.

Steinman, R. M. et al., "Active immunization against cancer with dendritic cells: the near future." Int J Cancer (2001), 94(4): 459-73.

Tacken, P. J., et al., "Effective induction of naive and recall T-cell responses by targeting antigen to human dendritic cells via a humanized anti-DC-SIGN antibody." Blood (2005), 106(4): 1278-85.

Trombetta, E. S. et al., "Cell biology of antigen processing in vitro and in vivo." Annu Rev Immunol (2005), 23: 975-1028.

Trumpfheller, C., et al. (2006). "Intensified and protective CD4+ T cell immunity in mice with anti-dendritic cell HIV gag fusion antibody vaccine." J Exp Med (2006), 203(3): 607-17.

Extended European Search Report for EP 08 72 8868 dated Aug. 3, 2010.

International Search Report and Written Opinion for PCT/US2008/052850 dated Sep. 24, 2008.

Craig, S.J., et al., "Engineered proteins containing the cohesin and dockerin domains from *Clostridium thermocellum* provides a reversible, high affinity interaction for biotechnology applications," Journal of Biotechnology (2006), Jan. 24, 2006.

Bayer, Edward A., et al., "The Cellulosome—a Treasure—Trove for Biotechnology," Tibtech, Sep. 1994, vol. 12, pp. 379-386.

Huang, Xin, et al., "Cloning and Characterization of a Novel ITIM Containing Lectin-Like Immunoreeptor LLIR and its Two Transmembrane Region Deletion Variants," Biochemical and Biophysical Research Communications, (2001), 281:131-140.

Wiley, K.N., et al., "The In-Vitro Inhibition of Rat Alloantigen Presentation by Immunotoxins-Implications for Allografting," Clin. Exp. Immunol., (1989), 76:132-137.

\* cited by examiner

VACCINES BASED ON TARGETING ANTIGEN TO DCIR EXPRESSED ON ANTIGEN-PRESENTING CELLS

CROSS-REFERENCE TO RELATED APPLICATIONS

This application is a Divisional application of U.S. patent application Ser. No. 13/234,914, filed Sep. 16, 2011, which is a Continuation of U.S. patent application Ser. No. 12/024,897, filed Feb. 1, 2008, now U.S. Pat. No. 8,057,798, issued Nov. 15, 2011, which claims priority to U.S. Provisional Application Ser. No. 60/888,032, filed Feb. 2, 2007, the contents of which are incorporated by reference herein in their entirety.

STATEMENT OF FEDERALLY FUNDED RESEARCH

This invention was made with U.S. Government support under Contract No. 1U19AI057234-0100003 awarded by the NIH. The government has certain rights in this invention.

TECHNICAL FIELD OF THE INVENTION

The present invention relates in general to the field of vaccination, and more particularly, to vaccines based on targeting antigen to DCIR expressed on antigen-presenting cells.

BACKGROUND OF THE INVENTION

Without limiting the scope of the invention, its background is described in connection with antigen presentation.

Human vaccines based on dendritic cell (DC)-targeting are a new concept that rests on compelling studies in mouse models. Here, small doses of relatively weak antigens carried to DC by antibodies directed to certain DC receptors can elicit potent and broad immune responses. To develop such vaccines for humans needs a better understanding of exactly which DC receptor should be used for this antigen-targeting application. This is because there is not always exact correspondence between the muse and human immune systems, and also because not all potential DC receptors have been examined carefully for this vaccine application.

Thus, studies that in vitro test various anti-human DC receptor targets have been initiated, for example, DCs targeted with melanoma antigen pmel17 fused to a human mAb against mannose receptor activated T cells in the context of HLA class I and class II molecules (Ramakrishna, Treml et al. 2004). Also, targeting the model antigen KLH to DCs via a humanized anti-DC-SIGN mAb effectively induced antigen-specific naive as well as dose-sparing recall T cell responses (Tacken, de Vries et al. 2005). Besides mannose receptor and DC-SIGN, human DCs express other receptors known to be involved in antigen capture. Many of these are C-type lectin receptors (CLRs) including LOX-1, DEC205, DC-ASGPR, Langerin, DCIR, BDCA-2, DECTIN-1, and CLEC-6. These CLRs are differently expressed by distinct subsets of DC and their expression can vary with the state of DC maturation (Figdor, van Kooyk et al. 2002; Geijtenbeek, van Vliet et al. 2004).

DC subsets stimulate distinct immune responses, and therefore, targeting antigen to these subsets via differentially expressed receptor should elicit different immune responses (Shortman and Liu 2002). Furthermore, different receptors on the same DC subset may direct the antigen to separate processing pathways (Trombetta and Mellman 2005). Lastly, some of these receptors are not intrinsically activating (e.g., DEC205 (Bonifaz, Bonnyay et al. 2004)), while others may be activating (e.g., LOX-1 (Delneste, Magistrelli et al. 2002)) or have not been studied thoroughly. The importance of DC-activation concomitant with antigen uptake is not known. But if this is beneficial, the DC-activation via the targeting mAb would simplify formulation of targeting vaccines.

SUMMARY OF THE INVENTION

In the context of these considerations, the present inventors have recognized an urgent need for a systematic comparison to define the most appropriate human DC-targeting receptors for desired immune outcomes by exploring in detail in vitro, $CD4^+$ and $CD8^+$ T cell naive and recall responses. This application describes the special and unexpected characteristics of a particular DC receptor—Dendritic Cell Immunoreceptor (DCIR)—which show it to be an ideal receptor for the purpose of targeting antigens to human DCs for preventative and therapeutic vaccination.

The present invention includes compositions and methods for making and using vaccine that specifically target (deliver) antigens to antigen-presenting cells for the purpose of eliciting potent and broad immune responses directed against the antigen. The purpose is primarily to evoke protective or therapeutic immune responses against the agent (pathogen or cancer) from which the antigen was derived.

More particularly, the present invention includes compositions, methods and methods for designing and making target specific a single recombinant antibody (mAb) that carries one or more antigens in a controlled modular structure, activating proteins, or other antibodies. The modular rAb carrier of the present invention can be used, e.g., to target (via one primary recombinant antibody against an internalizing human dendritic cell receptor) multiple antigens and/or antigens and an activating cytokine to dendritic cells (DC). Also, the invention also provides a way of joining two different recombinant mAbs end-to-end in a controlled and defined manner.

The present invention includes compositions and methods for increasing the effectiveness of antigen presentation by a DCIR-expressing antigen presenting cell by isolating and purifying a DCIR-specific antibody or fragment thereof to which a targeted agent is attached that forms an antibody-antigen complex, wherein the agent is processed and presented by, e.g., a dendritic cell, that has been contacted with the antibody-agent complex. In one embodiment, the antigen presenting cell is a dendritic cell and the DCIR-specific antibody or fragment thereof is bound to one half of a Coherin/Dockerin pair. The DCIR-specific antibody or fragment thereof may also be bound to one half of a Coherin/Dockerin pair and an antigen is bound to the complementary half of the Coherin/Dockerin pair to form a complex. Non-limiting examples agents include one or more peptides, proteins, lipids, carbohydrates, nucleic acids and combinations thereof.

The agent may one or more cytokine selected from interleukins, transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors, B/T-cell differentiation factors, B/T-cell growth factors, mitogenic cytokines, chemotactic cytokines, colony stimulating factors, angiogenesis factors, IFN-α, IFN-β, IFN-γ, IL1, IL2, IL3, IL4, IL5, IL6, IL7, IL8, IL9, IL10, IL11, IL12, IL13, IL14, IL15, IL16, IL17, IL18, etc., leptin, myostatin, macrophage stimulating protein, platelet-derived growth factor, TNF-α, TNF-β, NGF, CD40L, CD137L/4-1BBL, human lymphotoxin-β, G-CSF, M-CSF, GM-CSF, PDGF, IL-1α, IL1-β, IP-10, PF4, GRO, 9E3, erythropoietin, endostatin, angiostatin, VEGF, transforming growth factor (TGF) supergene family include the beta transforming growth factors (for example TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB). In another embodiment, the agent comprises an antigen that is a bacterial, viral, fungal, protozoan or cancer protein.

The present invention also includes compositions and methods for increasing the effectiveness of antigen presentation by dendritic cells comprising binding a DCIR-specific antibody or fragment thereof to which an antigen is attached that forms an antibody-antigen complex, wherein the antigen is processed and presented by a dendritic cell that has been contacted with the antibody-antigen complex. Another embodiment is the use of antibodies or other specific binding molecules directed to DCIR for delivering antigens to antigen-presenting cells for the purpose of eliciting protective or therapeutic immune responses. The use of antigen-targeting reagents specific to DCIR for vaccination via the skin; antigen-targeting reagents specific to DCIR in association with co-administered or linked adjuvant for vaccination or use for antigen-targeting (vaccination) purposes of specific antigens which can be expressed as recombinant antigen-antibody fusion proteins.

Another embodiment includes a method for increasing the effectiveness of dendritic cells by isolating patient dendritic cells; exposing the dendritic cells to activating amounts of anti-DCIR antibodies or fragments thereof and antigen to form antigen-loaded, activated dendritic cells; and reintroducing the antigen-loaded, activated dendritic cells into the patient. The antigen may be a bacterial, viral, fungal, protozoan or cancer protein. The present invention also includes an anti-DCIR immunoglobulin or portion thereof that is secreted from mammalian cells and an antigen bound to the immunoglobulin. The immunoglobulin is bound to one half of a cohesin/dockerin domain, or it may also include a complementary half of the cohesin-dockerin binding pair bound to an antigen that forms a complex with the modular rAb carrier, or a complementary half of the cohesin-dockerin binding pair that is a fusion protein with an antigen. The antigen specific domain may be a full length antibody, an antibody variable region domain, an Fab fragment, a Fab' fragment, an F(ab)2 fragment, and Fv fragment, and Fabc fragment and/or a Fab fragment with portions of the Fc domain. The anti-DCIR immunoglobulin may also be bound to a toxin selected from wherein the toxin is selected from the group consisting of a radioactive isotope, metal, enzyme, botulin, tetanus, ricin, cholera, diphtheria, aflatoxins, perfringens toxin, mycotoxins, shigatoxin, staphylococcal enterotoxin B, T2, seguitoxin, saxitoxin, abrin, cyanoginosin, alphatoxin, tetrodotoxin, aconotoxin, snake venom and spider venom. The antigen may be a fusion protein with the immunoglobulin or bound chemically covalently or not.

Another embodiment is a vaccine with a DCIR-specific antibody or fragment thereof to which an antigen is attached that forms an antibody-antigen complex, wherein the antigen is processed and presented by a dendritic cell that has been contacted with the antibody-antigen complex.

The novel antibodies of the present invention were also able to show novel tissue distribution information. Due to their specific affinity, it was found the anti-DCIR antibodies of the present invention binding monkey DCIR, and are effective for using anti-DCIR-Flu m1 targeting for expanding Flu m1-specific CD8 cells in vivo [hu-mouse], and in vitro targeting of ex vivo human skin cells. Furthermore, it was found that a complex of carbohydrate ligands for DCIR can be used as surrogates for anti-DCIR agents for antigen delivery. Therefore, another embodiment of the present invention is a T cell antigen that includes an antigenic T cell epitope peptide bound to at least a portion of a glycan that includes Neu5Acα2-3Galβ1-4GlcNAcβ1-2Manα1-3(Neu5Acα2-3Galβ1-4GlcNAcβ1-2Manα1-6)Manβ1-4GlcNAcβ1-4GlcNAcβ-Sp12 that binds specifically to DCIR. The glycan (and derivatives thereof) can also be used alone or in combination to block DCIR binding.

BRIEF DESCRIPTION OF THE DRAWINGS

For a more complete understanding of the features and advantages of the present invention, reference is now made to the detailed description of the invention along with the accompanying figures and in which.

Figure 1:
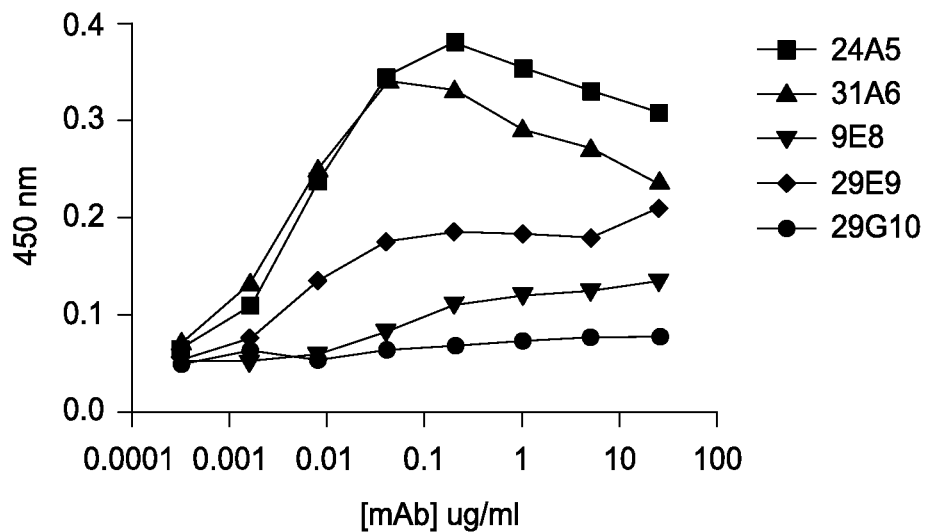
FIG. 1 shows that many, but not all, hybridoma supernatants elicited specific production of MCP-1 when compared to controls, namely mAbs 4C7, 9E8, 19E3, 1G3, 10A5, 29G10, 3C2, 3G2, 24A5, 30F3, 12E2, 5F9, 2F11, 24E7, 31A6, 6A11, 29E9, 2H8, 30D9, 6C8, 35F1, 3F12 were selected for further characterization.

The modular rAb carrier is able to carry any number of active agents, e.g., antibiotics, anti-infective agents, antiviral agents, anti-tumoral agents, antipyretics, analgesics, anti-inflammatory agents, therapeutic agents for osteoporosis, enzymes, cytokines, anticoagulants, polysaccharides, collagen, cells, and combinations of two or more of the foregoing active agents. Examples of antibiotics for delivery using the present invention include, without limitation, tetracycline, aminoglycosides, penicillins, cephalosporins, sulfonamide drugs, chloramphenicol sodium succinate, erythromycin, vancomycin, lincomycin, clindamycin, nystatin, amphotericin B, amantidine, idoxuridine, p-amino salicyclic acid, isoniazid, rifampin, antinomycin D, mithramycin, daunomycin, adriamycin, bleomycin, vinblastine, vincristine, procarbazine, imidazole carboxamide, and the like.

Examples of anti-tumor agents for delivery using the present invention include, without limitation, doxorubicin, Daunorubicin, taxol, methotrexate, and the like. Examples of antipyretics and analgesics include aspirin, Motrin®, Ibuprofen®, naprosyn, acetaminophen, and the like.

Examples of anti-inflammatory agents for delivery using the present invention include, without limitation, include NSAIDS, aspirin, steroids, dexamethasone, hydrocortisone, prednisolone, Diclofenac Na, and the like.

Examples of therapeutic agents for treating osteoporosis and other factors acting on bone and skeleton include for delivery using the present invention include, without limitation, calcium, alendronate, bone GLa peptide, parathyroid hormone and its active fragments, histone H4-related bone formation and proliferation peptide and mutations, derivatives and analogs thereof.

Examples of enzymes and enzyme cofactors for delivery using the present invention include, without limitation, pancrease, L-asparaginase, hyaluronidase, chymotrypsin, trypsin, tPA, streptokinase, urokinase, pancreatin, collagenase, trypsinogen, chymotrypsinogen, plasminogen, streptokinase, adenyl cyclase, superoxide dismutase (SOD), and the like.

Examples of cytokines for delivery using the present invention include, without limitation, interleukins, transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Cytokines may be B/T-cell differentiation factors, B/T-cell growth factors, mitogenic cytokines, chemotactic cytokines, colony stimulating factors, angiogenesis factors, IFN-α, IFN-β, IFN-γ, IL1, IL2, IL3, IL4, IL5, IL6, IL7, IL8, IL9, IL10, IL11, IL12, IL13, IL14, IL15, IL16, IL17, IL18, etc., leptin, myostatin, macrophage stimulating protein, platelet-derived growth factor, TNF-α, TNF-β, NGF, CD40L, CD137L/4-1BBL, human lymphotoxin-β, G-CSF, M-CSF, GM-CSF, PDGF, IL-1α, IL1-β, IP-10, PF4, GRO, 9E3, erythropoietin, endostatin, angiostatin, VEGF or any fragments or combinations thereof. Other cytokines include members of the transforming growth factor (TGF) supergene family include the beta transforming growth factors (for example TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB).

Examples of growth factors for delivery using the present invention include, without limitation, growth factors that can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Examples of anticoagulants for delivery using the present invention include, without limitation, include warfarin, heparin, Hirudin, and the like. Examples of factors acting on the immune system include for delivery using the present invention include, without limitation, factors which control inflammation and malignant neoplasms and factors which attack infective microorganisms, such as chemotactic peptides and bradykinins.

Examples of viral antigens include, but are not limited to, e.g., retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS1, NS1, NS1-NS2A, 80% E, and other Japanese encephalitis viral antigen components; rabies viral antigens such as rabies glycoprotein, rabies nucleoprotein and other rabies viral antigen components. See Fundamental Virology, Second Edition, eds. Fields, B. N. and Knipe, D. M. (Raven Press, New York, 1991) for additional examples of viral antigens.

Antigenic targets that may be delivered using the rAb-DC/DC-antigen vaccines of the present invention include genes encoding antigens such as viral antigens, bacterial antigens, fungal antigens or parasitic antigens. Viruses include picornavirus, coronavirus, togavirus, flavirvirus, rhabdovirus, paramyxovirus, orthomyxovirus, bunyavirus, arenavirus, reovirus, retrovirus, papilomavirus, parvovirus, herpesvirus, poxvirus, hepadnavirus, and spongiform virus. Other viral targets include influenza, herpes simplex virus 1 and 2, measles, dengue, smallpox, polio or HIV. Pathogens include trypanosomes, tapeworms, roundworms, helminthes, malaria. Tumor markers, such as fetal antigen or prostate specific antigen, may be targeted in this manner. Other examples include: HIV env proteins and hepatitis B surface antigen. Administration of a vector according to the present invention for vaccination purposes would require that the vector-associated antigens be sufficiently non-immunogenic to enable long term expression of the transgene, for which a strong immune response would be desired. In some cases, vaccination of an individual may only be required infrequently, such as yearly or biennially, and provide long term immunologic protection against the infectious agent. Specific examples of organisms, allergens and nucleic and amino sequences for use in vectors and ultimately as antigens with the present invention may be found in U.S. Pat. No. 6,541,011, relevant portions incorporated herein by reference, in particular, the tables that match organisms and specific sequences that may be used with the present invention.

Bacterial antigens for use with the rAb vaccine disclosed herein include, but are not limited to, e.g., bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens such as lipopolysaccharides and other gram-negative bacterial antigen components, *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; *haemophilus* influenza bacterial antigens such as capsular polysaccharides and other *haemophilus* influenza bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens. Partial or whole pathogens may also be: *haemophilus influenza; Plasmodium falciparum; neisseria meningitidis; streptococcus pneumoniae; neisseria gonorrhoeae; salmonella* serotype typhi; *shigella; vibrio cholerae*; Dengue Fever; Encephalitides; Japanese Encephalitis; lyme disease; *Yersinia pestis*; west nile virus; yellow fever; tularemia; hepatitis (viral; bacterial); RSV (respiratory syncytial virus); HPIV 1 and HPIV 3; adenovirus; small pox; allergies and cancers.

Fungal antigens for use with compositions and methods of the invention include, but are not limited to, e.g., candida fungal antigen components; *histoplasma* fungal antigens such as heat shock protein 60 (HSP60) and other *histoplasma* fungal antigen components; cryptococcal fungal antigens such as capsular polysaccharides and other cryptococcal fungal antigen components; *coccidiodes* fungal antigens such as spherule antigens and other *coccidiodes* fungal antigen components; and tinea fungal antigens such as trichophytin and other *coccidiodes* fungal antigen components.

Examples of protozoal and other parasitic antigens include, but are not limited to, e.g., *plasmodium falciparum* antigens such as merozoite surface antigens, sporozoite surface antigens, circumsporozoite antigens, gametocyte/gamete surface antigens, blood-stage antigen pf 155/RESA and other plasmodial antigen components; *toxoplasma* antigens such as SAG-1, p30 and other toxoplasmal antigen components; schistosomae antigens such as glutathione-S-transferase, paramyosin, and other schistosomal antigen components; *leishmania major* and other leishmaniae antigens such as gp63, lipophosphoglycan and its associated protein and other leishmanial antigen components; and *trypanosoma cruzi* antigens such as the 75-77 kDa antigen, the 56 kDa antigen and other trypanosomal antigen components.

Antigen that can be targeted using the rAb of the present invention will generally be selected based on a number of factors, including: likelihood of internalization, level of immune cell specificity, type of immune cell targeted, level of immune cell maturity and/or activation and the like. Examples of cell surface markers for dendritic cells include, but are not limited to, MHC class I, MHC Class II, B7-2, CD18, CD29, CD31, CD43, CD44, CD45, CD54, CD58, CD83, CD86, CMRF-44, CMRF-56, DCIR and/or ASPGR and the like; while in some cases also having the absence of CD2, CD3, CD4, CD8, CD14, CD15, CD16, CD 19, CD20, CD56, and/or CD57. Examples of cell surface markers for antigen presenting cells include, but are not limited to, MHC class I, MHC Class II, CD40, CD45, B7-1, B7-2, IFN-γ receptor and IL-2 receptor, ICAM-1 and/or Fcy receptor. Examples of cell surface markers for T cells include, but are not limited to, CD3, CD4, CD8, CD 14, CD20, CD11b, CD16, CD45 and HLA-DR.

Target antigens on cell surfaces for delivery includes those characteristic of tumor antigens typically will be derived from the cell surface, cytoplasm, nucleus, organelles and the like of cells of tumor tissue. Examples of tumor targets for the antibody portion of the present invention include, without limitation, hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, pancreatic cancer, genitourinary tumors such cervix, uterus, ovarian cancer, vaginal cancer, testicular cancer, prostate cancer or penile cancer, bone tumors, vascular tumors, or cancers of the lip, nasopharynx, pharynx and oral cavity, esophagus, rectum, gall bladder, biliary tree, larynx, lung and bronchus, bladder, kidney, brain and other parts of the nervous system, thyroid, Hodgkin's disease, non-Hodgkin's lymphoma, multiple myeloma and leukemia.

Examples of antigens that may be delivered alone or in combination to immune cells for antigen presentation using the present invention includes tumor proteins, e.g., mutated oncogenes; viral proteins associated with tumors; and tumor mucins and glycolipids. The antigens may be viral proteins associated with tumors would be those from the classes of viruses noted above. Certain antigens may be characteristic of tumors (one subset being proteins not usually expressed by a tumor precursor cell), or may be a protein which is normally expressed in a tumor precursor cell, but having a mutation characteristic of a tumor. Other antigens include mutant variant(s) of the normal protein having an altered activity or subcellular distribution, e.g., mutations of genes giving rise to tumor antigens.

Specific non-limiting examples of tumor antigens include: CEA, prostate specific antigen (PSA), HER-2/neu, BAGE, GAGE, MAGE 1-4, 6 and 12, MUC (Mucin) (e.g., MUC-1, MUC-2, etc.), GM2 and GD2 gangliosides, ras, myc, tyrosinase, MART (melanoma antigen), Pmel 17(gp100), GnT-V intron V sequence (N-acetylglucoaminyltransferase V intron V sequence), Prostate Ca psm, PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP), Bcl-2, and Ki-67. In addition, the immunogenic molecule can be an autoantigen involved in the initiation and/or propagation of an autoimmune disease, the pathology of which is largely due to the activity of antibodies specific for a molecule expressed by the relevant target organ, tissue, or cells, e.g., SLE or MG. In such diseases, it can be desirable to direct an ongoing antibody-mediated (i.e., a Th2-type) immune response to the relevant autoantigen towards a cellular (i.e., a Th1-type) immune response. Alternatively, it can be desirable to prevent onset of or decrease the level of a Th2 response to the autoantigen in a subject not having, but who is suspected of being susceptible to, the relevant autoimmune disease by prophylactically inducing a Th1 response to the appropriate autoantigen. Autoantigens of interest include, without limitation: (a) with respect to SLE, the Smith protein, RNP ribonucleoprotein, and the SS-A and SS-B proteins; and (b) with respect to MG, the acetylcholine receptor. Examples of other miscellaneous antigens involved in one or more types of autoimmune response include, e.g., endogenous hormones such as luteinizing hormone, follicular stimulating hormone, testosterone, growth hormone, prolactin, and other hormones.

Antigens involved in autoimmune diseases, allergy, and graft rejection can be used in the compositions and methods of the invention. For example, an antigen involved in any one or more of the following autoimmune diseases or disorders can be used in the present invention: diabetes, diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis. Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor. Examples of antigens involved in allergy include pollen antigens such as Japanese cedar pollen antigens, ragweed pollen antigens, rye grass pollen antigens, animal derived antigens such as dust mite antigens and feline antigens, histocompatiblity antigens, and penicillin and other therapeutic drugs. Examples of antigens involved in graft rejection include antigenic components of the graft to be transplanted into the graft recipient such as heart, lung, liver, pancreas, kidney, and neural graft components. The antigen may be an altered peptide ligand useful in treating an autoimmune disease.

As used herein, the term "epitope(s)" refer to a peptide or protein antigen that includes a primary, secondary or tertiary structure similar to an epitope located within any of a number of pathogen polypeptides encoded by the pathogen DNA or RNA. The level of similarity will generally be to such a degree that monoclonal or polyclonal antibodies directed against such polypeptides will also bind to, react with, or otherwise recognize, the peptide or protein antigen. Various immunoassay methods may be employed in conjunction with such antibodies, such as, for example, Western blotting, ELISA, RIA, and the like, all of which are known to those of skill in the art. The identification of pathogen epitopes, and/or their functional equivalents, suitable for use in vaccines is part of the present invention. Once isolated and identified, one may readily obtain functional equivalents. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

The preparation of vaccine compositions that includes the nucleic acids that encode antigens of the invention as the active ingredient, may be prepared as injectables, either as liquid solutions or suspensions; solid forms suitable for solution in, or suspension in, liquid prior to infection can also be prepared. The preparation may be emulsified, encapsulated in liposomes. The active immunogenic ingredients are often mixed with carriers which are pharmaceutically acceptable and compatible with the active ingredient.

The term "pharmaceutically acceptable carrier" refers to a carrier that does not cause an allergic reaction or other untoward effect in subjects to whom it is administered. Suitable pharmaceutically acceptable carriers include, for example, one or more of water, saline, phosphate buffered saline, dextrose, glycerol, ethanol, or the like and combinations thereof. In addition, if desired, the vaccine can contain minor amounts of auxiliary substances such as wetting or emulsifying agents, pH buffering agents, and/or adjuvants which enhance the effectiveness of the vaccine. Examples of adjuvants that may be effective include but are not limited to: aluminum hydroxide, N-acetyl-muramyl-L-threonyl-D-isoglutamine (thr-MDP), N-acetyl-nor-muramyl-L-alanyl-D-isoglutamine, MTP-PE and RIBI, which contains three components extracted from bacteria, monophosphoryl lipid A, trehalose dimycolate and cell wall skeleton (MPL+TDM+CWS) in a 2% squalene/Tween 80 emulsion. Other examples of adjuvants include DDA (dimethyldioctadecylammonium bromide), Freund's complete and incomplete adjuvants and QuilA. In addition, immune modulating substances such as lymphokines (e.g., IFN-γ, IL-2 and IL-12) or synthetic IFN-γ inducers such as poly I:C can be used in combination with adjuvants described herein.

Pharmaceutical products that may include a naked polynucleotide with a single or multiple copies of the specific nucleotide sequences that bind to specific DNA-binding sites of the apolipoproteins present on plasma lipoproteins as described in the current invention. The polynucleotide may encode a biologically active peptide, antisense RNA, or ribozyme and will be provided in a physiologically acceptable administrable form. Another pharmaceutical product that may spring from the current invention may include a highly purified plasma lipoprotein fraction, isolated according to the methodology, described herein from either the patient's blood or other source, and a polynucleotide containing single or multiple copies of the specific nucleotide sequences that bind to specific DNA-binding sites of the apolipoproteins present on plasma lipoproteins, prebound to the purified lipoprotein fraction in a physiologically acceptable, administrable form.

Yet another pharmaceutical product may include a highly purified plasma lipoprotein fraction which contains recombinant apolipoprotein fragments containing single or multiple copies of specific DNA-binding motifs, prebound to a polynucleotide containing single or multiple copies of the specific nucleotide sequences, in a physiologically acceptable administrable form. Yet another pharmaceutical product may include a highly purified plasma lipoprotein fraction which contains recombinant apolipoprotein fragments containing single or multiple copies of specific DNA-binding motifs, prebound to a polynucleotide containing single or multiple copies of the specific nucleotide sequences, in a physiologically acceptable administrable form.

The dosage to be administered depends to a great extent on the body weight and physical condition of the subject being treated as well as the route of administration and frequency of treatment. A pharmaceutical composition that includes the naked polynucleotide prebound to a highly purified lipoprotein fraction may be administered in amounts ranging from 1 μg to 1 mg polynucleotide and 1 μg to 100 mg protein.

Administration of an rAb and rAb complexes a patient will follow general protocols for the administration of chemotherapeutics, taking into account the toxicity, if any, of the vector. It is anticipated that the treatment cycles would be repeated as necessary. It also is contemplated that various standard therapies, as well as surgical intervention, may be applied in combination with the described gene therapy.

Where clinical application of a gene therapy is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention may include an effective amount of the compound, dissolved or dispersed in a pharmaceutically acceptable carrier or aqueous medium. Such compositions can also be referred to as inocula. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions. The compositions of the present invention may include classic pharmaceutical preparations. Dispersions also can be prepared in glycerol, liquid polyethylene glycols, and mixtures thereof and in oils. Under ordinary conditions of storage and use, these preparations contain a preservative to prevent the growth of microorganisms.

Disease States. Depending on the particular disease to be treated, administration of therapeutic compositions according to the present invention will be via any common route so long as the target tissue is available via that route in order to maximize the delivery of antigen to a site for maximum (or in some cases minimum) immune response. Administration will generally be by orthotopic, intradermal, subcutaneous, intramuscular, intraperitoneal or intravenous injection. Other areas for delivery include: oral, nasal, buccal, rectal, vaginal or topical. Topical administration would be particularly advantageous for treatment of skin cancers. Such compositions would normally be administered as pharmaceutically acceptable compositions that include physiologically acceptable carriers, buffers or other excipients.

Vaccine or treatment compositions of the invention may be administered parenterally, by injection, for example, either subcutaneously or intramuscularly. Additional formulations which are suitable for other modes of administration include suppositories, and in some cases, oral formulations or formulations suitable for distribution as aerosols. In the case of the oral formulations, the manipulation of T-cell subsets employing adjuvants, antigen packaging, or the addition of individual cytokines to various formulation that result in improved oral vaccines with optimized immune responses. For suppositories, traditional binders and carriers may include, for example, polyalkylene glycols or triglycerides; such suppositories may be formed from mixtures containing the active ingredient in the range of 0.5% to 10%, preferably 1%-2%. Oral formulations include such normally employed excipients as, for example, pharmaceutical grades of mannitol, lactose, starch magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25-70%.

The antigen encoding nucleic acids of the invention may be formulated into the vaccine or treatment compositions as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups can also be derived from inorganic bases such as, for example, sodium, potassium, ammonium, calcium, or ferric hydroides, and such organic bases as isopropylamine, trimethylamine, 2-ethylamino ethanol, histidine, procaine, and the like.

Vaccine or treatment compositions are administered in a manner compatible with the dosage formulation, and in such amount as will be prophylactically and/or therapeutically effective. The quantity to be administered depends on the subject to be treated, including, e.g., capacity of the subject's immune system to synthesize antibodies, and the degree of protection or treatment desired. Suitable dosage ranges are of the order of several hundred micrograms active ingredient per vaccination with a range from about 0.1 mg to 1000 mg, such as in the range from about 1 mg to 300 mg, and preferably in the range from about 10 mg to 50 mg. Suitable regiments for initial administration and booster shots are also variable but are typified by an initial administration followed by subsequent inoculations or other administrations. Precise amounts of active ingredient required to be administered depend on the judgment of the practitioner and may be peculiar to each subject. It will be apparent to those of skill in the art that the therapeutically effective amount of nucleic acid molecule or fusion polypeptides of this invention will depend, inter alia, upon the administration schedule, the unit dose of antigen administered, whether the nucleic acid molecule or fusion polypeptide is administered in combination with other therapeutic agents, the immune status and health of the recipient, and the therapeutic activity of the particular nucleic acid molecule or fusion polypeptide.

The compositions can be given in a single dose schedule or in a multiple dose schedule. A multiple dose schedule is one in which a primary course of vaccination may include, e.g., 1-10 separate doses, followed by other doses given at subsequent time intervals required to maintain and or reinforce the immune response, for example, at 1-4 months for a second dose, and if needed, a subsequent dose(s) after several months. Periodic boosters at intervals of 1-5 years, usually 3 years, are desirable to maintain the desired levels of protective immunity. The course of the immunization can be followed by in vitro proliferation assays of peripheral blood lymphocytes (PBLs) co-cultured with ESAT6 or ST-CF, and by measuring the levels of IFN-γ released from the primed lymphocytes. The assays may be performed using conventional labels, such as radionucleotides, enzymes, fluorescent labels and the like. These techniques are known to one skilled in the art and can be found in U.S. Pat. Nos. 3,791,932, 4,174,384 and 3,949,064, relevant portions incorporated by reference.

The modular rAb carrier and/or conjugated rAb carrier-(cohesion/dockerin and/or dockerin-cohesin)-antigen complex (rAb-DC/DC-antigen vaccine) may be provided in one or more "unit doses" depending on whether the nucleic acid vectors are used, the final purified proteins, or the final vaccine form is used. Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. The subject to be treated may also be evaluated, in particular, the state of the subject's immune system and the protection desired. A unit dose need not be administered as a single injection but may include continuous infusion over a set period of time. Unit dose of the present invention may conveniently may be described in terms of DNA/kg (or protein/Kg) body weight, with ranges between about 0.05, 0.10, 0.15, 0.20, 0.25, 0.5, 1, 10, 50, 100, 1,000 or more mg/DNA or protein/kg body weight are administered. Likewise the amount of rAb-DC/DC-antigen vaccine delivered can vary from about 0.2 to about 8.0 mg/kg body weight. Thus, in particular embodiments, 0.4 mg, 0.5 mg, 0.8 mg, 1.0 mg, 1.5 mg, 2.0 mg, 2.5 mg, 3.0 mg, 4.0 mg, 5.0 mg, 5.5 mg, 6.0 mg, 6.5 mg, 7.0 mg and 7.5 mg of the vaccine may be delivered to an individual in vivo. The dosage of rAb-DC/DC-antigen vaccine to be administered depends to a great extent on the weight and physical condition of the subject being treated as well as the route of administration and the frequency of treatment. A pharmaceutical composition that includes a naked polynucleotide prebound to a liposomal or viral delivery vector may be administered in amounts ranging from 1 μg to 1 mg polynucleotide to 1 μg to 100 mg protein. Thus, particular compositions may include between about 1 μg, 5 μg, 10 μg, 20 μg, 30 μg, 40 μg, 50 μg, 60 μg, 70 μg, 80 μg, 100 μg, 150 μg, 200 μg, 250 μg, 500 μg, 600 μg, 700 μg, 800 μg, 900 μg or 1,000 μg polynucleotide or protein that is bound independently to 1 μg, 5 μg, 10 μg, 20 μg, 3.0 μg, 40 μg 50 μg, 60 μg, 70 μg, 80 μg, 100 μg, 150 μg, 200 μg, 250 μg, 500 μg, 600 μg, 700 μg, 800 μg, 900 μg, 1 mg, 1.5 mg, 5 mg, 10 mg, 20 mg, 30 mg, 40 mg, 50 mg, 60 mg, 70 mg, 80 mg, 90 mg or 100 mg vector.

The present invention was tested in an in vitro cellular system that measures immune stimulation of human Flu-specific T cells by dendritic cells to which Flu antigen has been targeted. The results shown herein demonstrate the specific expansion of such antigen specific cells at doses of the antigen which are by themselves ineffective in this system.

The present invention may also be used to make a modular rAb carrier that is, e.g., a recombinant humanized mAb (directed to a specific human dendritic cell receptor) complexed with protective antigens from Ricin, Anthrax toxin, and *Staphylococcus* B enterotoxin. The potential market for this entity is vaccination of all military personnel and stored vaccine held in reserve to administer to large population centers in response to any biothreat related to these agents. The invention has broad application to the design of vaccines in general, both for human and animal use. Industries of interest include the pharmaceutical and biotechnology industries.

General methods—Restriction and DNA modification enzymes were from NEB. Plasmid and DNA fragment purification was with Qiagen products. SDS-PAGE was via 4-12% Bis-Tris gels stained with Simply Blue (Invitrogen). Chromatography columns and resins were from GE Healthcare. Plasmid constructs were confirmed by DNA sequencing (MCLAB). DNA primers were from Operon or Midland Certified Reagent Company. Sequence analysis was via Sequencher (Gene Codes). Protein concentrations based on calculated extinction coefficient predicted by the ProtParam tool (2005) were measured by UV absorption (Nanoprop ND-1000). The sequences are provided in the Sequence Listing SEQ ID NOS.: 1-39, incorporated herein by reference, which are alignments anti-DCIR mAb Heavy (SEQ ID NOS.: 1-17) and Light chain signal peptide and variable region sequences (SEQ ID NOS.:18-39). Predicted N-terminal signal peptide region, sequence differences between variants or between closely related sequences were determined using Sequencher.

Sequence of the C-terminal extension to the Cohesin domain of Cohesin-Flex-hMART-1-PeptideA-6×His protein. The immunodominant peptide sequence peptide is underlined and bold residues bounding the peptide are native to the antigen sequence. C-terminal His tags are to facilitate purification via Ni++ affinity chromatography. C186 Cohesin-Flex-hMART-1-Peptide A-6×His:

(SEQ ID NO.: 40)
ASDTTEARHPPVTTPTTDRRKGTTAEELAGIGILTVILGGKRTNNSTPTKGEFCRYPSHW

RPLEHHHHHH.

Antigen expression constructs—PCR was used to amplify the ORF of Influenza A/Puerto Rico/8/34/Mount Sinai (H1N1) M1 protein while incorporating a Nhe I site distal to the initiator codon and a Not I site distal to the stop codon. The digested fragment was cloned into pET-28b(+) (Novagen), placing the M1 ORF in-frame with a His6 tag, thus encoding His.Flu M1 protein. The Flu M1 ORF was placed into a similar vector encoding N-terminal protein G precursor B2 domain residues 298-352 (gi|1242671) distal to the Nco I site, followed by linker residues encoding GGSGGSGGSLD (SEQ ID NO.: 41). This vector expressed ProG.Flu M1 protein with a Q246E change. A pET28b (+) derivative encoding a N-terminal 169 residue cohesin domain from *C. thermocellum* inserted between the Nco I and Nhe I sites expressed Coh.His. For expression of Coh.Flu M1.His, the Flu M1 ORF was inserted between the Nhe I and Xho I sites of the above derivative. Coh.PEP.His expression constructs were made similarly, except they utilized synthetic DNAs encoding the required sequences. The proteins were expressed in *E. coli* strain BL21 (DE3) (Novagen) or T7 Express (NEB) grown at 37° C. with selection for kanamycin resistance (40 μg/ml) and shaking at 200 rounds/min to mid log phase growth when 120 mg/L IPTG was added. After three hours, the cells were harvested by centrifugation and stored at −80 C. The ProG and Cohesin segments replaced the ectodomain segment in the AP fusion secretion vector described above, by incorporating a Sal I site in place of the initiator codon and adding a distal Xho I site for insertion at the vector Xho I site. An 'empty' AP vector was made by deleting the ectodomain segment. Respectively, these constructs directed secreted of ProG.AP, Coh.AP and AP.

Expression and purification of recombinant proteins—*E. coli* cells from each 1 L fermentation were resuspended in 30 ml ice-cold 0.1 M NaPO$_4$ pH 7.4 (buffer A, for ProG.Flu M1) or 50 mM Tris, 1 mM EDTA pH 8.0 (buffer B, for all other proteins) with 0.1 ml of protease inhibitor Cocktail II (Calbiochem). The cells were sonicated on ice 2×5 min at setting 18 (Fisher Sonic Dismembrator 60) with a 5 min rest period and then spun at 17,000 r.p.m. (Sorvall SA-600) for 20 min at 4° C. For ProG.Flu M1, the supernatant was passed through 5 ml Q Sepharose equilibrated in buffer A and then 5 ml hIgG beads were added to the Q flow-through and incubated with mixing at 4° C. for 1 h. The bead-bound protein was washed with 50 ml cold PBS and eluted with 2×10 ml 0.1 M glycine pH 2.7. The pooled eluates were brought to pH 5 with 0.1 M MES pH 5.0 buffer and run on a 1 ml HiTrap S column equilibrated with 50 mM MES pH 5.0 (buffer C). The column-bound protein was washed extensively with buffer C and eluted with a 0-1 M NaCl gradient in buffer C. The peak fractions were pooled. For His.Flu M1 purification the 50 ml cell lysate supernatant fraction was passed through 5 ml Q Sepharose beads and 6.25 ml 160 mM Tris, 40 mM imidazole, 4 M NaCl pH 7.9 was added to the Q Sepharose flow through. This was loaded at 4 ml/min onto a 5 ml HiTrap chelating HP column charged with Ni$^{++}$. The column-bound protein was washed with 20 mM NaPO$_4$, 300 mM NaCl pH 7.6 (buffer D) followed by another wash with 100 mM H$_3$COONa pH 4.0. Bound protein was eluted with a gradient from 100 mM to 1 M H$_3$COONa pH 4.0. The peak fractions were pooled and loaded at 4 ml/min onto a 5 ml HiTrap S column equilibrated with 100 mM H$_3$COONa pH 4.0, and washed with the equilibration buffer followed by another wash with 50 mM NaPO$_4$ pH 7.5. Bound protein was eluted with a gradient from 0-1 M NaCl in 50 mM NaPO$_4$ pH 7.5. Peak fractions eluting at about 500 mM NaCl were pooled. Preparations of His.Flu M1 had variable amounts of non-full-length products, presumably with C-terminal portions missing. For Coh.Flu M1.His purification, cells from 2 L of culture were sonicated as above, but in buffer B. After centrifugation, 2.5 ml of Triton X114 was added to the supernatant with incubation on ice for 5 min. After further incubation at 25° C. for 5 min, the supernatant was separated from the Triton X114 following centrifugation at 25° C. The extraction was repeated and the supernatant was passed through 5 ml of Q Sepharose beads and 6.25 ml 160 mM Tris, 40 mM imidazole, 4 M NaCl pH 7.9 was added to the Q Sepharose flow through. The protein was then purified by N11 chelating chromatography as described above and eluted with 0-500 mM imidazole in buffer D.

cDNA cloning and expression of chimeric mouse/human mAbs—Total RNA was prepared from hybridoma cells (RNeasy kit, Qiagen) and used for cDNA synthesis and PCR (SMART RACE kit, BD Biosciences) using supplied 5' primers and gene specific 3' primers mIgGκ, 5'ggatggtgggaagatggatacagttggtgcagcatc3'; (SEQ ID NO.: 42) mIgGλ, 5'ctaggaacagtcagcacgggacaaactcttctccacagtgtgaccttc3'; (SEQ ID NO.: 43) mIgG1, 5'gtcactggctcagggaaatagccct-tgaccaggcatc3'; (SEQ ID NO.: 44) mIgG2a, 5'ccaggcatcctagagtcaccgaggagccagt3'; (SEQ ID NO.: 45) and mIgG2b, 5'ggtgctggaggggacagtcactgagctgctcatagtgt3'. (SEQ ID NO.: 46) PCR products were cloned (pCR2.1 TA kit, Invitrogen) and characterized by DNA sequencing. Using the derived sequences for the mouse H and L chain V-region cDNAs, specific primers were used to PCR amplify the signal peptide and V-regions while incorporating flanking restriction sites for cloning into expression vectors encoding downstream human IgGκ or IgG4H regions. The vector for expression of chimeric mVκ-hIgκ was built by amplifying residues 401-731 (gi|63101937|) flanked by Xho I and Not I sites and inserting this into the Xho I-Not I interval of pIRES2-DsRed2 (BD Biosciences). PCR was used to amplify the mAb Vκ region from the initiator codon, appending a Nhe I or Spe I site then CACC, to the region encoding (e.g., residue 126 of gi|76779294|), appending a Xho I site. The PCR fragment was then cloned into the Nhe I-Not I interval of the above vector. The vector for chimeric mVκ-hIgκ using the mSLAM leader was built by inserting the sequence 5'ctagttgctggctaatggaccccaaaggctcccttc-ctggagaatacttctgtttctctccctggcttttgagttgtcgtacggattaattaag ggcccactcgag3' (SEQ ID NO.: 47) into the Nhe I-Xho I interval of the above vector. PCR was used to amplify the interval between the predicted mature N-terminal codon (defined using the SignalP 3.0 Server) (Bendtsen, Nielsen et al. 2004) and the end of the mVκ region (as defined above) while appending 5'tcgtacgga3'. The fragment digested with Bsi WI and Xho I was inserted into the corresponding sites of the above vector. The control hIgκ sequence corresponds to gi|49257887| residues 26-85 and gi|21669402| residues 67-709. The control hIgG4H vector corresponds to residues 12-1473 of gi|19684072| with S229P and L236E substitutions, which stabilize a disulphide bond and abrogate residual FcR binding (Reddy, Kinney et al. 2000), inserted between the pIRES2-DsRed2 vector Bgl II and Not I sites while adding the sequence 5'gctagctgattaattaa3' instead of the stop codon. PCR was used to amplify the mAb VH region from the initiator codon, appending CACC then a Bgl II site, to the region encoding residue 473 of gi|19684072|. The PCR fragment was then cloned into the Bgl II-Apa I interval of the above vector. The vector for chimeric mVH-hIgG4 sequence using the mSLAM leader was built by inserting the sequence 5'ctagttgctggctaatggaccccaaag-gctcccttctcctggagaatacttct-gtttctctccctggcttttgagttgtcgtacggattaattaag ggccc3' (SEQ ID NO.: 48) into the Nhe I-Apa I interval of the above vector. PCR was used to amplify the interval between the predicted mature N-terminal codon and the end of the mVκ region while appending 5' tcgtacgga3'. The fragment digested with Bsi WI and Apa I was inserted into the corresponding sites of the above vector.

Various antigen coding sequences flanked by a proximal Nhe I site and a distal Not I site following the stop codon were inserted into the Nhe I-Pac I-Not I interval of the H chain vectors. Flu HA1-1 was encoded by Influenza A virus (A/Puerto Rico/8/34(H1N1)) hemagglutinin gi|21693168| residues 82-1025 (with a C982T change) with proximal 5'gctagcgata-caacagaacctgcaacacctacaacacctgtaacaa3' (SEQ ID NO.: 49) sequence (a Nhe I site followed by sequence encoding cipA cohesin-cohesin linker residues) and distal 5'caccatcaccat-caccattgagcggccgc3' (SEQ ID NO.: 50) sequence (encoding His6, a stop codon, and a Not I site). Flu HA5-1 was encoded by gi|50296052| Influenza A virus (A/Viet Nam/1203/2004 (H5N1)) hemagglutinin residues 49-990 bound by the same sequences as Flu HA1-1. Doc was encoded by gi|40671| celD residues 1923-2150 with proximal Nhe I and distal Not I sites. PSA was encoded by gi|34784812| prostate specific antigen residues 101-832 with proximal sequence 5'gctagcgatacaaca-gaacctgcaacacctacaacacctgtaa-caacaccgacaacaacacttctagcgc3' (SEQ ID NO.: 51) (Nhe I site and cipA spacer) and a distal Not I site. Flu M1-PEP was encoded by 5'gctagccccattctgagcccctgac-caaaggcattctgggctttgtgtttac-cctgaccgtgcccagcgaacgcaagggtatacttggat tcgttttcacacttact-taagcggccgc3'(SEQ ID NO.: 52). This and all other peptide-encoding sequences were created via mixtures of complimentary synthetic DNA fragments with ends compatible for cloning into Nhe I and Not I-restricted H chain vectors, or Nhe I-Xho I-restricted Coh.His vector. Preferred human codons were always used, except where restriction sites needed to be incorporated or in CipA spacer sequences.

Production levels of rAb expression constructs were tested in 5 ml transient transfections using ~2.5 μg each of the L-chain and H chain construct and the protocol described above. Supernatants were analyzed by anti-hIgG ELISA (AffiniPure Goat anti-human IgG (H+L), Jackson ImmunoResearch). In tests of this protocol, production of secreted rAb was independent of H chain and L chain vectors concentration over a ~2-fold range of each DNA concentration (i.e., the system was DNA saturated).

Generation of CD34-DCs-CD34+ HPCs were mobilized and collected from peripheral blood of normal healthy donors, who received subcutaneous recombinant G-CSF (Neupogen) 10 U/kg/day for 5 days. CD34$^+$-HPCs were obtained with the CEPRATE SC stem cell concentration system (ISOLEX). CD34-DCs were generated by culture at a concentration of 0.5×10$^6$/ml in Yssel's medium (Irvine Scientific, CA) supplemented with 5% autologous serum, 50 μM 2-β-mercaptoethanol, 1% L-glutamine, 1% penicillin/streptomycin, and the cytokines; GM-CSF (50 ng/ml; Immunex Corp.), FLT3-L (100 ng/ml; R&D), and TNF-α (10 ng/ml; R&D). Cells were transferred to fresh medium supplemented with cytokines at day 5 of culture, and harvested at day 9.

Sorting of CD34-DCs-CD34-derived DCs at day 9 of culture were harvested, and stained with anti-CD1a FITC (Biosource International) and anti-CD14 PE (BD Biosciences). CD1a$^+$CD14$^-$-LCs and CD1a$^-$CD14$^+$-intDCs were sorted with FACS Vantage™ (BD Biosciences). Purity was routinely 95-99%.

Purification of autologous CD8$^+$ T cells—Autologous CD8+ T cells were positively selected from PBMCs obtained from the identical donors by using CD8 magnetic beads (Miltenyi) after depletion with CD14, CD19, CD16, CD56 and CD4 beads. In some experiments, memory CD8+ T cells were sorted as CD8+CCR7−CD45RA−.

Cross-presentation of Flu M1 protein by CD34-DC subsets to CD8$^+$ T cells—Bulk or sorted CD34+DCs subsets, CD1a+ LCs or CD14+ IntDCs (5×10$^4$ cells/ml) from an HLA-A2 donor, were cultured with purified autologous CD8+ T cells (1×10$^6$ cells/ml) in Yssel's medium supplemented with 10% heat-inactivated pooled AB human serum, 10 U/ml IL-7 (R&D) and decreasing doses of Flu M1 that was cross-linked to an anti-DC antibody. CD40L was added to the culture after 24 h, and IL-2 was added after 3 days. Cross presentation efficiency was assessed after 8 or 10 days, by analyzing the level of antigen-specific CD8+ T cell proliferation, using specific Flu M1, HLA-A201/pMI, phycoerythrin-conjugated iTAg MHC Tetramer (Beckman Coulter).

Development of anti-human DCIR monoclonal antibodies—Receptor ectodomain.hIgG (human IgG1Fc) and HRP (horse radish peroxidase) fusion proteins were produced for immunization of mice and screening of mAbs, respectively. The expression construct for hDCIR ectodomain.IgG was described previously (Bates, Fournier et al. 1999) and used the mouse SLAM (mSLAM) signal peptide to direct secretion (Bendtsen, Nielsen et al. 2004). The expression vector for hDCIR ectodomain.AP was generated using PCR to amplify AP resides 133-1581 (gb|BC009647|) while adding a proximal in-frame Xho I site and a distal TGA stop codon and Not I site. This Xho I-Not I fragment replaced the IgG coding sequence in the above hDCIR ectodomain.IgG vector. The DCIR.HRP fusion protein vector was generated by cloning gi|208493| residues 14-940 distal to the DCIR ectodomain-coding region as defined above.

Expression and purification of recombinant proteins secreted from mammalian cells—Fusion proteins were produced using the FreeStyle™ 293 Expression System (Invitrogen) according to the manufacturer's protocol (1 mg total plasmid DNA with 1.3 ml 293 Fectin reagent/L of transfection). For recombinant antibody (rAb) production, equal amounts of vector encoding the H and L chain were co-transfected. Transfected cells are cultured for 3 days, the culture supernatant was harvested and fresh media added with continued incubation for two days. The pooled supernatants were clarified by filtration. Receptor ectodomain.hIgG was purified by HiTrap protein A affinity chromatography with elution by 0.1 M glycine pH 2.7 and then dialyzed versus PBS. rAbs were purified similarly, by using HiTrap MabSelect™ columns.

Generation of monoclonal antibodies—Mouse mAbs were generated by conventional cell fusion technology. Briefly, 6-week-old BALB/c mice were immunized intraperitoneally with 20 μg of receptor ectodomain.hIgGFc fusion protein with Ribi adjuvant, then boosts with 20 μg antigen 10 days and 15 days later. After 3 months, the mice were boosted again three days prior to taking the spleens. Alternately, mice were injected in the footpad with 1-10 μg antigen in Ribi adjuvant every 3-4 days over a 30-40 day period. 3-4 days after a final boost, draining lymph nodes were harvested. B cells from spleen or lymph node cells were fused with SP2/O-Ag 14 cells (Shulman, Wilde et al. 1978) using conventional techniques. ELISA was used to screen hybridoma supernatants against the receptor ectodomain fusion protein compared to the fusion partner alone, or versus the receptor ectodomain fused to AP (Bates, Fournier et al. 1999). Positive wells were then screened in FACS using 293F cells transiently transfected with expression plasmids encoding full-length receptor cDNAs.

For the development of anti-DCIR mAbs, supernatants from 1000 hybridoma clones screened:
  90 were + on DCIR.Ig vs. Ig ELISA
  64 were + on DCIR-293 cells by FACS
  62 FACS+ were ELISA+
  2 were 293+ (and thus not specific to DCIR)

Biological screen for anti-DCIR mAbs that stimulate cytokine production by human DC—For DC-targeting purposes, it is potentially desirable to have the antibody delivering the antigen to the DC and concomitantly activating the DC to stimulate a productive immune response against the delivered antigen. Thus we screened the panel of 62 FACS positive anti-DCIR hybridoma supernatants directly for DC stimulation activity. CD34+-derived human DC were cultured for 24 hours with the hybridoma supernatants and the DC culture supernatant was assayed 24 hours later for the presence of the chemokine MCP-1. The figure below shows that many, but not all, hybridoma supernatants elicited specific production of MCP-1 when compared to controls.

Selected hybridomas (most, but all stimulating MCP-1 production) marked in the figure above with asterisks were single cell cloned and expanded in CELLine flasks (Intergra). Hybridoma supernatants were mixed with an equal volume of 1.5 M glycine, 3 M NaCl, 1×PBS, pH 7.8 and tumbled with MabSelect resin. The resin was washed with binding buffer and eluted with 0.1 M glycine, pH 2.7. Following neutralization with 2 M Tris, mAbs were dialyzed versus PBS.

FIG. 1 shows that many, but not all, hybridoma supernatants elicited specific production of MCP-1 when compared to controls, namely mAbs 4C7, 9E8, 19E3, 1G3, 10A5, 29G10, 3C2, 3G2, 24A5, 30F3, 12E2, 5F9, 2F11, 24E7, 31A6, 6A11, 29E9, 2H8, 30D9, 6C8, 35F1, 3F12 were selected for further characterization.

Figure 2:
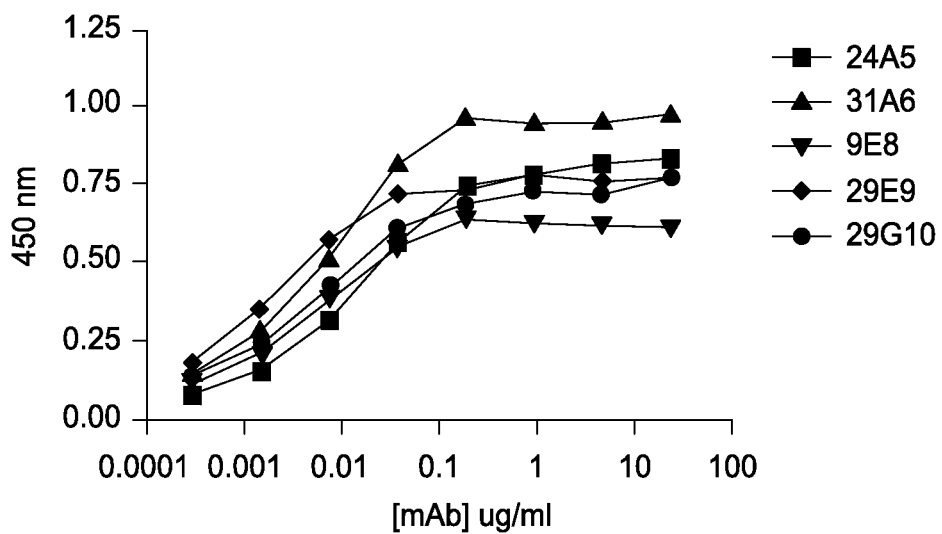
FIG. 2 shows the high affinity interaction of the mAbs with DCIR bound to plate by ELISA.

Characterization of the pure anti-DCIR mAbs—The pure mAbs were tested firstly by ELISA (DCIR.Ig bound to the plates, developed with HRP-conjugated anti-human Fc reagents) and by a DCIR.HRP capture assay (mAb bound to the plate, developed with DCIR.HRP fusion protein). FIG. 2 shows representative assay results showing high affinity interaction of the mAbs with DCIR bound to plate (controls showing specificity of binding are not shown). In the DCIR.HRP capture assay, several (but not all) of the mAbs were able to capture soluble DCIR.HRP to the plate surface. These data show that the panel of selected anti-DCIR mAbs had a range of DCIR binding affinities and properties.

The pure mAbs were also tested for FACS reactivity, firstly against 293 cells transiently transfected with expression plasmid encoding full-length DCIR, and then against various types of cultured and ex-vivo human DC. The figure below shows a representative set of mAbs titrated in a FACS analysis versus DCIR 293 cell (control cells were negative).

Figure 3:
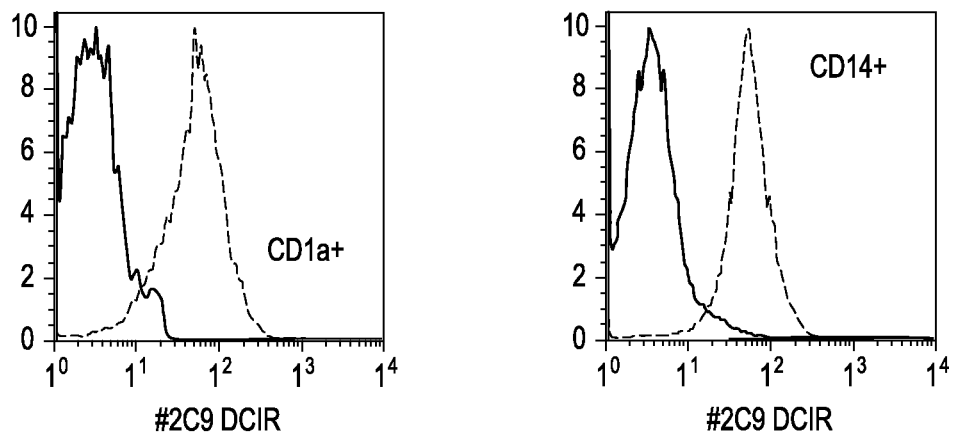
FIG. 3 shows the binding of the high affinity antibodies for use in FACS.

FIG. 3 shows that CD34-derived human DC of both CD14+ and CD1a+ subtypes express cell surface DCIR. These two DC subtypes have profoundly different roles in directing humoral versus cytolytic immune responses—thus the presence of DCIR on both subtypes suggests that antigen targeted to human DC via DCIR should elicit both types of immunity—an important feature of vaccines directed against, e.g., viral infections.

Figure 4:
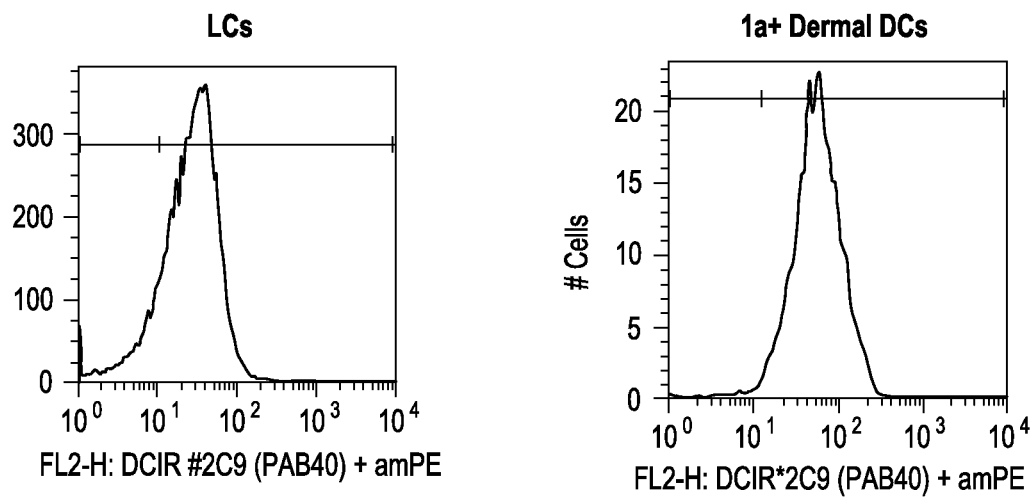
FIG. 4 shows that DCIR is also expressed on three human DC subtypes isolated directly from human skin.
Figure 4:
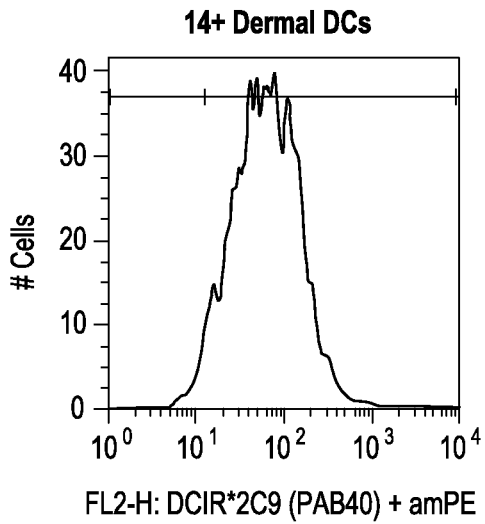

FIG. 4 shows that DCIR is also expressed on three human DC subtypes isolated directly from human skin. This observation shows that for DCIR antigen targeting vaccines, administration into the skin should be advantageous since these DC types all express the receptor. It is known that these DC types are analogous to the above cultured human DC regards their immune directing properties and therefore targeting antigen through DCIR-bearing skin DC should be advantageous for eliciting desirable mixed immune responses.

Dermal DCs and LCs were purified from normal human skin specimens. Specimens were incubated in the bacterial protease dispase type 2 for 18 h at 4° C., and then for 2 h at 37° C. Epidermal and dermal sheets were then separated, cut into small pieces (~1-10 mm) and placed in RPMI 1640 supplemented with 10% fetal bovine serum (FBS). After 2 days, the cells that migrated into the medium were collected and further enriched using a Ficoll-diatrizoate gradient, 1.077 g/dl. DCs were purified by cell sorting after staining with anti-CD1a FITC and anti-CD14 APC mAbs.

Figure 5:
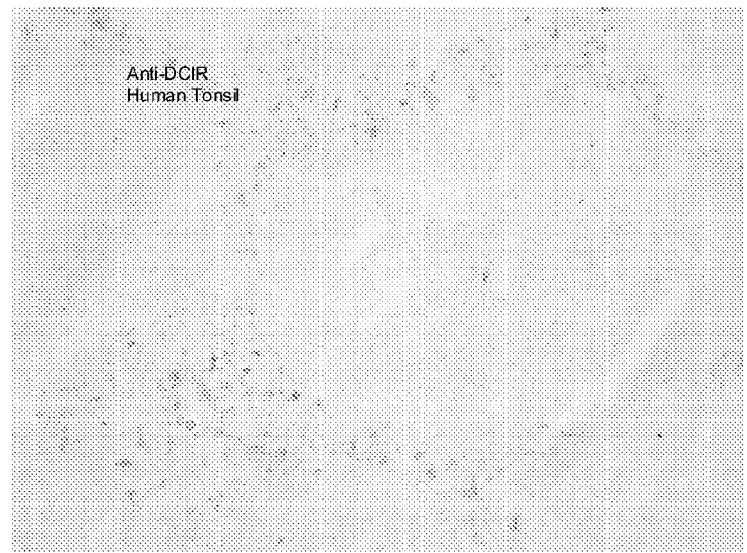
FIG. 5 shows DCIR-specific staining of a population of cells surrounding a germinal center within a human tonsil.

Presence of DCIR in other human tissues. FIG. 5 shows DCIR-specific staining of a population of cells surrounding a germinal center within a human tonsil. These cells are likely to be either resident DC or DC recently migrated to this site after e.g., loading with foreign antigen and activation. The staining shows that administration of DCIR-targeted vaccines by routes other than skin permitting access to organs in which immunity is generated should also be advantageous for eliciting immune response.

Figure 6:
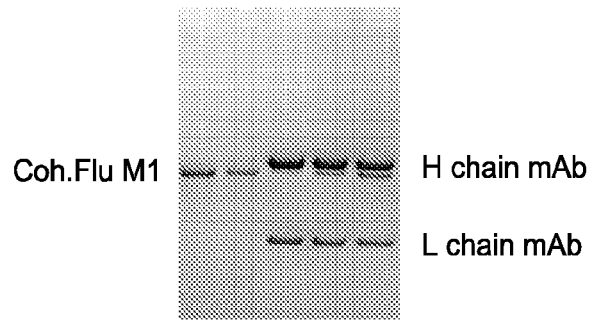
FIG. 6 shows an example of the cross-Flu M1 protein and the mAb to DCIR.
Figure 7:
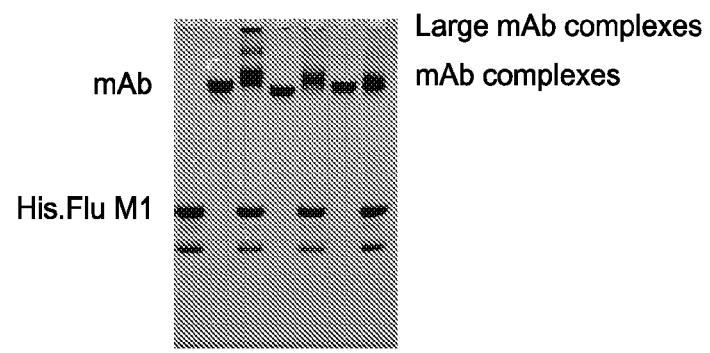
FIG. 7 shows the cross-linking of Coh.Flu M1 to Anti-DCIR_2C9 mAb.
Figure 8:
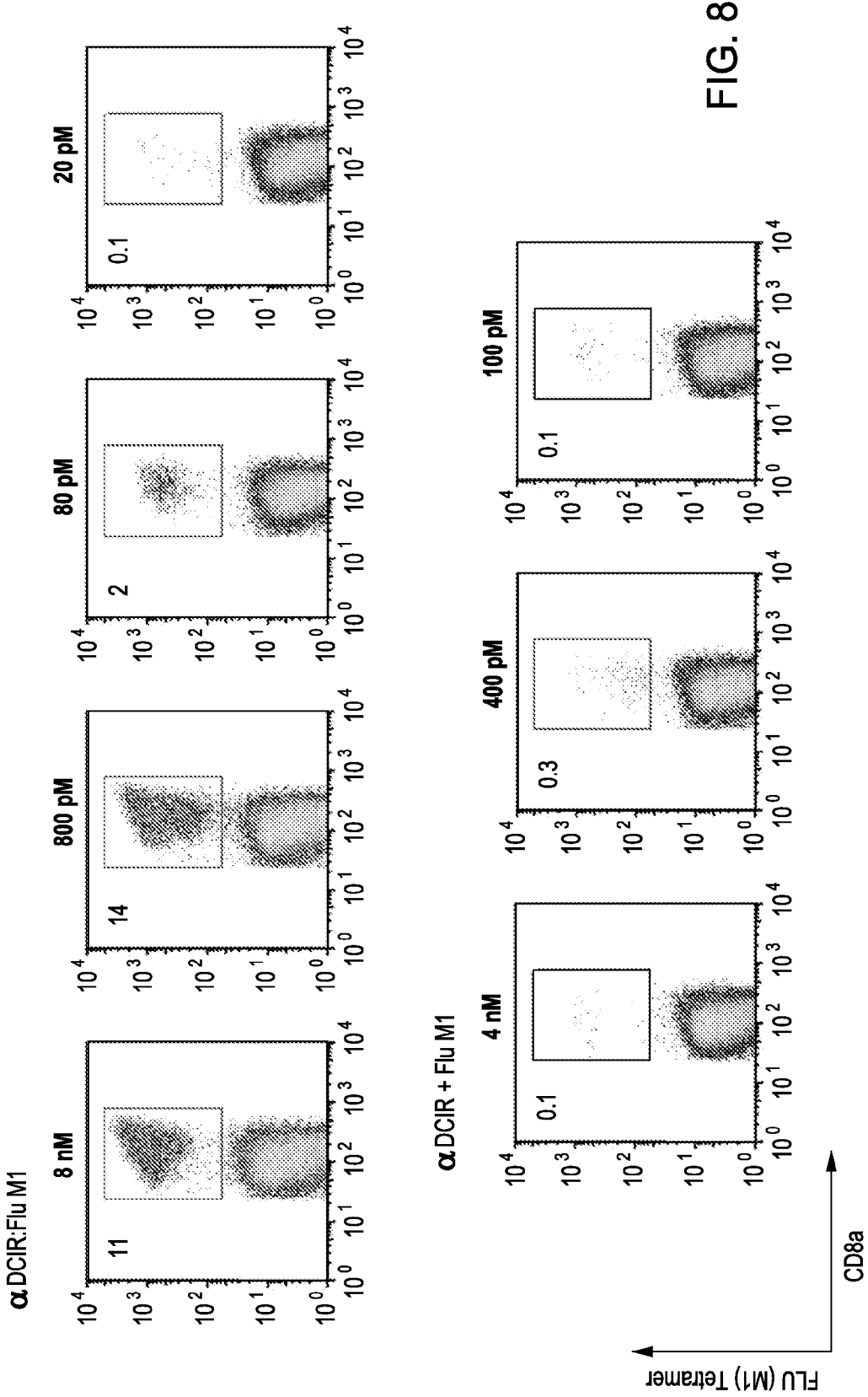
FIG. 8 shows that Flu M1 cross-linked to anti-DCIR mAb induces the expansion of Flu M1-specific CD8+ T cells more efficiently than Flu M1 protein unlinked to mAb.
Figure 9:
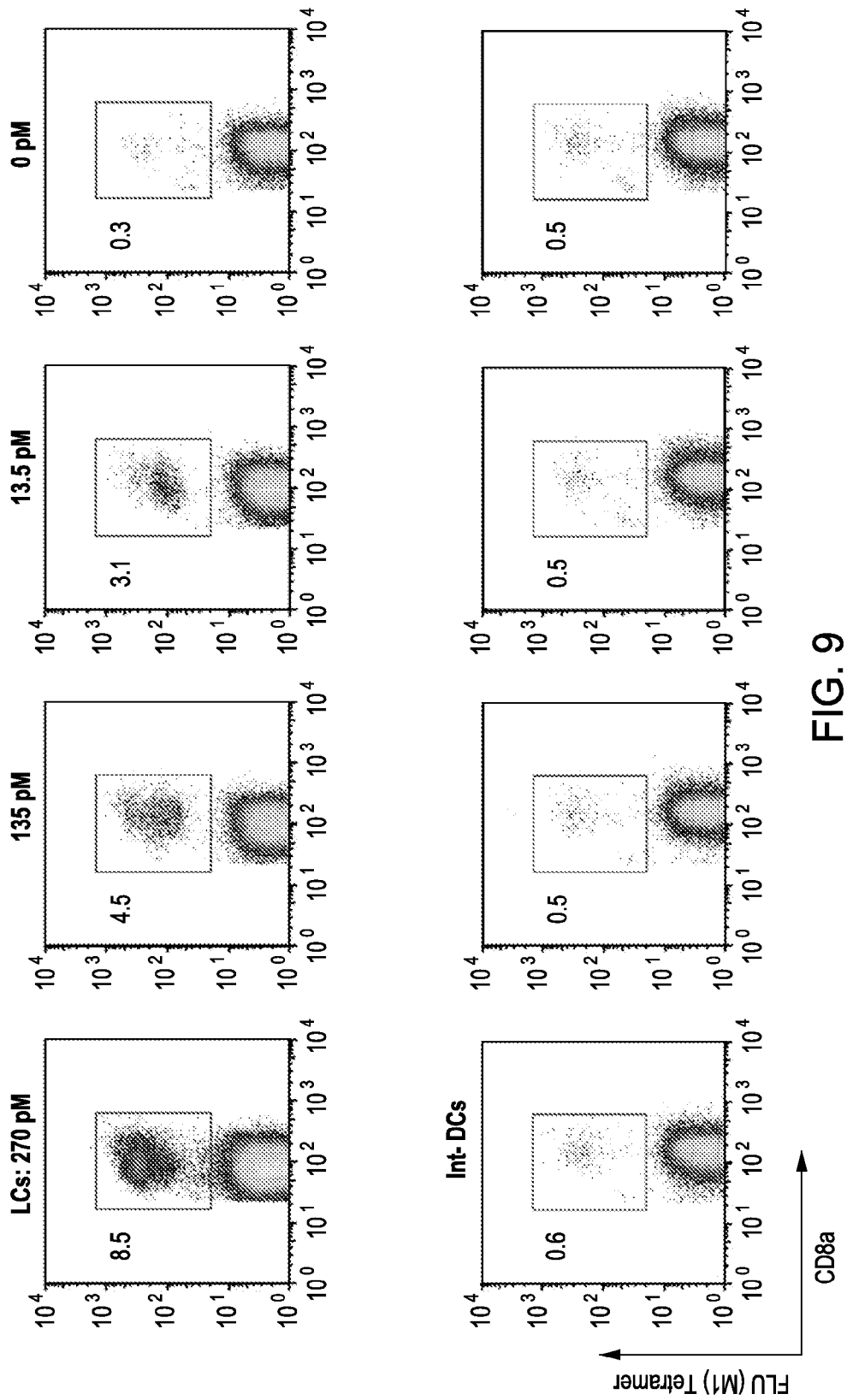
FIG. 9 shows that Flu M1 cross-linked to anti-DCIR mAb induces the expansion of Flu M1-specific CD8+ T cells more efficiently via LCs than Int-DCs.

Using anti-DCIR mAbs to target antigen to human DC. Flu M1 proteins were chemically cross-linked to mAbs using sulfosuccinimidyl 6-[3' (2-pyridyldithio)-propionamido] hexanoate (sulfo-LC-SPDP; Pierce) according to the manufacturer's protocol. The multi-step protocol involved the activation of the mAb by modification of its amines through the NHS ester group of SPDP for 30 min at room temperature followed by dialysis versus PBS. Subsequently, Flu M1 proteins, which contain two free sulfhydryl groups, were added and incubated at room temperature overnight. The efficiency of the cross-linking reaction was estimated by comparing the amount of Flu M1 protein before the reaction to the mAb, to the mAb/Flu M1 ratio after cross-linking We calculated that, on average, 50% of the mAbs had reacted to one Flu M1 molecule. FIGS. 6 and 7 show examples of the cross-Flu M1 protein and the mAb to DCIR. Analysis via reduced SDS-PAGE identified products with 1-2 Flu M1 per mAb based on the ratio of staining of Flu M1/H chain and these preparations were used in the in vitro studies. Non-reduced SDS-PAGE analysis (second figure below shows that the complexes were largely between Flu M1 and single mAbs as evidenced by a low percentage of very large complexes.

FIG. 6 shows the cross-linking of Coh.Flu M1 to Anti-DCIR_2C9 mAb. Reduced SDS-PAGE analysis of cross-linked products purified by protein G Sepharose affinity. From left to right are 2.5 μg, 1 μg Coh.Flu M1, 10 μg products from reacting Coh.Flu M1 with mAb at ratios of 1:1, 2:1, 4:1.

FIG. 7 shows the cross-linking of His.Flu M1 to mAbs. Non-reduced SDS-PAGE analysis of cross-linked products purified by protein G Sepharose affinity. From left to right are 5 μg, His.Flu M1, followed by pairs of 5 μg mAb (anti-CD1a_OKT6, anti-LANG_2G3, anti-DCIR_2C9) and 5 μg mAb reacted with of 5 μg His.Flu M1.

Anti-DC receptor mAbs cross-linked to Flu M1 protein effectively target the antigen to human DC-Anti-DC receptor mAbs were chemically cross-linked to Flu M1 protein and various doses were added to the co-culture of human CD34-derived CD1a+ DCs with autologous CD8+ T cells. CD40L was added to the culture after 24 h for DCs activation, followed by addition of IL-2, at day 3, for T cell proliferation. After 8-10 days, T cells specific for the Flu M1 peptide GILGFVFTL (SEQ ID NO.: 53) were assessed by MHC tetramer analysis. FIG. 8 shows that Flu M1 cross-linked to anti-DCIR mAb elicited the proliferation of Flu M1-specific cells, while significantly less proliferation of Flu M1-specific cells was observed with non-cross-linked Flu M1 and mAb at similar doses. The dose-ranging shows that the cross-linked mAb elicited a response at least 50-fold more effectively than free Flu M1. This data demonstrates antigen-targeting, i.e., potentiation of an immune response—in this case a recall of T cells with memory of a specific Flu M1 epitope. CD34− DCs were sorted into CD1a+LCs or CD14+IntDCs subsets. FIG. 9 shows that anti-DCIR-targeted CD11a+LCs were much more potent at directing the expansion of Flu M1-specific CD8+ cells, despite similar levels of DCIR expression on both cell types.

FIG. 8 shows that Flu M1 cross-linked to anti-DCIR mAb induces the expansion of Flu M1-specific CD8+ T cells more efficiently than Flu M1 protein unlinked to mAb. CD34− derived CD1a+ DCs were incubated with CD8+ T cells and the indicated concentrations of anti-DCIR 2C9 mAb cross-linked to His.Flu M1 or with unlinked mAb. CD8+ T cells were then analyzed for Flu M1-specific expansion. The inner boxes indicate the percentages of tetramer-specific CD8+ T cells.

FIG. 9 shows that Flu M1 cross-linked to anti-DCIR mAb induces the expansion of Flu M1-specific CD8+ T cells more efficiently via LCs than Int-DCs. LCs or Int-DCs from an HLA-A2 donor and autologous CD8+ T cells were co-cultured with the indicated concentrations of anti-DCIR_2C9 mAb cross-linked to His.Flu M1. Cross-presentation efficiency was assessed by the frequency of Flu M1-specific CD8+ T cells and analyzed with HLA-A201/pMI tetramer. The inner boxes indicate the percentages of tetramer-specific CD8+ T cells.

Figure 10:
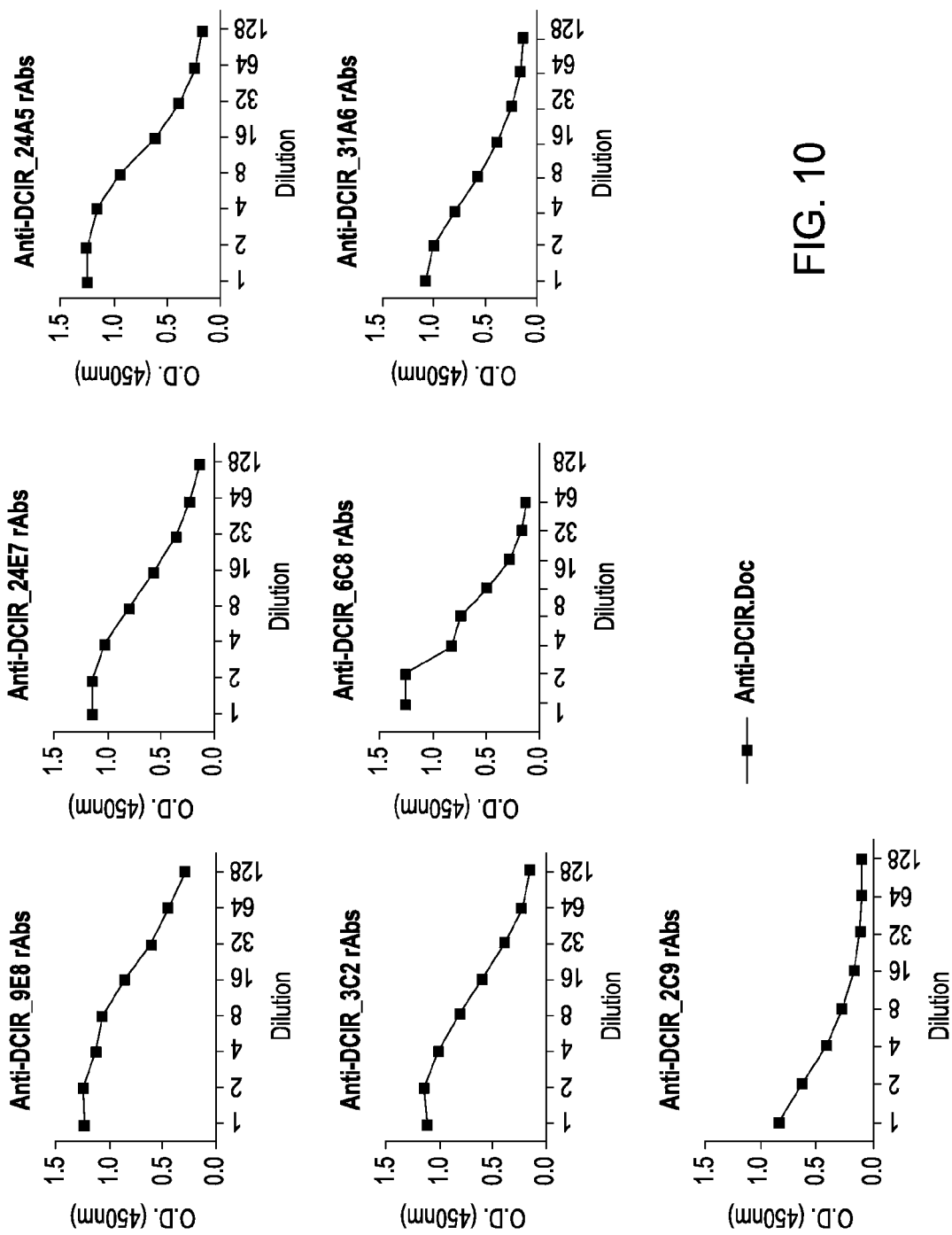
FIG. 10 shows such H+L chain vectors encoding chimeric mouse-human rAbs corresponding to a number of different anti-DCIR mAbs co-transfected into 293 cells and assayed by anti-human FC ELISA for secretion of rAb into the culture supernatant.

Development of recombinant anti-DCIR mAbs (rAbs) as prototype antigen-targeting vaccines. Vectors were developed for the expression in transiently transfected mammalian cells of secreted anti-DC receptor rAbs that were chimeras of the mouse hybridoma-encoded H and L chain variable (V) regions and human Igκ or human IgG4H constant (C) regions. V regions from L and H chains of anti-DC receptor mAbs with different specificities (I.e., from different anti-DCIR hybridomas) were cDNA cloned, characterized by DNA sequence analysis, and engineered into these vectors. FIG. 10 shows such H+L chain vectors encoding chimeric mouse-human rAbs corresponding to a number of different anti-DCIR mAbs co-transfected into 293 cells and assayed by anti-human FC ELISA for secretion of rAb into the culture supernatant.

The anti-DCIR rAbs encoded a ~9.5 kDA dockerin domain in-frame with the rAb H chain. The purpose of the dockerin domain (called rAb.Doc) is to permit assembly of specific [rAb.Doc:Coh.antigen] complexes. In this case, Coh.antigen refers to a fusion protein between a ~17.5 kDa cohesin domain and an antigen. High affinity interaction between cohesin and dockerin is used to assemble defined complexes that we have shown deliver antigen to the surface of DC bearing the receptor specificity. For example, the figure below shows [anti-DCIR.Doc:Coh.Flu M1] complexes bound to the surface of human DC (here the Coh.Flu M1 is biotinylated and detected on the cell surface after washing steps). Control rAb.Doc:Coh.Flu M1 complexes (shown in red in the figure below) did not bind any more than the detecting streptavidin-PE reagent alone.

Figure 11:
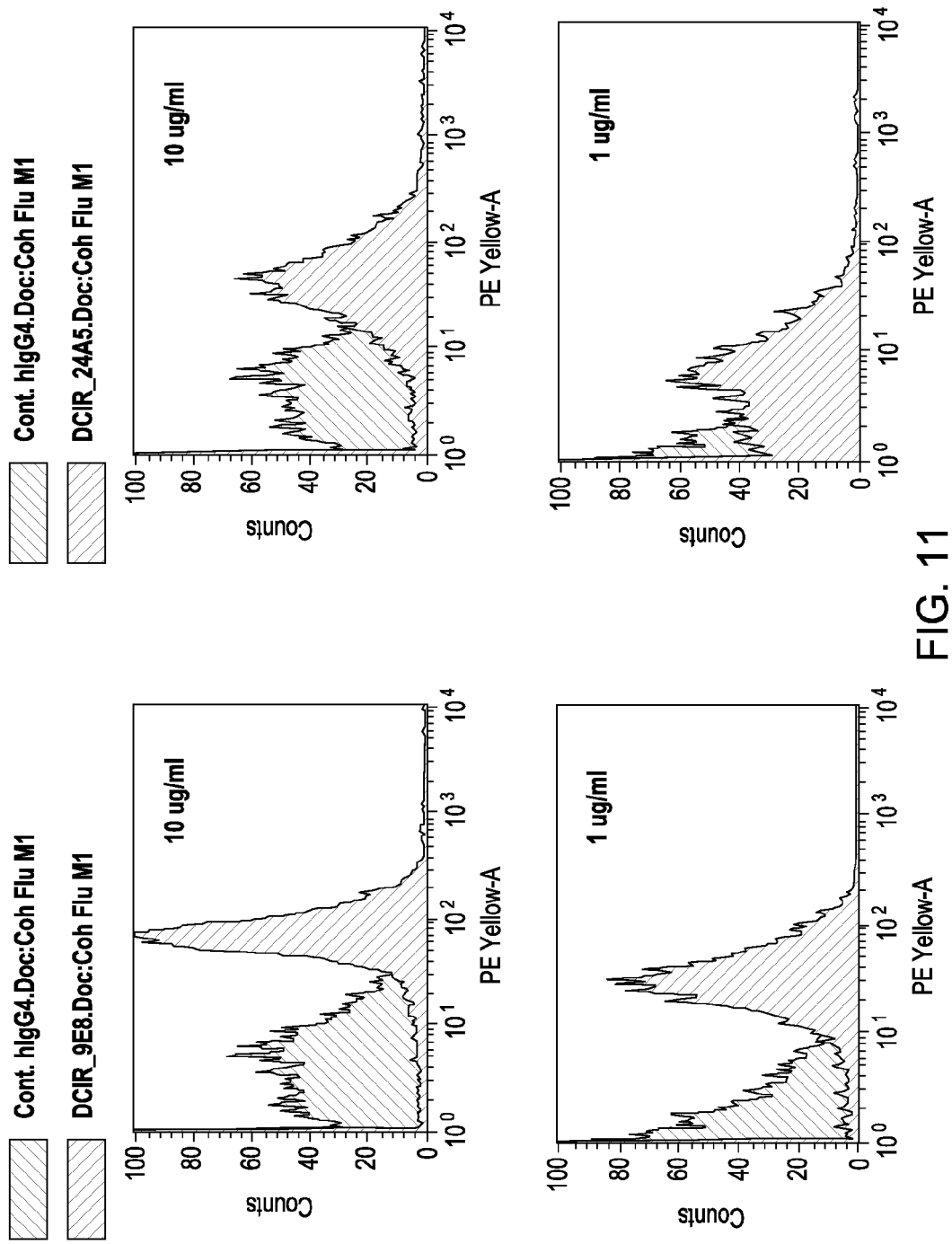
FIG. 11 shows that Coh.Flu M1 linked to anti-DCIR.Doc rAb binds specifically to GM/IL-15 human DC.

DCIR internalizes antigen with slow kinetics and this distinguishes it from other DC receptors. DC receptors such as DC-SIGN are characterized by a rapid kinetics of internalization. For example, FIG. 11 shows that anti-DC-SIGN/L.Doc internalizes Alexa-labeled Coh.Flu M1 into GM-CSF/IFN cultured human DC rapidly—most of the label is internal to the cells within 15 min. In contrast, anti-DCIR.Doc internalizes the Coh.Flu M1 very slowly—at 3 hours there is both significant amounts of internal antigen and of cell-surface antigen. This result distinguishes DCIR as a slow-internalizing DC receptor and is in contrast to the conclusions of Bates et. al., who suggested that "Following cross-linking, DCIR was only slowly and weakly internalized in monocyte- and CD34-derived DC, in contrast to the rapid kinetics observed with the MMR (data not shown). This finding suggests that Ag capture by receptor-mediated endocytosis is not the principal function of DCIR".

FIG. 11 shows that Coh.Flu M1 linked to anti-DCIR.Doc rAb binds specifically to GM/IL-15 human DC. Monocyte-derived GM-CSF/IL-15 cultured human DCs were incubated with the indicated concentrations of anti-DCIR.Doc rAbs premixed for 1 hour with a 4-fold molar excess of biotinylated Coh.Flu M1. After 1 hour, cells were washed and incubated with streptavidin-PE. After another wash, the cells were analyzed by FACS to detect cell-associated PE. Green plots are the Anti-DCIR.Doc rAbs, red curves are control IgG4.Doc complexes.

Figure 12:
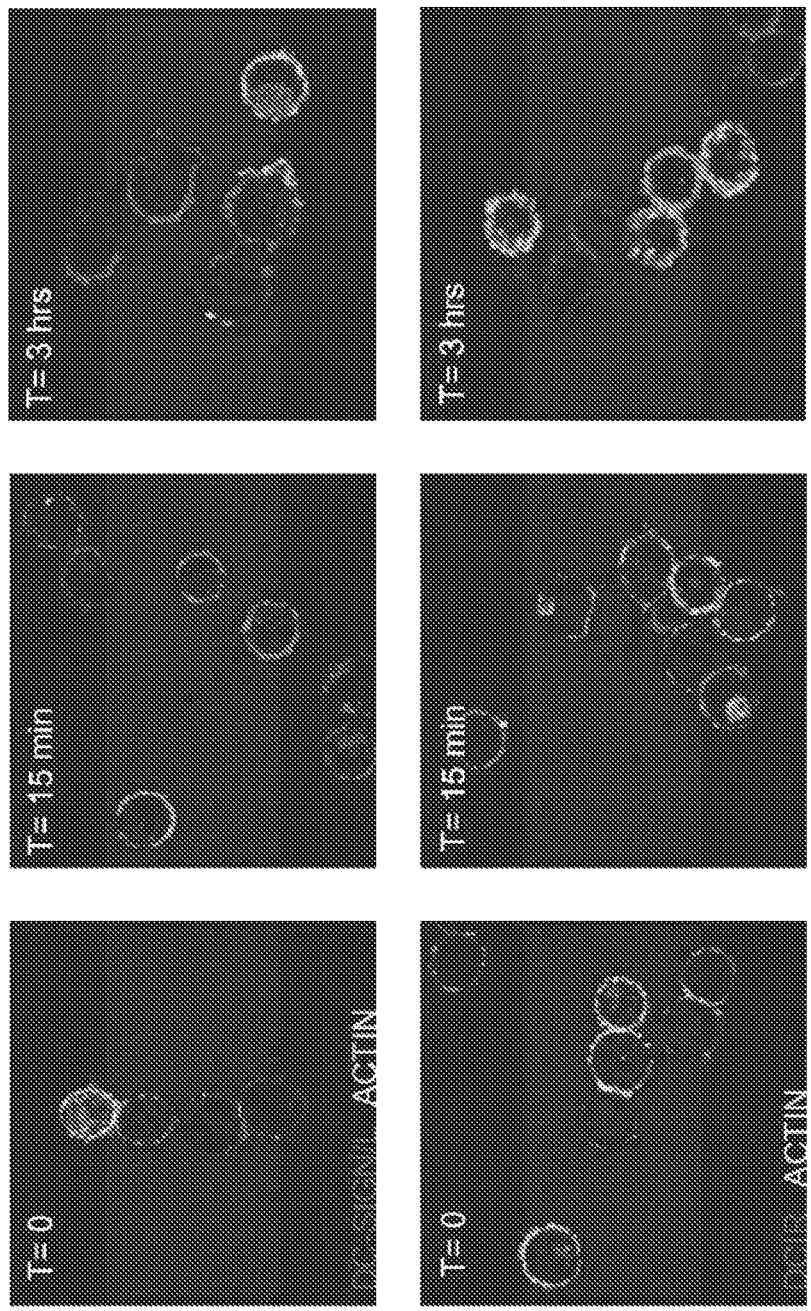
FIG. 12 shows that the Coh.Flu M1 linked to anti-DC-SIGN/L.Doc or anti-DCIR.Doc rAb binds and is internalized into to GM-CSF/IL-4 human DC.

FIG. 12 shows that the Coh.Flu M1 linked to anti-DC-SIGN/L.Doc or anti-DCIR.Doc rAb binds and is internalized into to GM-CSF/IL-4 human DC. Monocyte-derived GM-CSF/IL-4 cultured human DCs were incubated with anti-DCIR.Doc or anti-DC-SIGN/L.Doc rAb premixed for 1 hour with a 4-fold molar excess of Alexa-labeled Coh.Flu M1. After 1 hour on ice, cells were washed and placed at 37 C. Confocal microscopy was used to analyze the cellular location of cell-associated antigen (shown in red). Green marks cell membrane-associated actin.

Targeting Coh.Flu M1 to human DC via DCIR.Doc identifies DCIR as a superior receptor for vaccine development purposes. Targeting Flu M1 antigen to human DC via the slow-internalizing DCIR receptor was compared to targeting via fast-internalizing ASGPR and LOX-1 receptors. The immune response monitored was expansion of Flu M1-specific CD8+ T cells. The results show targeting through DCIR is significantly more efficacious than via LOX-1 or ASGPR. In a similar experiment, the superiority of targeting via DCIR was even more evident when the DC were washed free of residual [rAb.Doc:Coh.antigen] before culture with the CD8+ T cells. This situation is likely closer to the in vivo situation, where targeted DC would move away from residual administered antigen to encounter T cells in draining lymph nodes.

Figure 13:
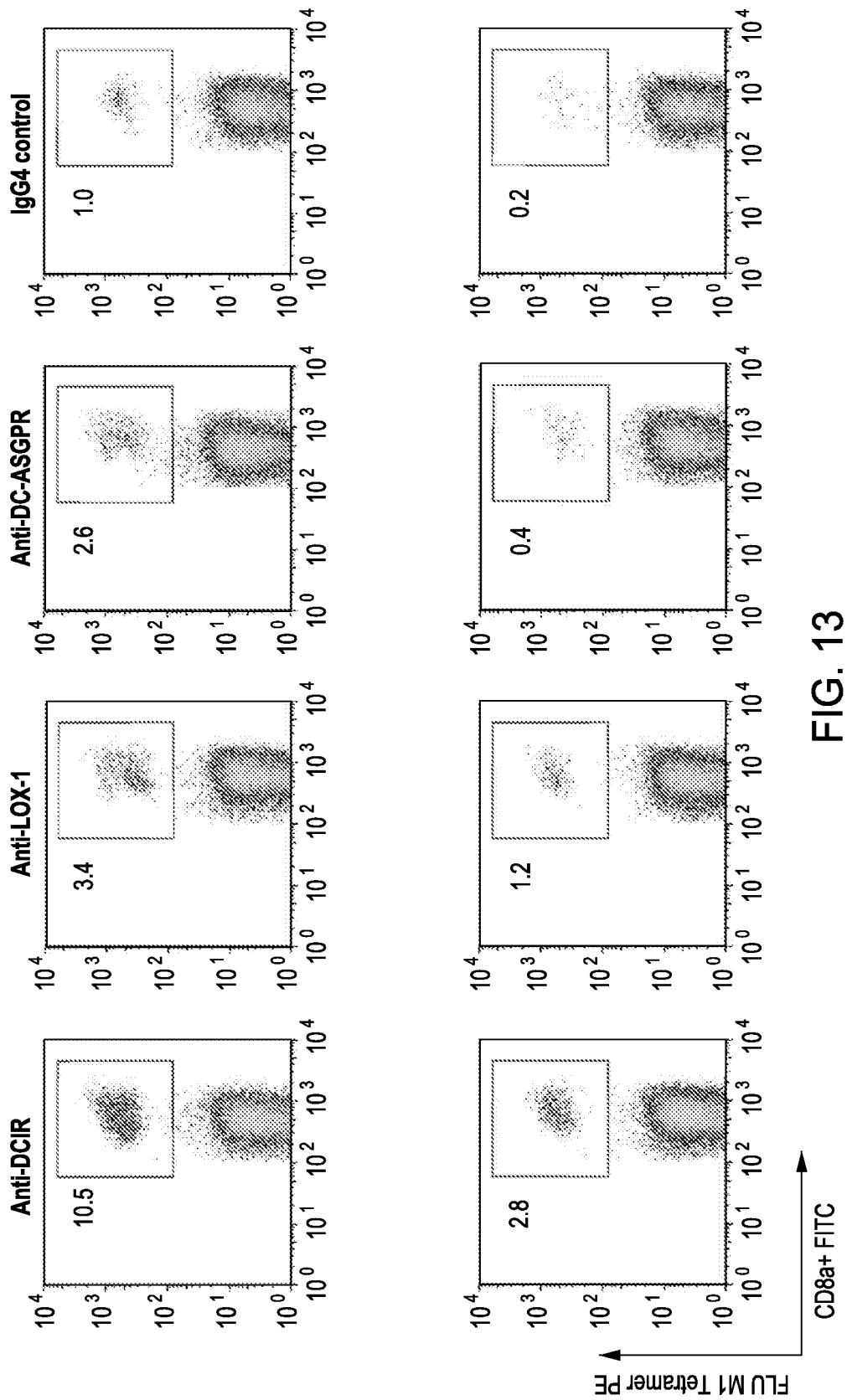
FIG. 13 shows that the Anti-DCIR.Doc:Coh.Flu complex is more efficient at expanding Flu M1-specific CD8+ T cells than other [anti-DC receptor rAbs.Doc:Coh.Flu M1] complexes.

FIG. 13 shows that the Anti-DCIR.Doc:Coh.Flu complex is more efficient at expanding Flu M1-specific CD8+ T cells than other [anti-DC receptor rAbs.Doc:Coh.Flu M1] complexes. CD34-derived CD1a+ DCs, were co-cultured with CD8+ T cells and 8 nM (top panel) or 0.8 nM (lower panel) of [anti-DCIR_2C9.Doc:Coh.Flu M1], anti-LOX1_15C4.Doc, anti-ASGPR_49C11.Doc or IgG4.Doc control rAb, each complexed with Coh.Flu M1. CD8+ T cells were then analyzed for Flu M1-specific expansion. The inner boxes indicate the percentages of tetramer-specific CD8+ T cells.

Figure 14:
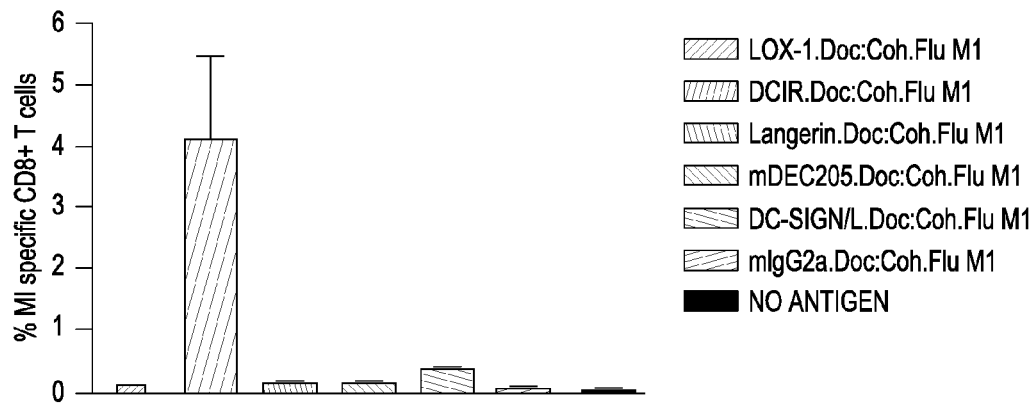
FIG. 14 shows that the Anti-DCIR.Doc:Coh.Flu complex administered for 1 day is more efficient at expanding Flu M1-specific CD8+ T cells than other [anti-DC receptor rAbs.Doc:Coh.Flu M1] complexes.

FIG. 14 shows that the Anti-DCIR.Doc:Coh.Flu complex administered for 1 day is more efficient at expanding Flu M1-specific CD8+ T cells than other [anti-DC receptor rAbs.Doc:Coh.Flu M1] complexes. Study conditions were as for the figure above, expect DC were washed at day 1 prior to addition of autologous CD8+ T cells. Some anti-DCIR V regions are particularly favorable to secretion of important antigens fused at the rAb H chain C-terminus.

Figure 15:
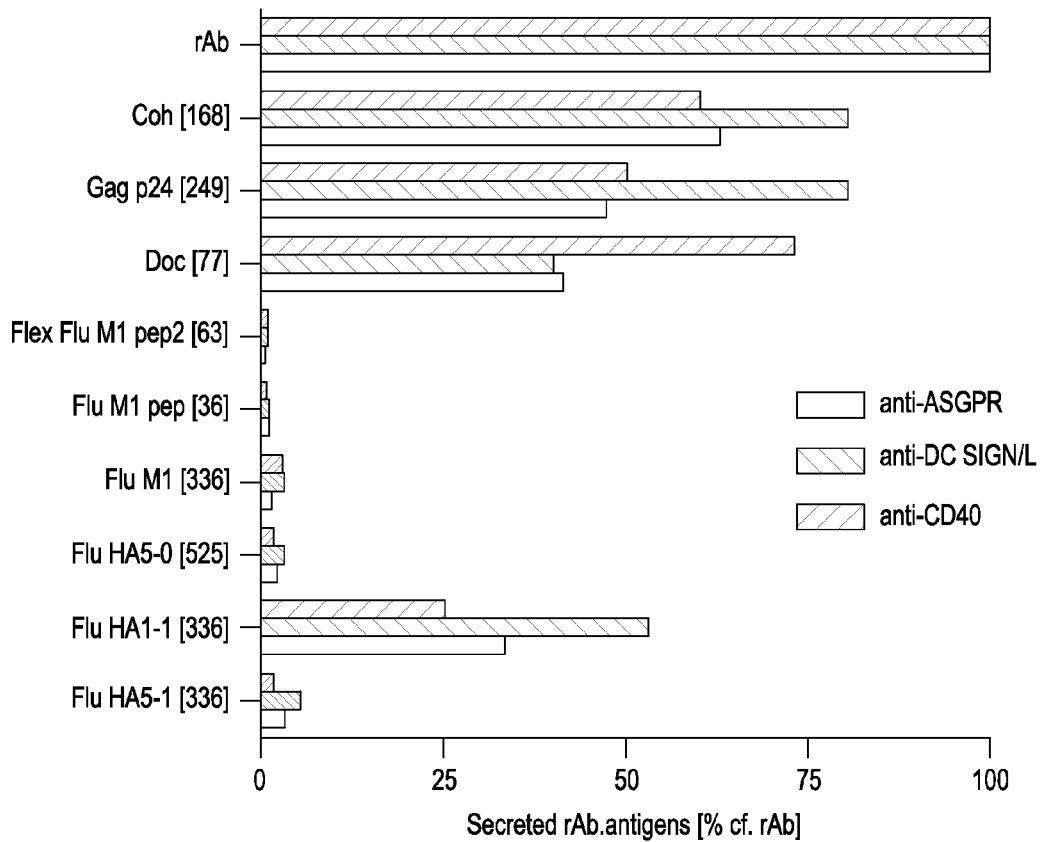
FIG. 15 sh example, simple intermediary metabolites, sugars, lipids and hormones as well as macromolecules such as complex carbohydrates, phospholipids, nucleic acids and proteins. Common categories of antigens include, but are not limited to, viral antigens, bacterial antigens, fungal antigens, protozoal and other parasitic antigens, tumor antigens, antigens involved in autoimmune disease, allergy and graft rejection, and other miscellaneous antigens.

FIG. 15 shows that various antigens expressed as fusions to the C-terminus of rAb H chain have intrinsic effects on the secretion of rAb.antigen. Here identical antigen coding regions were engineered on chimeric hIgG4 rAbs with two different mouse V region specificities. These expression constructs were co-transfected with appropriate L chain mouse V-region—hIgk constructs into 293F cells and secretion of rAb was appraised after three days. Some rAb antigens were well expressed, others (including Flu HA5-1) very poorly. It should be expected that each antigen has intrinsic biochemical properties affecting secretion in the context of rAb. Indeed there is a strikingly parallel effect on expression in the context of the two V region specificities tested.

Figure 16:
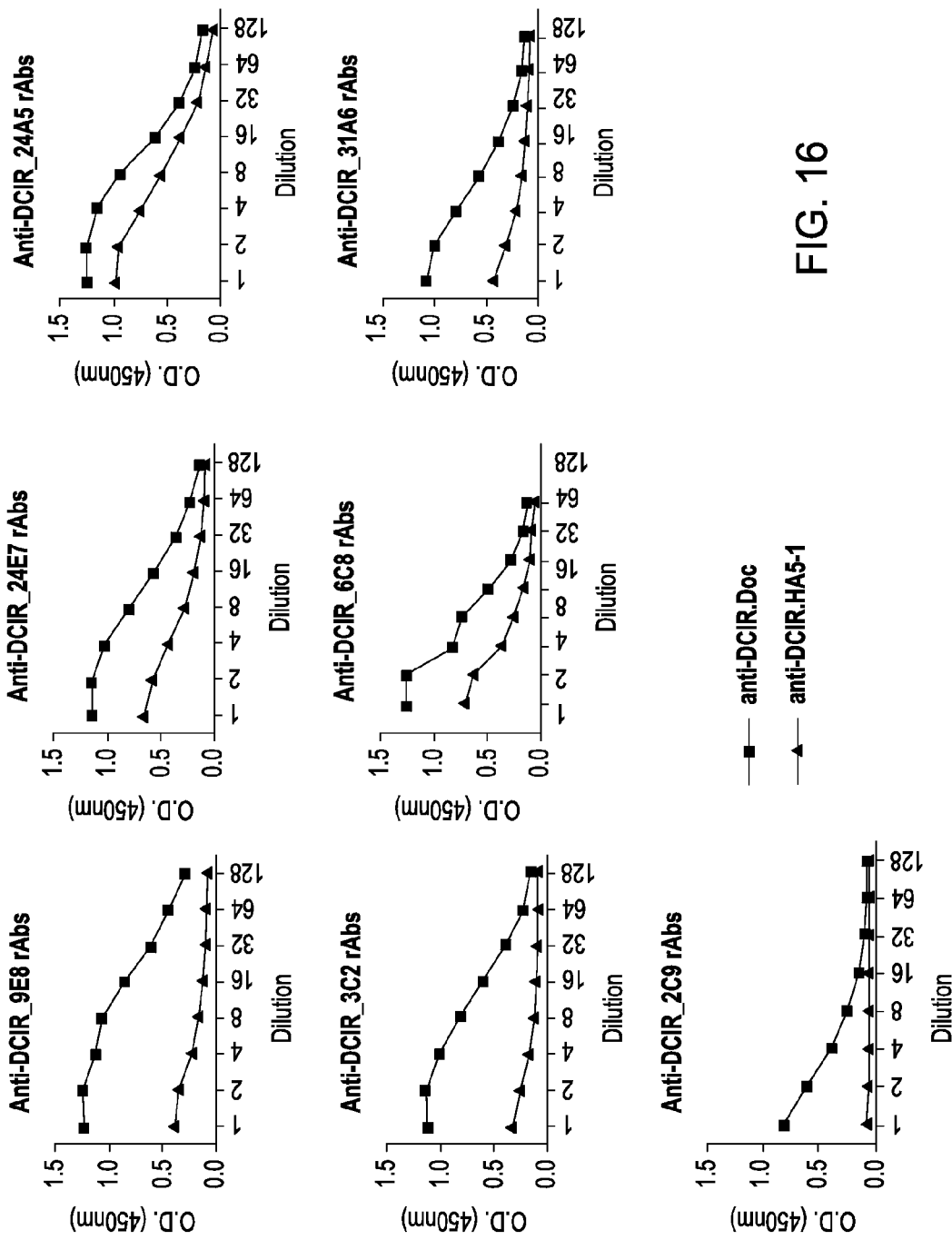

Flu HA5 is an antigen that is important to consider in development of a vaccine against avian influenza. FIG. 16 shows the unexpected discovery that different anti-DCIR V regions (derived from different anti-DCIR mAbs) greatly affect secretion of the desired anti-DCIR.Flu HA5 vaccine. In the example shown below, DCIR_25A4 is particularly favorable for secretion of this type of vaccine when compared to other DCIR V regions.

FIG. 16 shows the Anti-DCIR.Flu HA5 rAbs are secreted at various efficiencies depending on the nature of the variable regions. H and L chain expression plasmids encoding chimeric mouse V region and human C region fused via the H chain C-terminus to either Doc (Blue circles) or HA5-1 (Red triangles) were co-transfected into 293 cells and after 3 days dilutions of the supernatants were assayed for IgGFc by ELISA. Except for DCIR_2C9, rAb.Docs were generally well expressed. However, expression of rAb.HA5-1s varied widely.

The unique property of the anti-DCIR 25A4 V-regions to favor secretion of rAb.HA5-1 illustrates application of claim 5. That is based on our invention that a particular V-region can affect secretion of a rAb.antigen. This means that intrinsic poor secretion of a particular antigen in the context of a rAb fusion protein can be overcome by screening different V regions with the desired combining specificities for those favorable for secretion. This is claimed as a new general principle for any secreted rAb.fusion protein.

Figure 17:
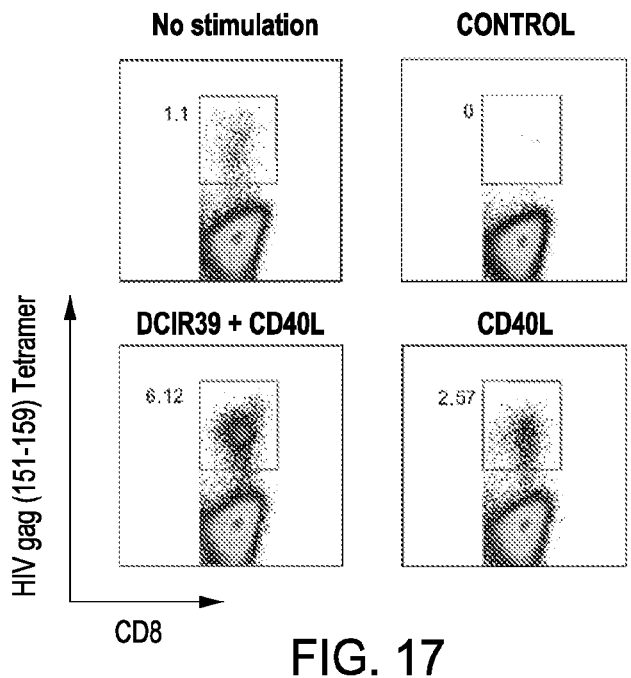

Anti-DCIR enhances priming of HIV specific CD8+ T cells. FIG. 17 shows that anti-DCIR mAb has a particular action on dendritic cells that enhances priming—that is the uptake of peptide and its presentation on surface MHC to T cells specific to the peptide antigen. The example shows that stimulation of DC with anti-DCIR mAb together with CD40L, a known DC activation signal usually delivered by cognate T cells, resulted in greatly increased numbers of CD8+ T cells specific to the immunodominant HIV gag peptide that was added to the DC culture. This property is highly predictive for successful antigen targeting via anti-DC receptor rAb vaccines and indicates that anti-DCIR.antigen vaccines will be superior.

FIG. 17 shows that Anti-DCIR mAb enhances priming of HIV antigen-specific CD8$^+$ cells. Purified total CD8$^+$ T cells ($2\times10^6$ cells/well) were stimulated with autologous IFN-DCs ($1\times10^5$ cells/well) and HLA-A201-restricted HIV peptides pol (pol$_{476-484}$ ILKEPVHGV (SEQ ID NO.: 54), pol$_{293-302}$ KYTAFTIPSI (SEQ ID NO.: 55)), and gag (gag$_{77-85}$, SLYNTVATL (SEQ ID NO.: 56), gag$_{151-159}$, TLNAWVKVV (SEQ ID NO.: 57)) (5 μM). Cells were cultured for 9 days in 24 well plates that were pre-coated over night at 4c with 5 ug/well Anti-DCIR mAbs or control monoclonal antibodies diluted in PBS pH9.6 and washed extensively. Cells were cultured in Yssel's medium supplemented with 10% human AB serum, 10 U/ml IL-7 (R&D) and 100 ng/ml CD40L (R&D). IL-2 was added at 10 U/ml at day 3. Expansion of peptide-specific CD8$^+$ T cells was determined by counting the number of cells binding peptide/HLA-A201 tetramers (Beckman Coulter) at the end of the culture period.

Figure 18:
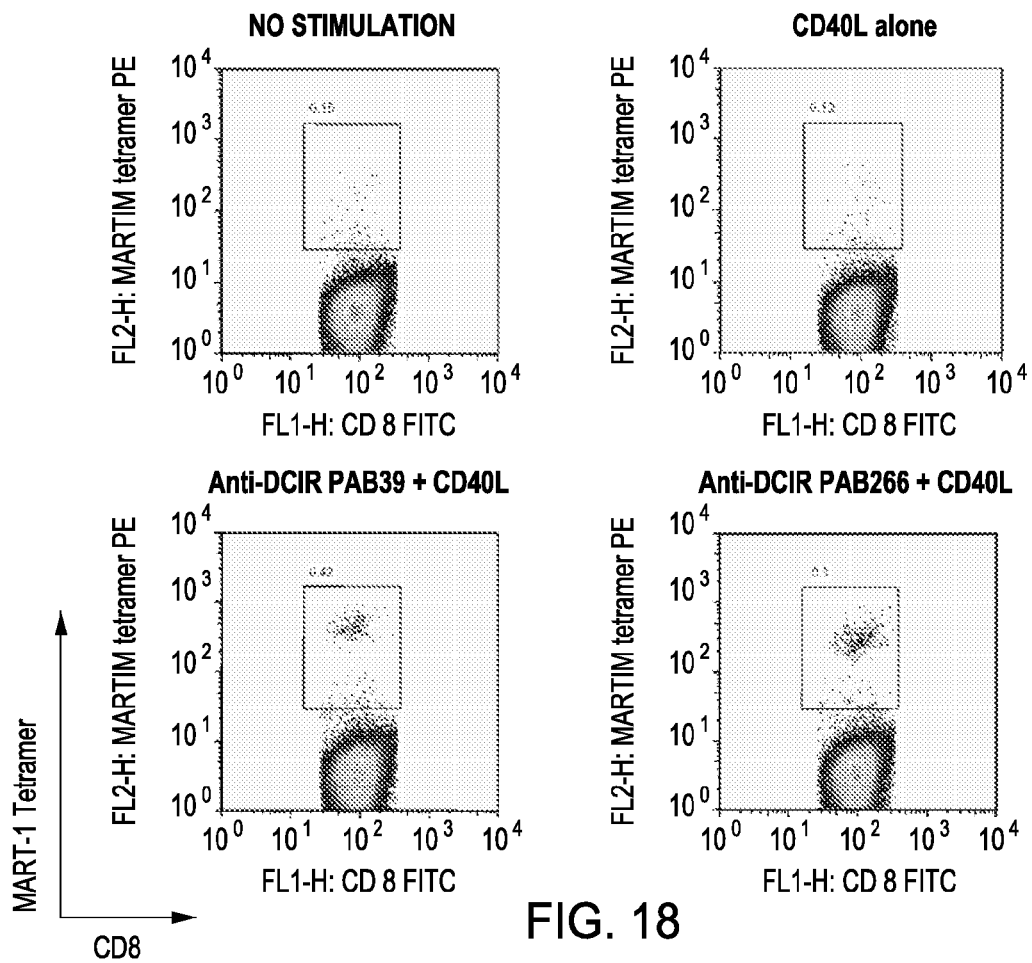

Anti-DCIR mAb enhances cross priming. FIG. 18 shows that anti-DCIR mAb has a particular action on dendritic cells that enhances cross-priming—that is the uptake of protein and its correct processing and presentation on surface MHC as measured by expansion of T cells specific to the antigen-derived peptide. The example shows that stimulation of DC with anti-DCIR mAb together with CD40L, a known DC activation signal usually delivered by cognate T cells, resulted in greatly increased numbers of CD8+ T cells specific to the immunodominant MART-1 epitope from the Cohesin-MART-1 fusion protein that was added to the DC culture. This property is highly desirable for antigen targeting via anti-DC receptor rAb vaccines and indicates that anti-DCIR-.antigen vaccines will be superior.

FIG. 18 shows the Anti-DCIR mAb enhances priming of HIV antigen-specific CD8+ cells. Above Figure method as for the previous figure, except that coh.MART-1 peptide fusion protein replaced peptide.

It is contemplated that any embodiment discussed in this specification can be implemented with respect to any method, kit, reagent, or composition of the invention, and vice versa. Furthermore, compositions of the invention can be used to achieve methods of the invention.

Figure 19:
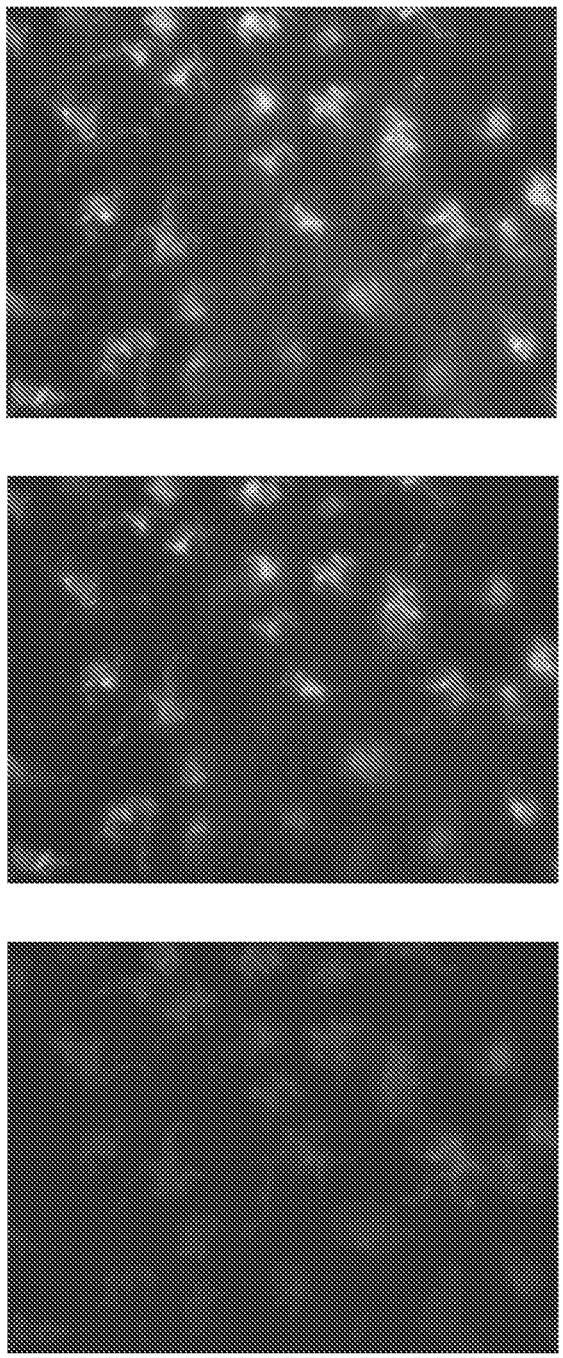
Figure 20A:
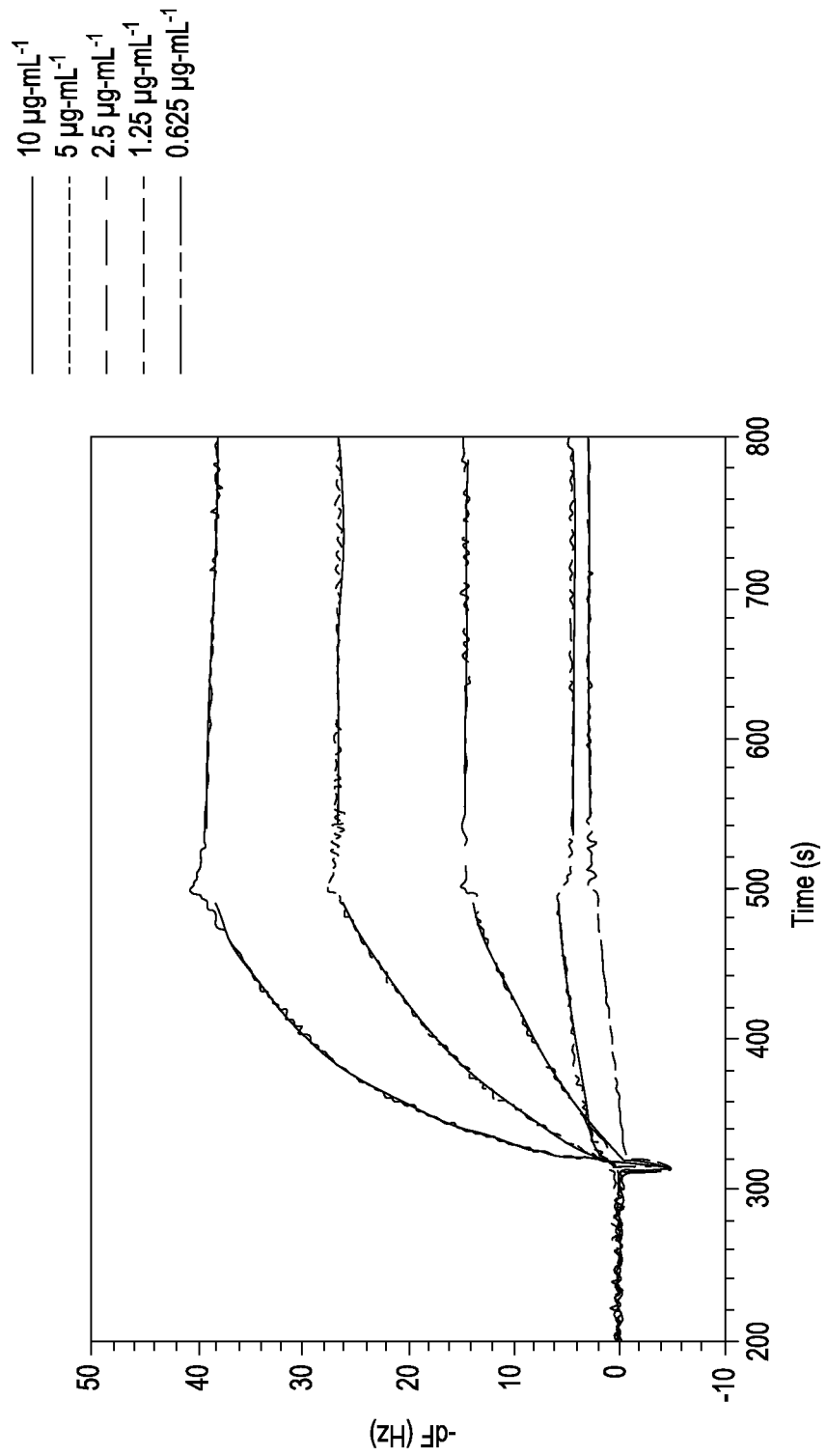
Figure 20B:
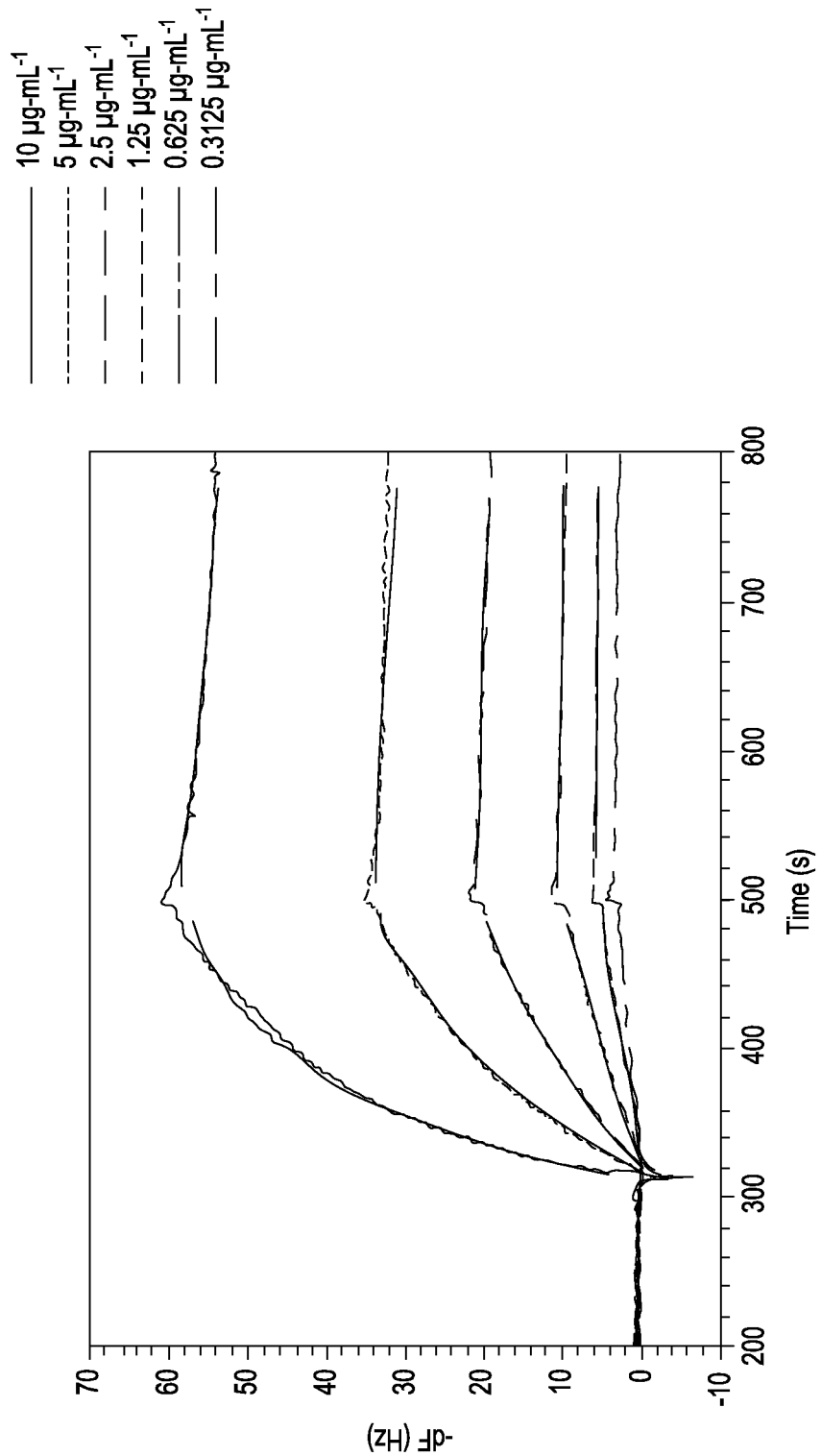
Figure 20C:
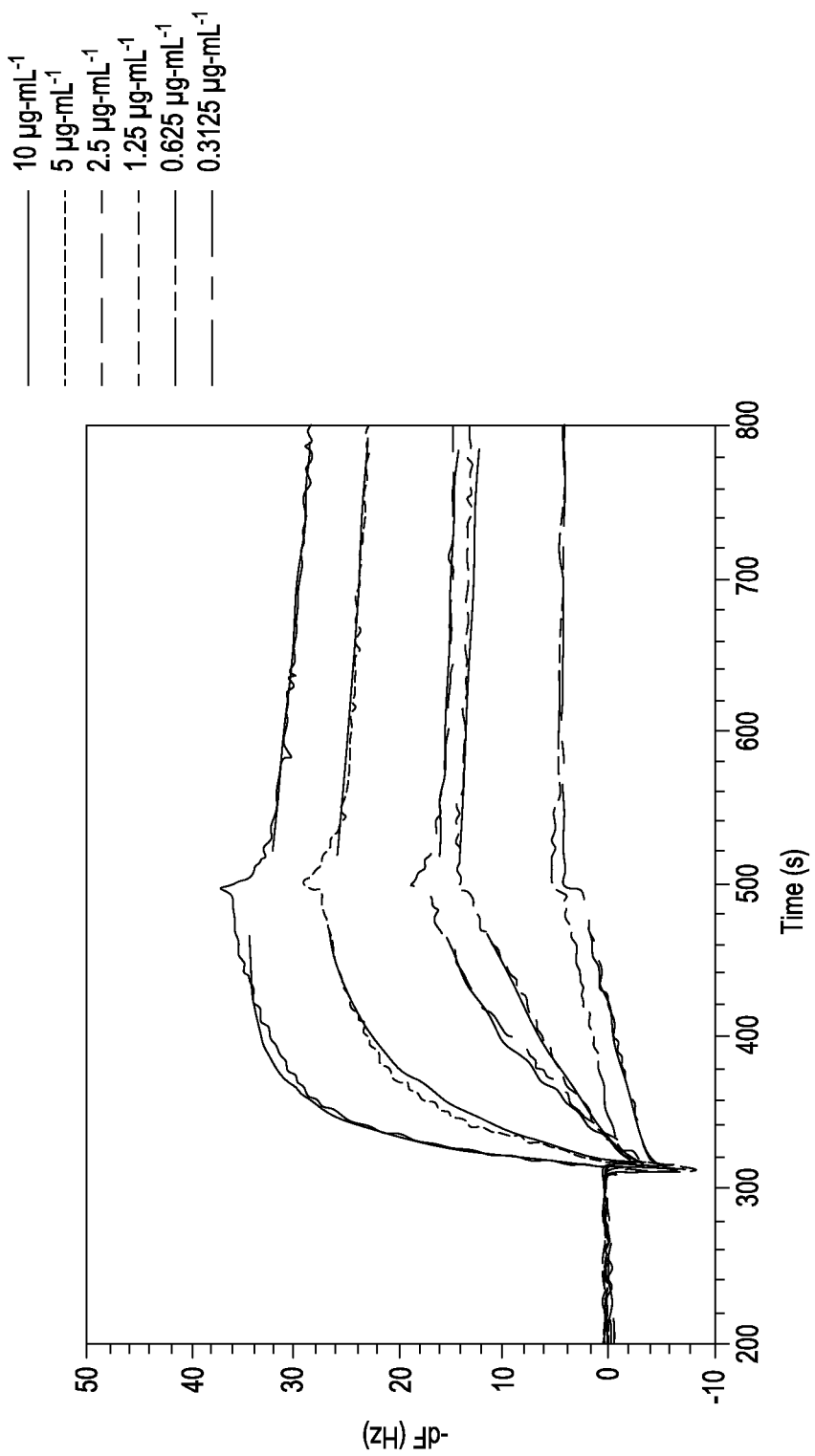
Figure 20D:
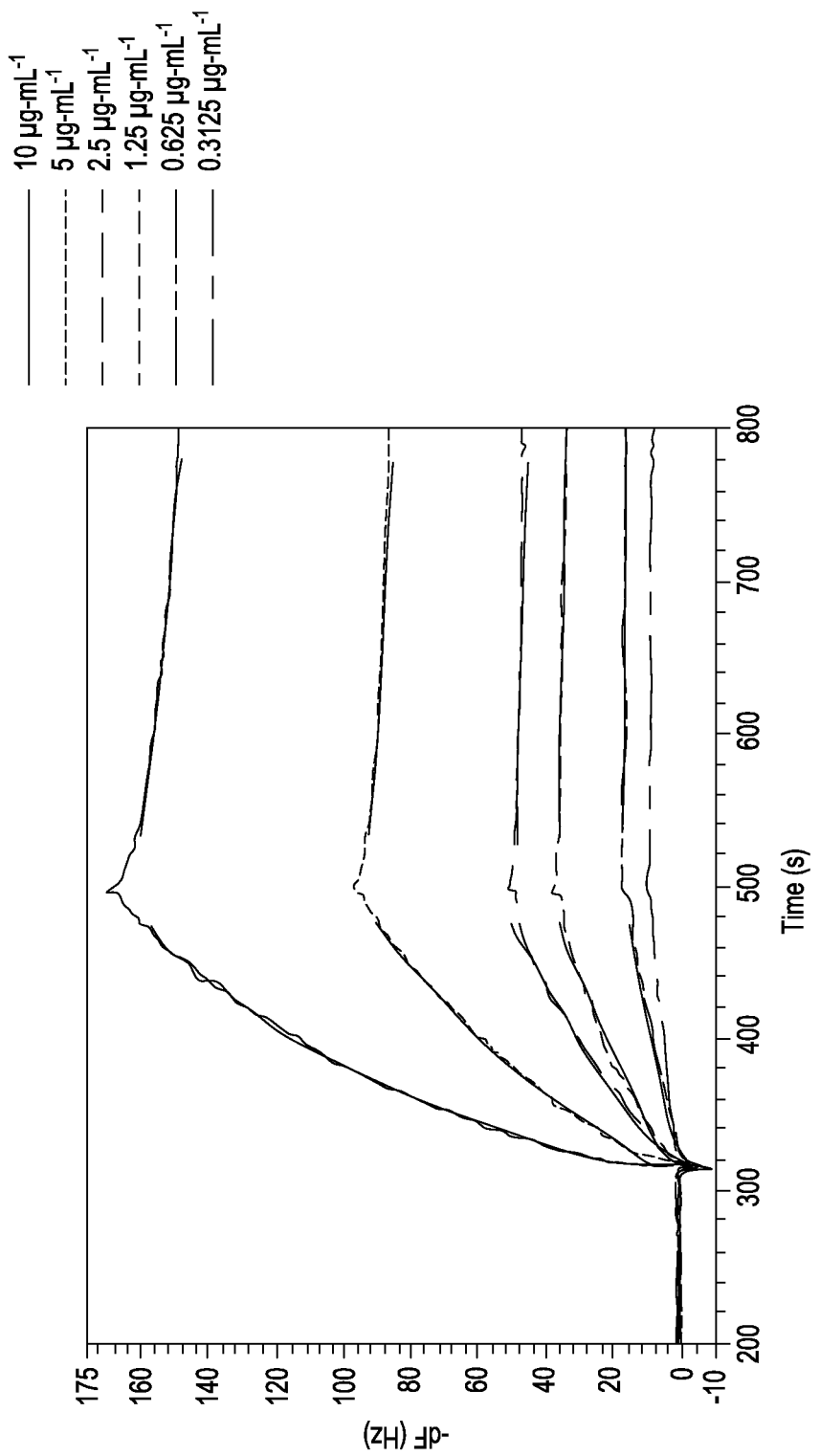

FIG. 19 shows an immunohistochemistry analysis of DCIR distribution in human epithelial sheet. DR-FITC staining is shown in green and PAB269 (DCIR)-568 is shown in red. The upper right panel shows the images superimposed. Blue staining is DAPI for cell nuclei. Digital imaging @ 40×. The cell morphology and DR staining is characteristic of epidermal Langerhans cells—thus, the analysis reveals DCIR expression on Langerhans cells—pointing to the utility of DCIR to uptake anti-DCIR.antigen conjugate applied to e.g. scarified skin. Therefore, these data shows that Langerhans cells uptake of antigen associated with DC activation via adjuvant will result in potent cellular responses against the targeted antigen.

FIGS. 20A-20D shows monoclonal antibodies to DCIR Antigen, specifically, affinity to DCIR.

Immobilization of DCIR Antigen:

DCIR antigen was immobilized onto AKT_iv covalent sensor surfaces via the primary amines (50 ug·mL-1 in 10 mM sodium acetate, pH 5.5). The carboxylate surfaces were activated using a mixture of EDC and NHS and DCIR was coupled to all four channels. Finally, any remaining carboxylate groups were deactivated using a proprietary blocking agent.

Determination of Affinities of Four Anti-DCIR Antibodies in HBS:

To determine the affinities of four anti-DCIR antibodies, dilution series of each antibody were prepared from 10 to 0.3125 μg mL-1 and injected in parallel over immobilized DCIR antigen for 180 s. Between sample injections the surfaces were regenerated using two 60 s injections of 100 mM hydrochloric acid. Biosensor measurements were performed on an Akubio acoustic biosensor.

TABLE 1

Kinetic Parameters calculated from the interaction of four monoclonal antibodies with immobilized DCIR antigen.

| Antibody | $k_a$ ($M^{-1}s^{-1} \times 10^5$) | $k_d$ ($s^{-1} \times 10^{-4}$) | $K_D$ (pM) |
|---|---|---|---|
| Hybridoma Anti-DCIR24A5.4A5 | 2.07 | 1.15 | 560 |
| rAb Anti-DCIR24A5.4A5.DocVar1 C377 | 2.38 | 3.26 | 1370 |
| Hybridoma Anti-DCIR29E9.2E2 | 5.56 | 4.70 | 850 |
| rAb Anti-DCIR29E9.2E2.DocVar1 C409 | 1.50 | 2.90 | 1940 |

Table 1 shows the high affinity DCIR ectodomain binding properties of two preferred anti-DCIR monoclonal antibodies 24A5 and 9E8 and demonstrate that the derived mouse variable regions, when grafted onto a human IgG4 body, largely retain the high affinity binding properties. This data supports the specific claim to the sequences [and their 'humanized' derivatives] of these variable regions regards utility for binding to human DCIR.

Cross-reactivity of anti-DCIR mAbs to Rhesus macaque DCIR. To test the cross-reactivity of anti-human DCIR mAbs to Rhesus macaque DCIR, 233F cells were transfected with Rhesus macaque DCIR cDNA configured into a mammalian expression vector. The panel of anti-human DCIR antibodies was tested via FACS for binding to monkey DCIR compared to untransfected 293F cells and 293F cells transfected with an identical vector directing the expression of human DCIR. A comparison between the human and monkey DCIR sequences is shown below. Those antibodies showing cross-reactivity between human and monkey DCIR are particularly preferred since, when configured e.g., as recombinant humanized anti-DCIR.antigen vaccine, as a therapeutic agent, NHP toxicity studies can also address mechanism-based issues [i.e., these testes can also address efficacy relative to toxicity].

Human vs. Monkey DCIR. The primary sequence show is human and changes seen in monkey DCIR are shown below the human sequence. The putative transmembrane region is highlighted in underlined. Non-conservative changes are shown highlighted in bold.

(SEQ ID NO.: 58)
MTSEITYAEVRFKNEFKSSGINTASSAASKERTAPHKSNTGFPKLLCAS<u>LLIFFLLLAISFFI</u>

<u>AFVIFFQKYSQLLEKKT</u>

MTSEITYAEV (SEQ ID NO.: 59)
RQNESKSSGIDSASSAASKKRTAPHKSNTGFSKLLCAS<u>LMIFFLLLAISFFFAFFIFFQKYS</u>

<u>QLLEKMT</u>

(SEQ ID NO.: 60)
TKELVHTTLECVKKNMPVEETAWSCCPKNWKSFSSNCYFISTESASWQDSEKDCARME

AHLLVINTQEEQDFIFQNLQEE (SEQ ID NO.: 61)
TKDLVHTTLECVKKNMTTEETAWSCCPKNWKPFSSNCYFISTESASWQKSEKDCARME

AHLLVINTREEQDFIFQNLQEE (SEQ ID NO.: 62)
SAYFVGLSDPEGQRHWQWVDQTPYNESSTFWHPREPSDPNERCVVLNFRKSPKRWGW

NDVNCLGPQRSVCEMMKIHL (SEQ ID NO.: 63)
SAYFVGLSDPEGQRHWQWVDQTPYNESSTFWHPHEPSDPDERCVVLNFRKTPKRWGW

NDVHCIVPQRSVCEMMKIHL

Figure 21:
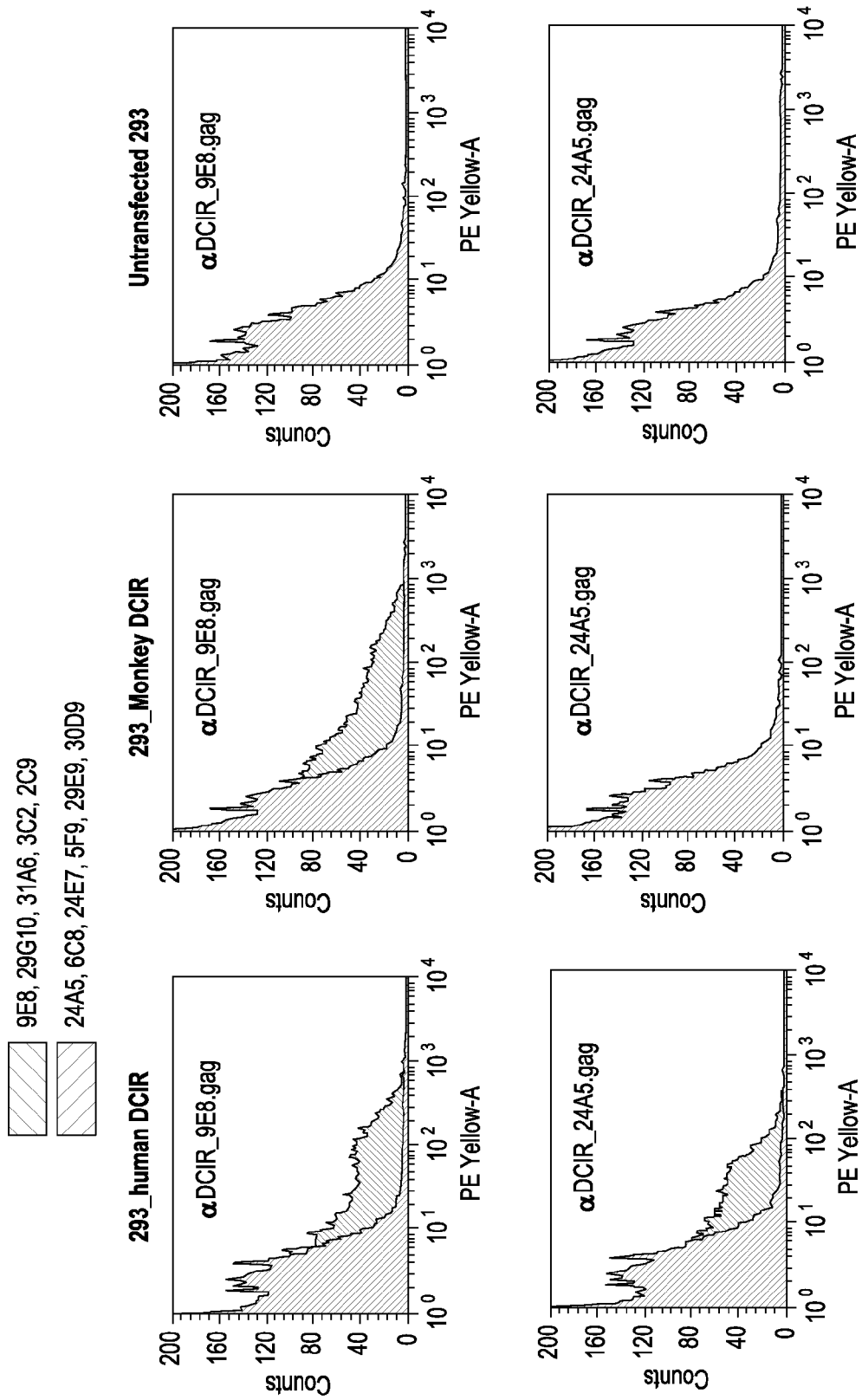

FIG. 21 shows the cross-reactivity of anti-DCIR mAbs to Rhesus macaque DCIR. A sample FACS analysis is presented below. Green plots show the background binding by control IgG4.gag recombinant protein. The red pits are binding via anti-DCIR.gag proteins [secondary antibody was PE-labeled antihuman IgGFc]. The result shows comparable binding by 9E8 and 24A5 mAbs on 293F cells transfected with human DCIR expression plasmid—on 293F cells transfected with monkey DCIR expression plasmid, 9E8, but not 24A5, bound. In a similar analysis mAbs 9E8, 29G10, 31A6, 3C2 bound well to monkey DCIR, but mAbs 24A5, 6C8, 24E7, 5F9, 29E9 did not bind.

Figure 22:
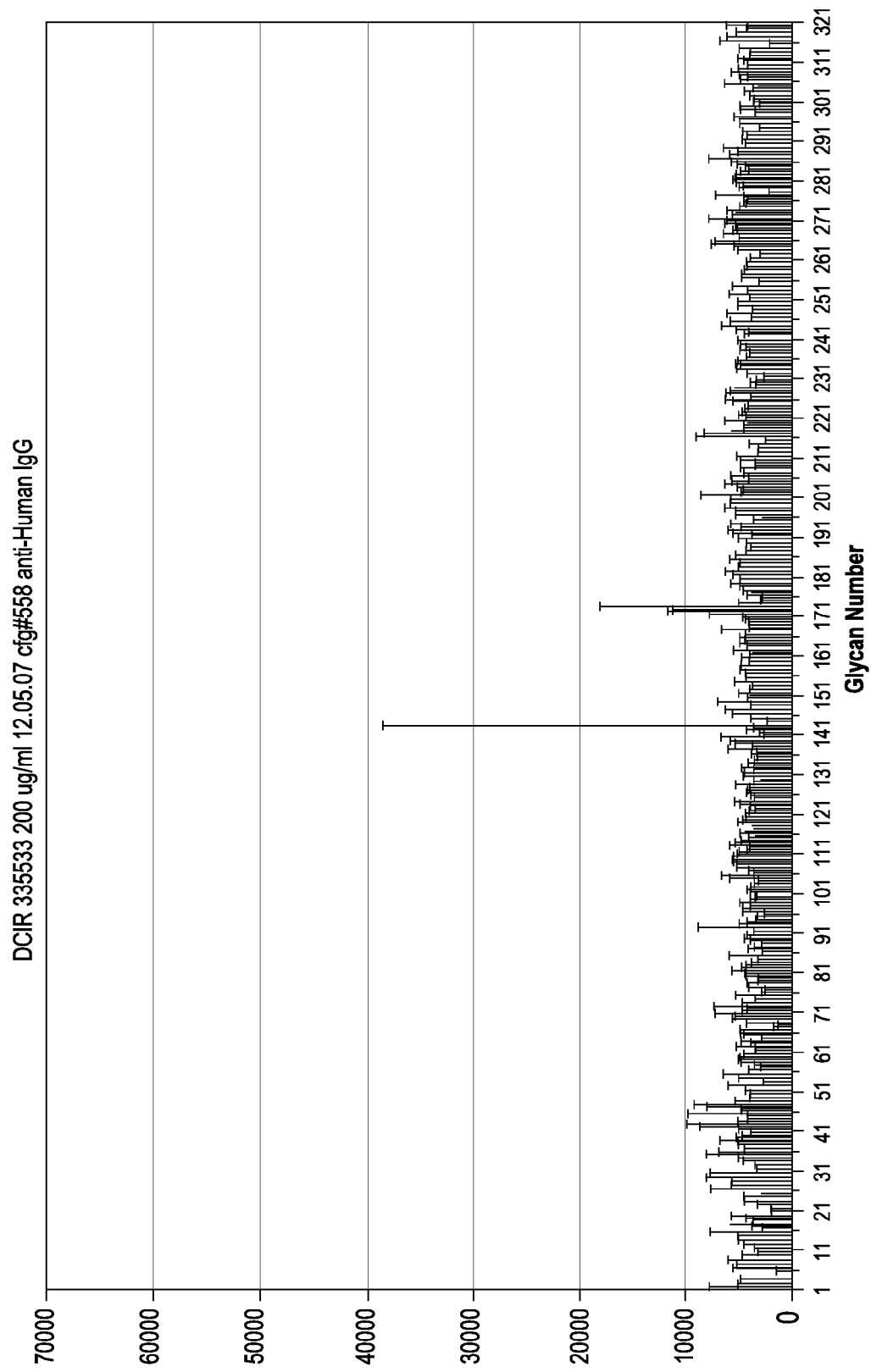

FIG. 22 is a graph that shows the binding of DCIR ectodomain to specific glycan structures. DCIR ectodomain was expressed as a hIgGFc fusion protein secreted from 293F cells and was purified by protein A affinity chromatography. The protein was tested for binding of specific glycans using the version 3.0 of the printed array from the Consortium for Functional Glycomics—this array consists of 320 glycans (or glycoforms) in replicates of 6. The Excel spread sheet shown below presents in columns A-F, respectively, the Glycan number, the structure or name, the average RFU value from the 6 replicates, the standard deviation, the standard error of the mean (used for the error bars in the graph above, which presents the entered data set) and % CV. Columns C-Y contain the graph of glycan number vs. Average RFU, and Columns Z-AE is the data from A-F sorted by RFU (high to low) to provide a list of the Glycans bound with highest intensity. The highest and lowest point from each set of six replicates has been removed so the average is of 4 values rather than 6. This eliminates some of the false hits that contain a single very high point. Thus, points with high % CV should be considered suspect. The analysis was done with detection using anti-human IgG-Fc that was labeled with Phycoerythrin. The DCIR.IgFc was diluted in PBS to 200 μg/ml using Tris-saline binding buffer containing 2 mM Ca and Mg, 1% BSA and 0.05% Tween 20.

This data was generated in collaboration with the Functional Glycomics Consortium. Neu5Acα2-3Galβ1-4GlcNAcβ1-2Manα1-3(Neu5Acα2-3Galβ1-4GlcNAcβ1-2Manα1-6)Manβ1-4GlcNAcβ1-4GlcNAcβ-Sp12 was the glycan which bound DCIR ectodomain most tightly. Other hIgGFc fusion proteins tested did not show a preference for this glycan which is a very complex carbohydrate found on several human serum proteins.

Thus, antigen decorated with glycan 143, or a higher affinity derivative screened from a panel of related structures, should hone the antigen to DCIR and serve as a surrogate for the anti-DCIR component of the DC-targeting vaccine or other DCIR targeting agent. This could have cost benefit in vaccine manufacture and storage.

TABLE 2

| | DCIR.IgGFc @ 200 ug/ml vs. anti-Human IgG PE | | | | |
|---|---|---|---|---|---|
| Glycan number | Glycan name | Avg w/o Max & Min | StDev w/o Max & Min | SEM w/o Max & Min | % CV |
| 143 | Neu5Acα2-3Galβ1-4GlcNAcβ1-2Manα1-3-4GlcNAcβ1-2Manα1-6)Manβ1-4GlcNAcβ1-4GlcNAcβ-Sp12 | 38314 | 2007 | 1004 | 5 |

TABLE 2-continued

DCIR.IgGFc @ 200 ug/ml vs. anti-Human IgG PE

| Glycan number | Glycan name | Avg w/o Max & Min | StDev w/o Max & Min | SEM w/o Max & Min | % CV |
|---|---|---|---|---|---|
| 173 | GlcNAcβ1-4GlcNAcβ1-4GlcNAcβ-Sp8 | 17109 | 1865 | 932 | 11 |
| 172 | (GlcNAcβ1-4)5β-Sp8 | 11161 | 1247 | 624 | 11 |
| 45 | [6OSO3]Galβ1-4[6OSO3]Glcβ-Sp8 | 9762 | 1375 | 688 | 14 |
| 42 | [6OSO3]Galβ1-4Glcβ-Sp0 | 8376 | 3206 | 1603 | 38 |
| 15 | α-Neu5Ac-Sp11 | 8128 | 887 | 443 | 11 |
| 92 | GalNAcβ1-4GlcNAcβ-Sp0 | 8066 | 1278 | 639 | 16 |
| 47 | [6OSO3]GlcNAcβ-Sp8 | 7906 | 2365 | 1183 | 30 |
| 1 | Neu5Acα2-8Neu5Acα-Sp8 | 7738 | 1337 | 669 | 17 |
| 29 | [3OSO3]Galβ1-4(6OSO3)Glcβ-Sp0 | 7572 | 993 | 496 | 13 |
| 30 | [3OSO3]Galβ1-4(6OSO3)Glcβ-Sp8 | 7515 | 538 | 269 | 7 |
| 271 | Fucα1-2[6OSO3]Galβ1-4[6OSO3]Glc-Sp0 | 7400 | 794 | 397 | 11 |
| 216 | Neu5Acα2-3Galβ1-3(6OSO3)GlcNAc-Sp8 | 7334 | 3242 | 1621 | 44 |
| 26 | [3OSO3][6OSO3]Galβ1-4[6OSO3]GlcNAcβ-Sp0 | 7193 | 939 | 470 | 13 |
| 171 | (GlcNAcβ1-4)6β-Sp8 | 7154 | 1358 | 679 | 19 |
| 286 | [3OSO3]Galβ1-4[6OSO3]GlcNAcβ-Sp0 | 7146 | 1267 | 633 | 18 |
| 265 | [3OSO3]Galβ1-4(Fucα1-3)(6OSO3)Glc-Sp0 | 7143 | 571 | 285 | 8 |

*** Glycan #143 is Neu5Acα2-3Galβ1-4GlcNAcβ1-2Manα1-3(Neu5Acα2-3Galβ1-4GlcNAcβ1-2Manα1-6)Manβ1-4GlcNAcβ1-4GlcNAcβ-Sp12.

Figure 23A:
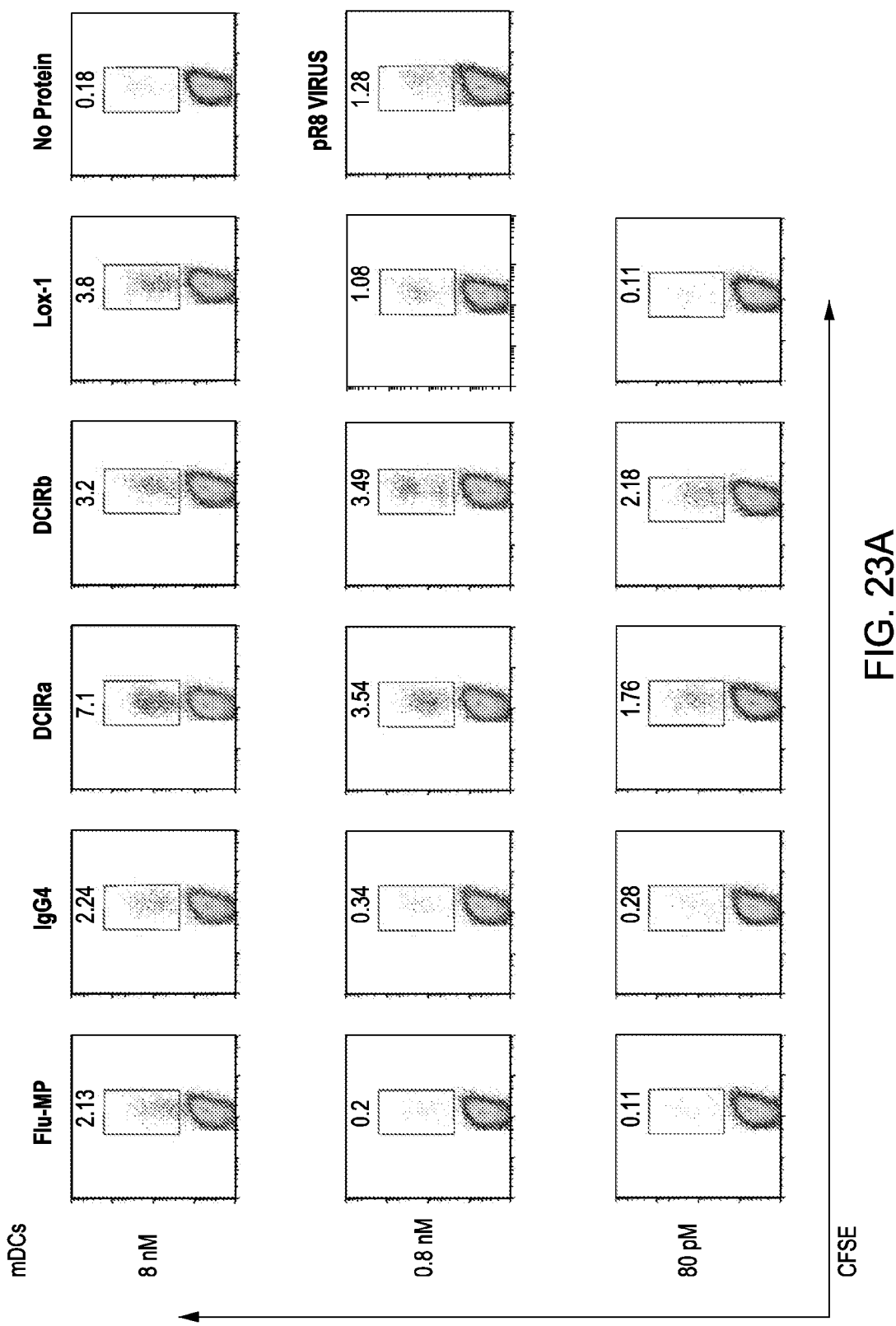
Figure 23B:
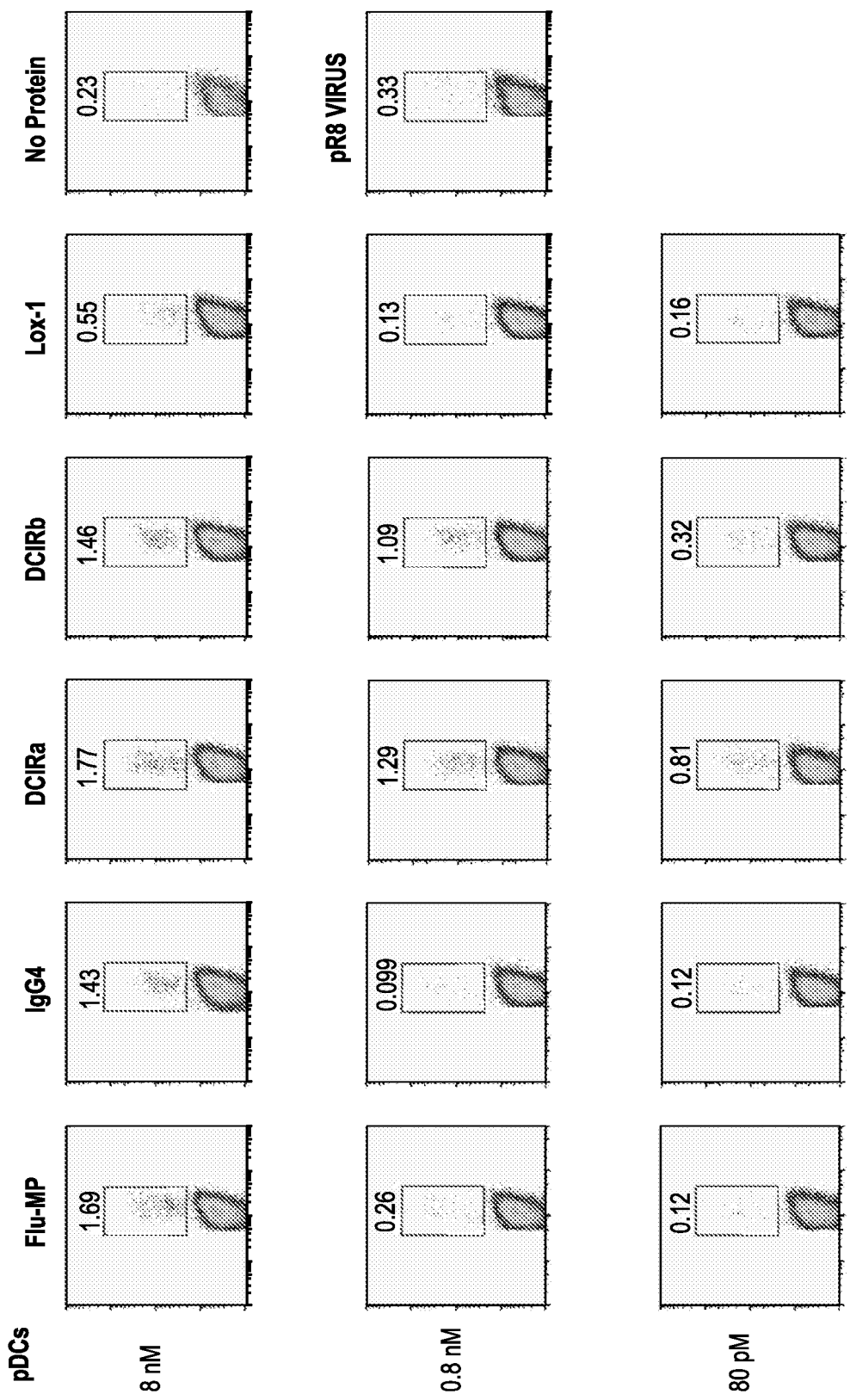
Figure 23C:
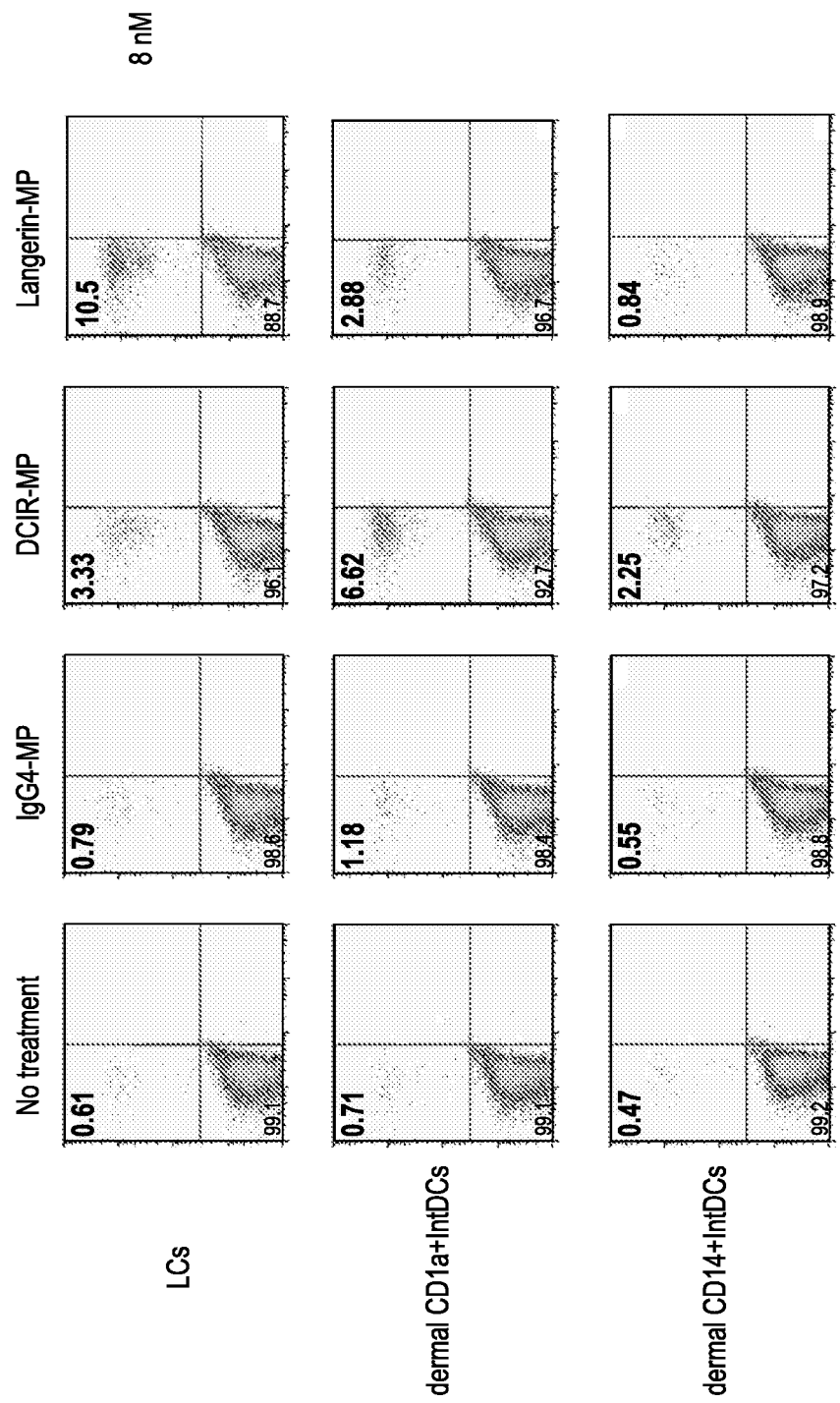

FIGS. 23A to 23C show that DCIR is a global target for all blood DC subsets. Two subsets of DCs are identified in the blood: CD11c+mDCs and BDCA2+pDCs. DCIR is one of the rare lectin-type receptors found on both DC subsets. mDCs and pDCs were purified from cytapheresis and each DC subset was cultured with autologous purified CD8+T cells and decreasing concentrations of four recombinant forms of Flu-MP: Flu-MP, Flu-MP fused to IgG4 and Flu-MP fused to two different recombinant anti-DCIR antibodies: 24A5 and 9E8.

Results shown in FIG. 23A below indicate that both recombinant DCIR-Flu-MP fusion proteins can potently target Flu-MP to mDC as the two proteins can induce between 1.78% and 2.18% tetramer positive cells at a concentration as low as 80 pM, a point where Flu-MP itself and the IgG4-Flu-MP are not able to induce expansion of antigen-specific T cells. pDCs were also able to crosspresent the four forms of recombinant Flu-MP at 8 nM. At 0.8 nM and 80 pM, two DCIR-Flu-MP constructs were crosspresented but the two other Flu-MP constructs were not (FIG. 23B below).

Taken together, these data indicate that DCIR potently target proteins for crosspresentation by both blood mDCs and pDC. In human LCs and IntDCs have capacity to preferentially, respectively, prime cellular immunity and humoral immunity. Targeting antigen to a pan-DC molecule, like DCIR, will potentially induce a wide humoral and cellular immune response by targeting various DC subsets. This is in contrast to a subset-specific antigen-delivery vehicle such as anti-Langerin.

FIG. 23A shows blood-derived mDCs from HLA-A2 donor are targeted with 8 nM, 0.8 nM or 80 pM each of aDCIR-Flu-MP (a#24A5 and b#9E8), IgG4-Flu-MP, or Flu-MP, matured with CD40L and co-cultured with autologous CD8+ T cells. 10 d later, T cell expansion evaluated by specific HLA-A2-M1 tetramer staining [vertical axis].

FIG. 23B shows blood-derived pDCs from HLA-A2 donor are targeted with 8 nM, 0.8 nM or 80 pM each of aDCIR-Flu-MP (a#24A5 and b#9E8), IgG4:Flu-MP, or Flu-MP, matured with CD40L and co-cultured with autologous CD8+ T cells. 10 d later, T cell expansion evaluated by specific HLA-A2-M1 tetramer staining [vertical axis].

FIG. 23C shows DCIR allows crosspresentation of proteins by LCs and dermal CD14+DCs. Skin-derived DC from HLA-A2 donor are targeted with 8 nM each of anti-DCIR:Flu-MP, anti-Langerin:Flu-MP or IgG4:Flu-MP, matured with CD40L and co-cultured with autologous CD8+ T cells. 10 d later, T cell expansion was evaluated by specific HLA-A2-M1 tetramer staining [vertical axis].

Figure 24:
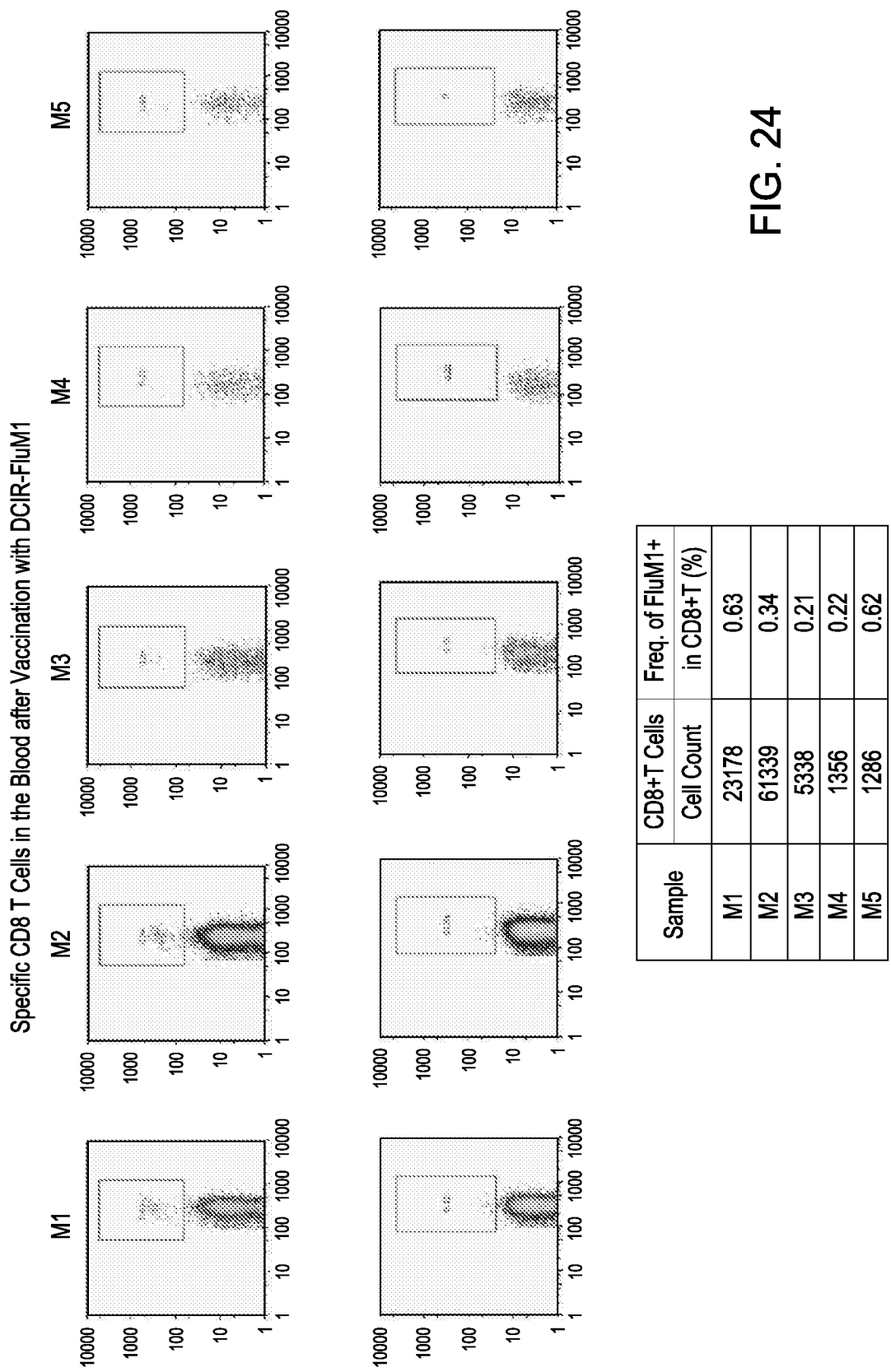

FIG. 24 shows that demonstrate that vaccination with DCIR-FluM1 permits generation of FluM1 specific recall CD8+ T cell immunity. The results from sublethally irradiated NOD/SCID β2m–/– immunodeficient mice were transplanted with 3×106 CD34+ HPCs from HLA-A*0201+ healthy donors, and at 4-8 weeks post transplantation reconstituted by adoptive transfer of 20×106 autologous T cells. Mice were pre-treated for 10 days with five doses of human recombinant FLT3-ligand (FLT3-L) to mobilize DCs. A total of 30 mcg DCIR-FluM1 vaccine was delivered in two sites: i.p. and i.v. at two time points, i.e, day 1 and day 7 with 50 mcg/mouse poly IC as adjuvant. Induction of influenza-specific immune response was assessed by staining blood and tissues with matrix protein 1: FluM158-66 (GILGFVFTL) (SEQ ID NO.: 64) peptide-loaded tetramer. As shown in FIG. 24, 4/5 mice vaccinated with DCIR-FluM1 demonstrated, at day 11 post vaccination, circulating human CD8+ T cells binding FluM1 tetramer: 0.63%, 0.34%, 0.21%, and 0.62%. Staining with control tetramer loaded with HIV gag peptide was nearly negative. These preliminary results were confirmed in independent cohorts of mice and the expansion of high affinity FluM1 tetramer-binding CD8+ T cells was observed in a total of 9/12 vaccinated mice. These results demonstrate that vaccination with DCIR-FluM1 permits generation of FluM1 specific recall CD8+ T cell immunity.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Banchereau, J., F. Briere, et al. (2000). "Immunobiology of dendritic cells." Annu Rev Immunol 18: 767-811.

Banchereau, J., A. K. Palucka, et al. (2001). "Immune and clinical responses in patients with metastatic melanoma to CD34(+) progenitor-derived dendritic cell vaccine." Cancer Res 61(17): 6451-8.

Banchereau, J., B. Schuler-Thurner, et al. (2001). "Dendritic cells as vectors for therapy." Cell 106(3): 271-4.

Bates, E. E., N. Fournier, et al. (1999). "APCs express DCIR, a novel C-type lectin surface receptor containing an immunoreceptor tyrosine-based inhibitory motif." J Immunol 163(4): 1973-83.

Bendtsen, J. D., H. Nielsen, et al. (2004). "Improved prediction of signal peptides: SignalP 3.0." J Mol Biol 340(4): 783-95.

Berard, F., P. Blanco, et al. (2000). "Cross-priming of naive CD8 T cells against melanoma antigens using dendritic cells loaded with killed allogeneic melanoma cells." J Exp Med 192(11): 1535-44.

Bonifaz, L. C., D. P. Bonnyay, et al. (2004). "In vivo targeting of antigens to maturing dendritic cells via the DEC-205 receptor improves T cell vaccination." J Exp Med 199(6): 815-24.

Carvalho, A. L., F. M. Dias, et al. (2003). "Cellulosome assembly revealed by the crystal structure of the cohesin-dockerin complex." Proc Natl Acad Sci USA 100(24): 13809-14.

Cella, M., F. Sallusto, et al. (1997). "Origin, maturation and antigen presenting function of dendritic cells." Curr Opin Immunol 9(1): 10-6.

Delneste, Y., G. Magistrelli, et al. (2002). "Involvement of LOX-1 in dendritic cell-mediated antigen cross-presentation." Immunity 17(3): 353-62.

Figdor, C. G., Y. van Kooyk, et al. (2002). "C-type lectin receptors on dendritic cells and Langerhans cells." Nat Rev Immunol 2(2): 77-84.

Geijtenbeek, T. B., S. J. van Vliet, et al. (2004). "Self- and nonself-recognition by C-type lectins on dendritic cells." Annu Rev Immunol 22: 33-54.

Gerwig, G. J., J. P. Kamerling, et al. (1993). "The nature of the carbohydrate-peptide linkage region in glycoproteins from the cellulosomes of Clostridium thermocellum and Bacteroides cellulosolvens." J Biol Chem 268(36): 26956-60.

Mellman, I. and R. M. Steinman (2001). "Dendritic cells: specialized and regulated antigen processing machines." Cell 106(3): 255-8.

Neidhardt-Berard, E. M., F. Berard, et al. (2004). "Dendritic cells loaded with killed breast cancer cells induce differentiation of tumor-specific cytotoxic T lymphocytes." Breast Cancer Res 6(4): R322-8.

Orban, J., P. Alexander, et al. (1992). "Sequence-specific 1H NMR assignments and secondary structure of the streptococcal protein G B2-domain." Biochemistry 31(14): 3604-11.

Palucka, A. K., J. Gatlin, et al. (2003). "Human dendritic cell subsets in NOD/SCID mice engrafted with CD34+ hematopoietic progenitors." Blood 102(9): 3302-10.

Ramakrishna, V., J. F. Treml, et al. (2004). "Mannose receptor targeting of tumor antigen pmel17 to human dendritic cells directs anti-melanoma T cell responses via multiple HLA molecules." J Immunol 172(5): 2845-52.

Reddy, M. P., C. A. Kinney, et al. (2000). "Elimination of Fc receptor-dependent effector functions of a modified IgG4 monoclonal antibody to human CD4." J Immunol 164(4): 1925-33.

Shortman, K. and Y. J. Liu (2002). "Mouse and human dendritic cell subtypes." Nat Rev Immunol 2(3): 151-61.

Shulman, M., C. D. Wilde, et al. (1978). "A better cell line for making hybridomas secreting specific antibodies." Nature 276(5685): 269-70.

Steinman, R. M. and M. Dhodapkar (2001). "Active immunization against cancer with dendritic cells: the near future." Int J Cancer 94(4): 459-73.

Tacken, P. J., I. J. de Vries, et al. (2005). "Effective induction of naive and recall T-cell responses by targeting antigen to human dendritic cells via a humanized anti-DC-SIGN antibody." Blood 106(4): 1278-85.

Trombetta, E. S, and I. Mellman (2005). "Cell biology of antigen processing in vitro and in vivo." Annu Rev Immunol 23: 975-1028.

Trumpfheller, C., J. S. Finke, et al. (2006). "Intensified and protective CD4+ T cell immunity in mice with anti-dendritic cell HIV gag fusion antibody vaccine." J Exp Med 203(3): 607-17.

What is claimed is:

1. A fusion protein comprising an antigen and a recombinant antibody or fragment thereof that specifically binds to Dendritic Cell Immunoreceptor (DCIR).

2. The fusion protein of claim 1, wherein the antigen comprises a T cell epitope.

3. The fusion protein of claim 1, wherein the fusion protein comprises at least one viral antigen.

4. The fusion protein of claim 1, wherein the fusion protein comprises a flu antigen.

5. The fusion protein of claim 1, wherein the antigen comprises a HIV antigen.

6. The fusion protein of claim 5, wherein the HIV antigen is from a gag, pol or env gene product.

7. The fusion protein of claim 5, wherein the HIV antigen is from a Nef protein or reverse transcriptase.

8. A vaccine composition comprising the fusion protein of claim 1.

9. A vaccine composition comprising the fusion protein of claim 4.

10. A vaccine composition comprising the fusion protein of claim 5.

* * * * *

SEQUENCE LISTING

<160> NUMBER OF SEQ ID NOS: 64

<210> SEQ ID NO 1
<211> LENGTH: 73
<212> TYPE: PRT
<213> ORGANISM: Artificial
<220> FEATURE:
<223> OTHER INFORMATION: Synthetic peptide.

<400> SEQUENCE: 1

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
                20                  25                  30

Pro Gly Ala Ser Val Lys Ile Ser Cys Lys Ala Thr Gly Tyr Thr Phe
            35                  40                  45

Ser Ser Tyr Trp Ile Glu Trp Val Lys Gln Arg Pro Gly His Gly Leu
        50                  55                  60

Glu Trp Ile Gly Glu Ile Leu Pro Gly
65                  70

<210> SEQ ID NO 2
<211> LENGTH: 73
<212> TYPE: PRT
<213> ORGANISM: Artificial
<220> FEATURE:
<223> OTHER INFORMATION: Synthetic peptide.

<400> SEQUENCE: 2

Met Glu Trp Thr Trp Val Phe Leu Phe Leu Leu Ser Val Thr Ala Gly
1               5                   10                  15

Val His Ser Gln Val Gln Leu Gln Gln Ser Gly Thr Glu Leu Met Lys
                20                  25                  30

Pro Gly Ala Ser Val Lys Ile Ser Cys Lys Ala Thr Gly Tyr Thr Phe
            35                  40                  45

Ser Thr Tyr Trp Ile Glu Trp Val Lys Gln Arg Pro Gly His Gly Leu
        50                  55                  60

Glu Trp Ile Gly Glu Ile Leu Pro Gly
65                  70

<210> SEQ ID NO 3
<211> LENGTH: 73
<212> TYPE: PRT
<213> ORGANISM: Artificial
<220> FEATURE:
<223> OTHER INFORMATION: Synthetic peptide.

<400> SEQUENCE: 3

Met Gly Trp Ser Tyr Ile Ile Leu Phe Leu Val Ala Thr Ala Thr Asp
1               5                   10                  15

Val His Ser Gln Val Gln Leu Gln Gln Pro Gly Ala Glu Leu Val Lys
                20                  25                  30

Pro Gly Ala Ser Val Lys Leu Ser Cys Lys Ala Ser Gly Tyr Thr Phe
            35                  40                  45

Thr Ser Tyr Trp Met His Trp Val Lys Gln Arg Pro Gly Glu Gly Leu
        50                  55                  60

Glu Trp Ile Gly Glu Ile Asn Pro Ser
65                  70

```
<210> SEQ ID NO 4
<211> LENGTH: 73
<212> TYPE: PRT
<213> ORGANISM: Artificial
<220> FEATURE:
<223> OTHER INFORMATION: Synthetic peptide.

<400> SEQUENCE: 4

Met Glu Cys Asn Trp Ile Leu Pro Phe Ile Leu Ser Val Ile Ser Gly
1               5                   10                  15

Val Tyr Ser Glu Val Gln Leu Gln Gln Ser Gly Thr Val Leu Ala Arg
            20                  25                  30

Pro Gly Ala Ser Val Asn Met Ser Cys Lys Ala Ala Gly Tyr Ser Phe
        35                  40                  45

Thr Ser Tyr Trp Val Tyr Trp Val Lys Gln Arg Pro Gly Gln Gly Leu
    50                  55                  60

Glu Trp Ile Gly Ala Ile Tyr Pro Lys
65                  70

<210> SEQ ID NO 5
<211> LENGTH: 73
<212> TYPE: PRT
<213> ORGANISM: Artificial
<220> FEATURE:
<223> OTHER INFORMATION: Synthetic peptide.

<400> SEQUENCE: 5

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Arg
            20                  25                  30

Pro Gly Ala Leu Val Lys Leu Ser Cys Lys Ala Ser Gly Phe Asn Ile
        35                  40                  45

Asn Asp Tyr Tyr Ile His Trp Val Lys Gln Arg Pro Glu Gln Gly Leu
    50                  55                  60

Glu Arg Ile Gly Trp Ile Asp Pro Asp
65                  70

<210> SEQ ID NO 6
<211> LENGTH: 73
<212> TYPE: PRT
<213> ORGANISM: Artificial
<220> FEATURE:
<223> OTHER INFORMATION: Synthetic peptide.

<400> SEQUENCE: 6

Met Asp Trp Leu Trp Asn Leu Leu Phe Leu Met Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Ser Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr
65                  70

<210> SEQ ID NO 7
<211> LENGTH: 75
<212> TYPE: PRT
<213> ORGANISM: Artificial
<220> FEATURE:
```

<223> OTHER INFORMATION: Synthetic peptide.

<400> SEQUENCE: 7

Met Asn Arg Leu Thr Ser Ser Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
            35                  40                  45

Ser Thr Ser Gly Met Gly Val Ser Trp Ile Arg Gln Pro Ser Gly Lys
        50                  55                  60

Gly Leu Glu Trp Leu Ala His Ile Tyr Trp Asp
65                  70                  75

<210> SEQ ID NO 8
<211> LENGTH: 75
<212> TYPE: PRT
<213> ORGANISM: Artificial
<220> FEATURE:
<223> OTHER INFORMATION: Synthetic peptide.

<400> SEQUENCE: 8

Met Asn Arg Leu Thr Ser Ser Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
            35                  40                  45

Ser Thr Ser Gly Met Gly Leu Ser Trp Ile Arg Gln Pro Ser Gly Lys
        50                  55                  60

Gly Leu Glu Trp Leu Ala His Ile Tyr Trp Asp
65                  70                  75

<210> SEQ ID NO 9
<211> LENGTH: 68
<212> TYPE: PRT
<213> ORGANISM: Artificial
<220> FEATURE:
<223> OTHER INFORMATION: Synthetic peptide.

<400> SEQUENCE: 9

Ser Gly Arg Thr Asn Asp Asn Glu Lys Phe Lys Gly Lys Ala Thr Phe
1               5                   10                  15

Thr Ala Asp Thr Ser Ser Lys Lys Ala Tyr Met Gln Leu Ser Ser Leu
            20                  25                  30

Thr Ser Glu Asp Ser Ala Val Tyr Tyr Cys Ala Arg Arg Gly Gly Tyr
            35                  40                  45

Ser Phe Ala Tyr Trp Gly Gln Gly Thr Leu Val Thr Val Ser Ala Ala
        50                  55                  60

Lys Thr Lys Gly
65

<210> SEQ ID NO 10
<211> LENGTH: 68
<212> TYPE: PRT
<213> ORGANISM: Artificial
<220> FEATURE:
<223> OTHER INFORMATION: Synthetic peptide.

<400> SEQUENCE: 10

Ser Gly Arg Thr Asn Asp Asn Glu Lys Phe Lys Gly Lys Ala Thr Ile

```
                 1               5                  10                 15
Thr Ala Asp Thr Ser Ser Lys Lys Ala Tyr Met Gln Leu Ser Ser Leu
                20                  25                 30

Thr Ser Glu Asp Ser Ala Val Tyr Tyr Cys Ala Arg Arg Gly Gly Tyr
            35                  40                  45

Ser Phe Ala Phe Trp Gly Gln Gly Thr Leu Val Ser Val Ser Ala Ala
        50                  55                  60

Lys Thr Lys Gly
65

<210> SEQ ID NO 11
<211> LENGTH: 70
<212> TYPE: PRT
<213> ORGANISM: Artificial
<220> FEATURE:
<223> OTHER INFORMATION: Synthetic peptide.

<400> SEQUENCE: 11

Tyr Gly Arg Thr Asp Tyr Asn Gly Lys Phe Lys Asn Lys Ala Thr Leu
1               5                   10                  15

Thr Val Ala Lys Ser Ser Thr Ala Tyr Met Gln Leu Ser Ser Leu
                20                  25                  30

Thr Ser Glu Asp Ser Ala Val Tyr Tyr Cys Ala Arg Gly Asp Tyr Tyr
            35                  40                  45

Gly Ser Ser Phe Ala Tyr Trp Gly Gln Gly Thr Leu Val Thr Val Ser
        50                  55                  60

Ala Ala Lys Thr Lys Gly
65                  70

<210> SEQ ID NO 12
<211> LENGTH: 68
<212> TYPE: PRT
<213> ORGANISM: Artificial
<220> FEATURE:
<223> OTHER INFORMATION: Synthetic peptide.

<400> SEQUENCE: 12

Asn Ser Arg Thr Ser Tyr Asn Gln Lys Phe Gln Asp Lys Ala Thr Leu
1               5                   10                  15

Thr Ala Val Thr Ser Ala Ser Thr Ala Tyr Met Glu Leu Ser Ser Leu
                20                  25                  30

Thr Asn Glu Asp Ser Ala Val Tyr Tyr Cys Thr Arg Pro His Tyr Asp
            35                  40                  45

Leu Phe Gly Tyr Trp Gly Gln Gly Thr Leu Val Thr Val Ser Ala Ala
        50                  55                  60

Lys Thr Lys Gly
65

<210> SEQ ID NO 13
<211> LENGTH: 68
<212> TYPE: PRT
<213> ORGANISM: Artificial
<220> FEATURE:
<223> OTHER INFORMATION: Synthetic peptide.

<400> SEQUENCE: 13

Asn Ser Arg Thr Ser Tyr Asn Gln Lys Phe Gln Asp Lys Ala Thr Leu
1               5                   10                  15

Thr Ala Val Thr Ser Ala Ser Thr Ala Tyr Met Glu Leu Ser Ser Leu
                20                  25                  30
```

```
Thr Asn Glu Asp Ser Ala Val Tyr Tyr Cys Thr Arg Pro His Tyr Asp
             35                  40                  45

Ser Phe Gly Tyr Trp Gly Gln Gly Thr Leu Val Thr Val Ser Ala Ala
 50                  55                  60

Lys Thr Lys Gly
 65
```

<210> SEQ ID NO 14
<211> LENGTH: 72
<212> TYPE: PRT
<213> ORGANISM: Artificial
<220> FEATURE:
<223> OTHER INFORMATION: Synthetic peptide.

<400> SEQUENCE: 14

```
Asn Gly Asn Thr Ile Tyr Asp Pro Lys Phe Gln Gly Lys Ala Ser Ile
 1               5                  10                  15

Thr Ala Asp Thr Ser Pro Asn Thr Ala Tyr Leu Gln Leu Ser Ser Leu
             20                  25                  30

Thr Ser Glu Asp Thr Ala Val Tyr Tyr Cys Ala Arg Thr Arg Ser Pro
             35                  40                  45

Met Val Thr Thr Gly Phe Val Tyr Trp Gly Gln Gly Thr Val Val Thr
 50                  55                  60

Val Ser Ala Ala Lys Thr Lys Gly
 65                  70
```

<210> SEQ ID NO 15
<211> LENGTH: 70
<212> TYPE: PRT
<213> ORGANISM: Artificial
<220> FEATURE:
<223> OTHER INFORMATION: Synthetic peptide.

<400> SEQUENCE: 15

```
Thr Gly Glu Ser Thr Tyr Ala Asp Asp Phe Lys Gly Arg Phe Ala Phe
 1               5                  10                  15

Ser Leu Glu Thr Ser Ala Ser Thr Ala Tyr Leu Gln Ile Ser Asn Leu
             20                  25                  30

Lys Asn Glu Asp Met Ala Thr Tyr Phe Cys Ala Arg Gly Asp Phe Arg
             35                  40                  45

Tyr Tyr Tyr Phe Asp Tyr Trp Gly Gln Gly Thr Leu Thr Gly Ser
 50                  55                  60

Ser Ala Lys Thr Lys Gly
 65                  70
```

<210> SEQ ID NO 16
<211> LENGTH: 74
<212> TYPE: PRT
<213> ORGANISM: Artificial
<220> FEATURE:
<223> OTHER INFORMATION: Synthetic peptide.

<400> SEQUENCE: 16

```
Asp Asp Lys Arg Tyr Asn Pro Ser Leu Lys Ser Arg Leu Thr Ile Phe
 1               5                  10                  15

Lys Asp Pro Ser Ser Asn Gln Val Phe Leu Arg Ile Thr Ser Val Asp
             20                  25                  30

Thr Ala Asp Thr Ala Thr Tyr Tyr Cys Ala Arg Asn Ser His Tyr Tyr
             35                  40                  45

Gly Ser Thr Tyr Gly Gly Tyr Phe Asp Val Trp Gly Ala Gly Thr Thr
 50                  55                  60
```

```
Val Thr Val Ser Ser Ala Lys Thr Lys Gly
 65                  70

<210> SEQ ID NO 17
<211> LENGTH: 74
<212> TYPE: PRT
<213> ORGANISM: Artificial
<220> FEATURE:
<223> OTHER INFORMATION: Synthetic peptide.

<400> SEQUENCE: 17

Asp Asp Lys Arg Tyr Asn Pro Ser Leu Lys Ser Arg Leu Thr Ile Ser
 1               5                  10                  15

Lys Asp Thr Ser Ser Asn Gln Val Phe Leu Lys Ile Thr Ile Val Asp
                20                  25                  30

Thr Ala Asp Ala Ala Thr Tyr Tyr Cys Ala Arg Ser Ser His Tyr Tyr
                35                  40                  45

Gly Tyr Gly Tyr Gly Tyr Phe Asp Val Trp Gly Ala Gly Thr Thr
 50                  55                  60

Val Thr Val Ser Ser Ala Lys Thr Lys Gly
 65                  70

<210> SEQ ID NO 18
<211> LENGTH: 62
<212> TYPE: PRT
<213> ORGANISM: Artificial
<220> FEATURE:
<223> OTHER INFORMATION: Synthetic peptide.

<400> SEQUENCE: 18

Met Glu Thr Asp Thr Leu Leu Leu Trp Val Leu Leu Leu Trp Val Pro
 1               5                  10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Arg Ala Ser Glu Ser
                35                  40                  45

Val Asp Ser Tyr Gly Ile Ser Phe Met His Trp Tyr Gln Gln
 50                  55                  60

<210> SEQ ID NO 19
<211> LENGTH: 62
<212> TYPE: PRT
<213> ORGANISM: Artificial
<220> FEATURE:
<223> OTHER INFORMATION: Synthetic peptide.

<400> SEQUENCE: 19

Met Glu Thr Asp Thr Leu Leu Leu Trp Val Leu Leu Leu Trp Val Pro
 1               5                  10                  15

Gly Ser Thr Gly Asp Ile Val Leu Ile Gln Ser Pro Ala Ser Leu Ala
                20                  25                  30

Val Ser Leu Gly Gln Arg Ala Thr Ile Ser Cys Arg Ala Ser Glu Ser
                35                  40                  45

Val Asp Ser Tyr Val Asn Ser Phe Met His Trp Tyr Gln Gln
 50                  55                  60

<210> SEQ ID NO 20
<211> LENGTH: 62
<212> TYPE: PRT
<213> ORGANISM: Artificial
<220> FEATURE:
<223> OTHER INFORMATION: Synthetic peptide.
```

<400> SEQUENCE: 20

Met Glu Thr Asp Thr Leu Leu Leu Trp Val Leu Leu Leu Gly Val Pro
1               5                   10                  15

Gly Ser Thr Gly Asn Ile Val Leu Thr Gln Ser Pro Thr Ser Phe Thr
            20                  25                  30

Val Ser Leu Gly Gln Arg Ala Thr Ile Ser Cys Arg Ala Ser Glu Ser
        35                  40                  45

Val His Ser Tyr Gly Asn Ser Phe Met His Trp Tyr Gln Gln
    50                  55                  60

<210> SEQ ID NO 21
<211> LENGTH: 62
<212> TYPE: PRT
<213> ORGANISM: Artificial
<220> FEATURE:
<223> OTHER INFORMATION: Synthetic peptide.

<400> SEQUENCE: 21

Met Glu Thr Asp Thr Leu Leu Leu Trp Val Leu Leu Leu Trp Val Pro
1               5                   10                  15

Gly Ser Thr Gly Asn Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Ile His Ser Tyr Gly Asn Ser Phe Leu His Trp Tyr Gln Gln
    50                  55                  60

<210> SEQ ID NO 22
<211> LENGTH: 59
<212> TYPE: PRT
<213> ORGANISM: Artificial
<220> FEATURE:
<223> OTHER INFORMATION: Chemically synthesized peptide

<400> SEQUENCE: 22

Met Asp Phe Arg Val Gln Ile Phe Ser Phe Leu Leu Met Ser Ala Ser
1               5                   10                  15

Val Ile Met Ser Arg Gly Gln Ile Val Leu Thr Gln Ser Pro Ala Leu
            20                  25                  30

Met Ser Ala Ser Pro Gly Glu Lys Val Thr Met Thr Cys Ser Ala Ser
        35                  40                  45

Ser Asn Ile Ser Tyr Met Tyr Trp Tyr Gln Gln
    50                  55

<210> SEQ ID NO 23
<211> LENGTH: 59
<212> TYPE: PRT
<213> ORGANISM: Artificial
<220> FEATURE:
<223> OTHER INFORMATION: Synthetic peptide.

<400> SEQUENCE: 23

Met Asp Phe Gln Val Gln Ile Phe Ser Phe Leu Leu Met Ser Ala Ser
1               5                   10                  15

Val Ile Met Ser Arg Gly Gln Ile Val Leu Thr Gln Ser Pro Ala Leu
            20                  25                  30

Met Ser Ala Ser Pro Gly Glu Lys Val Thr Met Thr Cys Ser Ala Ser
        35                  40                  45

Ser Asn Ile Ser Tyr Met Tyr Trp Tyr Gln Gln
    50                  55

<210> SEQ ID NO 24
<211> LENGTH: 59
<212> TYPE: PRT
<213> ORGANISM: Artificial
<220> FEATURE:
<223> OTHER INFORMATION: Synthetic peptide.

<400> SEQUENCE: 24

Met Ser Val Leu Thr Gln Val Leu Ala Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Gly Asn
        35                  40                  45

Ile His Asn Tyr Leu Ala Trp Tyr Gln Gln Glu
    50                  55

<210> SEQ ID NO 25
<211> LENGTH: 58
<212> TYPE: PRT
<213> ORGANISM: Artificial
<220> FEATURE:
<223> OTHER INFORMATION: Synthetic peptide.

<400> SEQUENCE: 25

Met Ser Val Leu Thr Gln Val Leu Ala Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Thr Ser Gly Asn
        35                  40                  45

Ile Arg Asn Tyr Leu Ala Trp Tyr Gln Gln
    50                  55

<210> SEQ ID NO 26
<211> LENGTH: 60
<212> TYPE: PRT
<213> ORGANISM: Artificial
<220> FEATURE:
<223> OTHER INFORMATION: Synthetic peptide.

<400> SEQUENCE: 26

Met Thr Met Phe Ser Leu Ala Leu Leu Leu Ser Leu Leu Leu Leu Cys
1               5                   10                  15

Val Ser Asp Ser Arg Ala Glu Thr Thr Val Thr Gln Ser Pro Ala Ser
            20                  25                  30

Leu Ser Met Ala Ile Gly Glu Lys Val Thr Ile Arg Cys Val Thr Ser
        35                  40                  45

Thr Asp Ile Asp Asp Asp Val Asn Trp Tyr Gln Gln
    50                  55                  60

<210> SEQ ID NO 27
<211> LENGTH: 60
<212> TYPE: PRT
<213> ORGANISM: Artificial
<220> FEATURE:
<223> OTHER INFORMATION: Synthetic peptide.

<400> SEQUENCE: 27

Met Thr Met Phe Ser Leu Ala Leu Leu Leu Ser Leu Leu Leu Leu Cys
1               5                   10                  15

```
Val Ser Asp Ser Arg Ala Glu Thr Thr Val Thr Gln Ser Pro Ala Ser
            20                  25                  30

Leu Ser Met Ala Ile Gly Glu Lys Val Thr Ile Arg Cys Val Thr Ser
            35                  40                  45

Thr Asp Ile Asp Asp Val Asn Trp Tyr Gln Gln
            50                  55                  60

<210> SEQ ID NO 28
<211> LENGTH: 66
<212> TYPE: PRT
<213> ORGANISM: Artificial
<220> FEATURE:
<223> OTHER INFORMATION: Synthetic peptide.

<400> SEQUENCE: 28

Lys Pro Gly Gln Pro Pro Lys Leu Leu Ile Tyr Arg Ala Ser Asn Gln
1               5                   10                  15

Glu Ser Gly Ile Pro Ala Arg Phe Ser Gly Ser Gly Ser Arg Thr Asp
            20                  25                  30

Phe Thr Leu Thr Ile Asn Pro Val Glu Ala Asp Asp Val Ala Thr Tyr
            35                  40                  45

Tyr Cys Gln Gln Ser Asn Glu Asp Pro Leu Thr Phe Gly Ala Gly Thr
            50                  55                  60

Lys Leu
65

<210> SEQ ID NO 29
<211> LENGTH: 66
<212> TYPE: PRT
<213> ORGANISM: Artificial
<220> FEATURE:
<223> OTHER INFORMATION: Synthetic peptide.

<400> SEQUENCE: 29

Lys Pro Gly Gln Pro Pro Lys Leu Leu Ile Tyr Arg Ala Ser Asn Gln
1               5                   10                  15

Glu Ser Gly Ile Pro Ala Arg Phe Ser Gly Ser Gly Ser Arg Thr Asp
            20                  25                  30

Phe Thr Pro Thr Ile Asn Pro Val Glu Ala Asp Asp Val Ala Thr Tyr
            35                  40                  45

Tyr Cys Gln Gln Ser Asn Glu Asp Pro Leu Thr Phe Gly Ala Gly Thr
            50                  55                  60

Lys Leu
65

<210> SEQ ID NO 30
<211> LENGTH: 66
<212> TYPE: PRT
<213> ORGANISM: Artificial
<220> FEATURE:
<223> OTHER INFORMATION: Synthetic peptide.

<400> SEQUENCE: 30

Lys Pro Gly Gln Pro Pro Lys Leu Leu Ile Tyr Arg Val Ser Asn Leu
1               5                   10                  15

Glu Ser Gly Ile Pro Ala Arg Phe Ser Gly Ser Gly Ser Arg Thr Asp
            20                  25                  30

Phe Thr Leu Thr Ile Asn Pro Val Glu Ala Asp Asp Val Ala Thr Tyr
            35                  40                  45

Tyr Cys Gln Gln Ser Asn Glu Asp Pro Phe Thr Phe Gly Ser Gly Thr
            50                  55                  60
```

Lys Leu
65

<210> SEQ ID NO 31
<211> LENGTH: 66
<212> TYPE: PRT
<213> ORGANISM: Artificial
<220> FEATURE:
<223> OTHER INFORMATION: Synthetic peptide.

<400> SEQUENCE: 31

Lys Pro Gly Gln Pro Pro Lys Leu Leu Ile Tyr Leu Ala Ser Asn Val
1               5                   10                  15

Glu Ser Gly Val Pro Ala Lys Phe Ser Gly Ser Gly Ser Arg Thr Asp
            20                  25                  30

Phe Thr Leu Thr Ile Asp Pro Val Glu Ala Asp Asp Ala Ala Thr Tyr
        35                  40                  45

Tyr Cys Gln Gln Asn Ser Glu Asp Pro Trp Thr Phe Gly Gly Gly Thr
    50                  55                  60

Lys Leu
65

<210> SEQ ID NO 32
<211> LENGTH: 66
<212> TYPE: PRT
<213> ORGANISM: Artificial
<220> FEATURE:
<223> OTHER INFORMATION: Synthetic peptide.

<400> SEQUENCE: 32

Lys Pro Gly Gln Pro Pro Lys Leu Leu Ile Tyr Leu Ala Ser Asn Val
1               5                   10                  15

Glu Ser Gly Val Pro Ala Arg Phe Ser Gly Ser Gly Ser Arg Thr Asp
            20                  25                  30

Phe Thr Leu Thr Ile Asp Pro Val Glu Ala Asp Asp Ala Ala Thr Tyr
        35                  40                  45

Tyr Cys Gln Gln Asn Ser Glu Asp Pro Trp Thr Phe Gly Gly Gly Thr
    50                  55                  60

Lys Leu
65

<210> SEQ ID NO 33
<211> LENGTH: 66
<212> TYPE: PRT
<213> ORGANISM: Artificial
<220> FEATURE:
<223> OTHER INFORMATION: Synthetic peptide.

<400> SEQUENCE: 33

Lys Pro Gly Gln Pro Pro Lys Leu Leu Ile Tyr Leu Ala Ser Asn Leu
1               5                   10                  15

Glu Ser Gly Val Pro Ala Arg Phe Ser Gly Ser Gly Ser Arg Thr Asp
            20                  25                  30

Phe Thr Leu Thr Ile Asp Pro Val Glu Ala Asp Asp Ala Ala Thr Tyr
        35                  40                  45

Tyr Cys Gln Gln Asn Asn Glu Asp Pro Trp Thr Phe Gly Gly Gly Thr
    50                  55                  60

Lys Leu
65

```
<210> SEQ ID NO 34
<211> LENGTH: 66
<212> TYPE: PRT
<213> ORGANISM: Artificial
<220> FEATURE:
<223> OTHER INFORMATION: Synthetic peptide.

<400> SEQUENCE: 34

Lys Pro Arg Ser Ser Pro Lys Pro Trp Ile Tyr Leu Thr Ser Asn Leu
1               5                   10                  15

Ala Ser Gly Val Pro Ala Arg Phe Ser Gly Ser Gly Ser Gly Thr Ser
                20                  25                  30

Tyr Ser Leu Thr Ile Ser Ser Met Glu Ala Glu Asp Ala Ala Thr Tyr
                35                  40                  45

Tyr Cys Gln Gln Trp Ser Ser Asn Pro Pro Thr Phe Gly Ala Gly Thr
    50                  55                  60

Lys Leu
65

<210> SEQ ID NO 35
<211> LENGTH: 66
<212> TYPE: PRT
<213> ORGANISM: Artificial
<220> FEATURE:
<223> OTHER INFORMATION: Synthetic peptide.

<400> SEQUENCE: 35

Lys Pro Arg Ser Ser Pro Lys Pro Trp Ile Tyr Leu Thr Ser Asn Leu
1               5                   10                  15

Ala Ser Gly Val Pro Ala Arg Phe Ser Gly Ser Gly Ser Gly Thr Ser
                20                  25                  30

Tyr Ser Leu Thr Thr Ser Ser Met Glu Ala Glu Asp Ala Ala Thr Tyr
                35                  40                  45

Cys Cys Gln Gln Trp Ser Ser Asn Pro Pro Thr Phe Gly Ala Gly Thr
    50                  55                  60

Lys Leu
65

<210> SEQ ID NO 36
<211> LENGTH: 65
<212> TYPE: PRT
<213> ORGANISM: Artificial
<220> FEATURE:
<223> OTHER INFORMATION: Synthetic peptide.

<400> SEQUENCE: 36

Lys Gln Gly Lys Ser Pro Gln Leu Leu Val Tyr Asn Ala Lys Thr Leu
1               5                   10                  15

Ala Asp Gly Val Pro Ser Arg Phe Ser Gly Ser Gly Ser Gly Thr Gln
                20                  25                  30

Tyr Ser Leu Lys Ile Asn Thr Leu Gln Pro Glu Asp Phe Gly Ser Tyr
                35                  40                  45

Tyr Cys Gln His Phe Trp Asp Ser Trp Thr Phe Gly Gly Gly Thr Lys
    50                  55                  60

Leu
65

<210> SEQ ID NO 37
<211> LENGTH: 66
<212> TYPE: PRT
<213> ORGANISM: Artificial
<220> FEATURE:
```

<223> OTHER INFORMATION: Synthetic peptide.

<400> SEQUENCE: 37

Lys Gln Gly Lys Ser Pro Gln Leu Leu Val Tyr Asn Ala Lys Thr Leu
1               5                   10                  15

Ala Asp Gly Val Pro Ser Arg Phe Gly Gly Ser Gly Ser Gly Thr Gln
            20                  25                  30

Tyr Ser Leu Lys Ile Asn Ser Leu Gln Pro Glu Asp Phe Gly Asn Tyr
        35                  40                  45

Tyr Cys Gln His Phe Trp Ser Ser Pro Tyr Thr Phe Gly Gly Gly Thr
    50                  55                  60

Lys Leu
65

<210> SEQ ID NO 38
<211> LENGTH: 66
<212> TYPE: PRT
<213> ORGANISM: Artificial
<220> FEATURE:
<223> OTHER INFORMATION: Synthetic peptide.

<400> SEQUENCE: 38

Lys Pro Gly Glu Pro Pro Lys Leu Leu Ile Ser Glu Gly Asn Thr Leu
1               5                   10                  15

Arg Pro Gly Val Pro Ser Arg Phe Ser Ser Gly Tyr Gly Thr Asp
            20                  25                  30

Phe Val Phe Thr Ile Glu Asn Met Leu Ser Glu Asp Val Ala Asp Tyr
        35                  40                  45

Tyr Cys Leu Gln Ser Gly Asn Leu Pro Tyr Thr Phe Gly Gly Gly Thr
    50                  55                  60

Lys Leu
65

<210> SEQ ID NO 39
<211> LENGTH: 66
<212> TYPE: PRT
<213> ORGANISM: Artificial
<220> FEATURE:
<223> OTHER INFORMATION: Synthetic peptide.

<400> SEQUENCE: 39

Lys Pro Gly Glu Pro Pro Lys Leu Leu Ile Ser Glu Gly Asn Thr Leu
1               5                   10                  15

Arg Ala Gly Val Pro Ser Arg Phe Ser Ser Gly Tyr Gly Thr Asp
            20                  25                  30

Phe Val Phe Thr Ile Glu Asn Met Leu Ser Glu Asp Val Ala Asp Tyr
        35                  40                  45

Tyr Cys Leu Gln Ser Gly Asn Leu Pro Tyr Thr Phe Gly Gly Gly Thr
    50                  55                  60

Lys Leu
65

<210> SEQ ID NO 40
<211> LENGTH: 71
<212> TYPE: PRT
<213> ORGANISM: Artificial
<220> FEATURE:
<223> OTHER INFORMATION: Synthetic peptide.

<400> SEQUENCE: 40

Ala Ser Asp Thr Thr Glu Ala Arg His Pro His Pro Pro Val Thr Thr

```
                1               5                  10                 15
Pro Thr Thr Asp Arg Lys Gly Thr Thr Ala Glu Glu Leu Ala Gly Ile
                20                 25                 30

Gly Ile Leu Thr Val Ile Leu Gly Gly Lys Arg Thr Asn Asn Ser Thr
            35                 40                 45

Pro Thr Lys Gly Glu Phe Cys Arg Tyr Pro Ser His Trp Arg Pro Leu
    50                 55                 60

Glu His His His His His His
65                  70

<210> SEQ ID NO 41
<211> LENGTH: 11
<212> TYPE: PRT
<213> ORGANISM: Artificial
<220> FEATURE:
<223> OTHER INFORMATION: Synthetic peptide.

<400> SEQUENCE: 41

Gly Gly Ser Gly Gly Ser Gly Gly Ser Leu Asp
1               5                   10

<210> SEQ ID NO 42
<211> LENGTH: 36
<212> TYPE: DNA
<213> ORGANISM: Artificial
<220> FEATURE:
<223> OTHER INFORMATION: Synthetic oligonucleotide.

<400> SEQUENCE: 42
ggatggtggg aagatggata cagttggtgc agcatc                              36

<210> SEQ ID NO 43
<211> LENGTH: 48
<212> TYPE: DNA
<213> ORGANISM: Artificial
<220> FEATURE:
<223> OTHER INFORMATION: Synthetic oligonucleotide.

<400> SEQUENCE: 43
ctaggaacag tcagcacggg acaaactctt ctccacagtg tgaccttc                 48

<210> SEQ ID NO 44
<211> LENGTH: 37
<212> TYPE: DNA
<213> ORGANISM: Artificial
<220> FEATURE:
<223> OTHER INFORMATION: Synthetic oligonucleotide.

<400> SEQUENCE: 44
gtcactggct cagggaaata gcccttgacc aggcatc                             37

<210> SEQ ID NO 45
<211> LENGTH: 31
<212> TYPE: DNA
<213> ORGANISM: Artificial
<220> FEATURE:
<223> OTHER INFORMATION: Synthetic oligonucleotide.

<400> SEQUENCE: 45
ccaggcatcc tagagtcacc gaggagccag t                                   31

<210> SEQ ID NO 46
<211> LENGTH: 38
<212> TYPE: DNA
<213> ORGANISM: Artificial
```

```
<220> FEATURE:
<223> OTHER INFORMATION: Synthetic oligonucleotide.

<400> SEQUENCE: 46
ggtgctggag gggacagtca ctgagctgct catagtgt                               38

<210> SEQ ID NO 47
<211> LENGTH: 107
<212> TYPE: DNA
<213> ORGANISM: Artificial
<220> FEATURE:
<223> OTHER INFORMATION: Synthetic oligonucleotide.

<400> SEQUENCE: 47
ctagttgctg gctaatggac cccaaaggct ccctttcctg gagaatactt ctgtttctct       60
ccctggcttt tgagttgtcg tacggattaa ttaagggccc actcgag                    107

<210> SEQ ID NO 48
<211> LENGTH: 100
<212> TYPE: DNA
<213> ORGANISM: Artificial
<220> FEATURE:
<223> OTHER INFORMATION: Synthetic oligonucleotide.

<400> SEQUENCE: 48
ctagttgctg gctaatggac cccaaaggct ccctttcctg gagaatactt ctgtttctct       60
ccctggcttt tgagttgtcg tacggattaa ttaagggccc                            100

<210> SEQ ID NO 49
<211> LENGTH: 46
<212> TYPE: DNA
<213> ORGANISM: Artificial
<220> FEATURE:
<223> OTHER INFORMATION: Synthetic oligonucleotide.

<400> SEQUENCE: 49
gctagcgata caacagaacc tgcaacacct acaacacctg taacaa                      46

<210> SEQ ID NO 50
<211> LENGTH: 29
<212> TYPE: DNA
<213> ORGANISM: Artificial
<220> FEATURE:
<223> OTHER INFORMATION: Synthetic oligonucleotide.

<400> SEQUENCE: 50
caccatcacc atcaccattg agcggccgc                                         29

<210> SEQ ID NO 51
<211> LENGTH: 70
<212> TYPE: DNA
<213> ORGANISM: Artificial
<220> FEATURE:
<223> OTHER INFORMATION: Synthetic oligonucleotide.

<400> SEQUENCE: 51
gctagcgata caacagaacc tgcaacacct acaacacctg taacaacacc gacaacaaca       60
cttctagcgc                                                              70

<210> SEQ ID NO 52
<211> LENGTH: 119
<212> TYPE: DNA
<213> ORGANISM: Artificial
<220> FEATURE:
<223> OTHER INFORMATION: Synthetic oligonucleotide.
```

-continued

```
<400> SEQUENCE: 52
gctagcccca ttctgagccc cctgaccaaa ggcattctgg gctttgtgtt taccctgacc      60
gtgcccagcg aacgcaaggg tatacttgga ttcgttttca cacttactta agcggccgc     119
```

<210> SEQ ID NO 53
<211> LENGTH: 9
<212> TYPE: PRT
<213> ORGANISM: Artificial
<220> FEATURE:
<223> OTHER INFORMATION: Synthetic peptide.

<400> SEQUENCE: 53

Gly Ile Leu Gly Phe Val Phe Thr Leu
1               5

<210> SEQ ID NO 54
<211> LENGTH: 9
<212> TYPE: PRT
<213> ORGANISM: Artificial
<220> FEATURE:
<223> OTHER INFORMATION: Synthetic peptide.

<400> SEQUENCE: 54

Ile Leu Lys Glu Pro Val His Gly Val
1               5

<210> SEQ ID NO 55
<211> LENGTH: 10
<212> TYPE: PRT
<213> ORGANISM: Artificial
<220> FEATURE:
<223> OTHER INFORMATION: Synthetic peptide.

<400> SEQUENCE: 55

Lys Tyr Thr Ala Phe Thr Ile Pro Ser Ile
1               5                   10

<210> SEQ ID NO 56
<211> LENGTH: 9
<212> TYPE: PRT
<213> ORGANISM: Artificial
<220> FEATURE:
<223> OTHER INFORMATION: Synthetic peptide.

<400> SEQUENCE: 56

Ser Leu Tyr Asn Thr Val Ala Thr Leu
1               5

<210> SEQ ID NO 57
<211> LENGTH: 9
<212> TYPE: PRT
<213> ORGANISM: Artificial
<220> FEATURE:
<223> OTHER INFORMATION: Synthetic peptide.

<400> SEQUENCE: 57

Thr Leu Asn Ala Trp Val Lys Val Val
1               5

<210> SEQ ID NO 58
<211> LENGTH: 80
<212> TYPE: PRT
<213> ORGANISM: Artificial
<220> FEATURE:
<223> OTHER INFORMATION: Synthetic peptide.

-continued

```
<400> SEQUENCE: 58

Met Thr Ser Glu Ile Thr Tyr Ala Glu Val Arg Phe Lys Asn Glu Phe
1               5                   10                  15

Lys Ser Ser Gly Ile Asn Thr Ala Ser Ser Ala Ala Ser Lys Glu Arg
            20                  25                  30

Thr Ala Pro His Lys Ser Asn Thr Gly Phe Pro Lys Leu Leu Cys Ala
        35                  40                  45

Ser Leu Leu Ile Phe Phe Leu Leu Ala Ile Ser Phe Phe Ile Ala
    50                  55                  60

Phe Val Ile Phe Phe Gln Lys Tyr Ser Gln Leu Leu Glu Lys Lys Thr
65                  70                  75                  80

<210> SEQ ID NO 59
<211> LENGTH: 79
<212> TYPE: PRT
<213> ORGANISM: Artificial
<220> FEATURE:
<223> OTHER INFORMATION: Synthetic peptide.

<400> SEQUENCE: 59

Met Thr Ser Glu Ile Thr Tyr Ala Glu Val Arg Gln Asn Glu Ser Lys
1               5                   10                  15

Ser Ser Gly Ile Asp Ser Ala Ser Ser Ala Ala Ser Lys Lys Arg Thr
            20                  25                  30

Ala Pro His Lys Ser Asn Thr Gly Phe Ser Lys Leu Leu Cys Ala Ser
        35                  40                  45

Leu Met Ile Phe Phe Leu Leu Ala Ile Ser Phe Phe Phe Ala Phe
    50                  55                  60

Phe Ile Phe Phe Gln Lys Tyr Ser Gln Leu Leu Glu Lys Met Thr
65                  70                  75

<210> SEQ ID NO 60
<211> LENGTH: 80
<212> TYPE: PRT
<213> ORGANISM: Artificial
<220> FEATURE:
<223> OTHER INFORMATION: Synthetic peptide.

<400> SEQUENCE: 60

Thr Lys Glu Leu Val His Thr Thr Leu Glu Cys Val Lys Asn Met
1               5                   10                  15

Pro Val Glu Glu Thr Ala Trp Ser Cys Cys Pro Lys Asn Trp Lys Ser
            20                  25                  30

Phe Ser Ser Asn Cys Tyr Phe Ile Ser Thr Glu Ser Ala Ser Trp Gln
        35                  40                  45

Asp Ser Glu Lys Asp Cys Ala Arg Met Glu Ala His Leu Leu Val Ile
    50                  55                  60

Asn Thr Gln Glu Glu Gln Asp Phe Ile Phe Gln Asn Leu Gln Glu Glu
65                  70                  75                  80

<210> SEQ ID NO 61
<211> LENGTH: 80
<212> TYPE: PRT
<213> ORGANISM: Artificial
<220> FEATURE:
<223> OTHER INFORMATION: Synthetic peptide.

<400> SEQUENCE: 61

Thr Lys Asp Leu Val His Thr Thr Leu Glu Cys Val Lys Asn Met
1               5                   10                  15
```

```
Thr Thr Glu Glu Thr Ala Trp Ser Cys Cys Pro Lys Asn Trp Lys Pro
            20                  25                  30

Phe Ser Ser Asn Cys Tyr Phe Ile Ser Thr Glu Ser Ala Ser Trp Gln
        35                  40                  45

Lys Ser Glu Lys Asp Cys Ala Arg Met Glu Ala His Leu Leu Val Ile
    50                  55                  60

Asn Thr Arg Glu Glu Gln Asp Phe Ile Phe Gln Asn Leu Gln Glu Glu
65                  70                  75                  80

<210> SEQ ID NO 62
<211> LENGTH: 77
<212> TYPE: PRT
<213> ORGANISM: Artificial
<220> FEATURE:
<223> OTHER INFORMATION: Synthetic peptide.

<400> SEQUENCE: 62

Ser Ala Tyr Phe Val Gly Leu Ser Asp Pro Glu Gly Gln Arg His Trp
1               5                   10                  15

Gln Trp Val Asp Gln Thr Pro Tyr Asn Glu Ser Ser Thr Phe Trp His
            20                  25                  30

Pro Arg Glu Pro Ser Asp Pro Asn Glu Arg Cys Val Val Leu Asn Phe
        35                  40                  45

Arg Lys Ser Pro Lys Arg Trp Gly Trp Asn Asp Val Asn Cys Leu Gly
    50                  55                  60

Pro Gln Arg Ser Val Cys Glu Met Met Lys Ile His Leu
65                  70                  75

<210> SEQ ID NO 63
<211> LENGTH: 77
<212> TYPE: PRT
<213> ORGANISM: Artificial
<220> FEATURE:
<223> OTHER INFORMATION: Synthetic peptide.

<400> SEQUENCE: 63

Ser Ala Tyr Phe Val Gly Leu Ser Asp Pro Glu Gly Gln Arg His Trp
1               5                   10                  15

Gln Trp Val Asp Gln Thr Pro Tyr Asn Glu Ser Ser Thr Phe Trp His
            20                  25                  30

Pro His Glu Pro Ser Asp Pro Asp Glu Arg Cys Val Val Leu Asn Phe
        35                  40                  45

Arg Lys Thr Pro Lys Arg Trp Gly Trp Asn Asp Val His Cys Ile Val
    50                  55                  60

Pro Gln Arg Ser Val Cys Glu Met Met Lys Ile His Leu
65                  70                  75

<210> SEQ ID NO 64
<211> LENGTH: 9
<212> TYPE: PRT
<213> ORGANISM: Artificial
<220> FEATURE:
<223> OTHER INFORMATION: Synthetic peptide.

<400> SEQUENCE: 64

Gly Ile Leu Gly Phe Val Phe Thr Leu
1               5
```